(12) United States Patent
Alphonse

(10) Patent No.: US 7,190,464 B2
(45) Date of Patent: Mar. 13, 2007

(54) LOW COHERENCE INTERFEROMETRY FOR DETECTING AND CHARACTERIZING PLAQUES

(75) Inventor: Gerard A. Alphonse, Princeton, NJ (US)

(73) Assignee: Medeikon Corporation, Ewing, NJ (US)

(*) Notice: Subject to any disclaimer, the term of this patent is extended or adjusted under 35 U.S.C. 154(b) by 230 days.

(21) Appl. No.: 11/041,177

(22) Filed: Jan. 21, 2005

(65) Prior Publication Data

US 2005/0254061 A1   Nov. 17, 2005

Related U.S. Application Data

(63) Continuation-in-part of application No. 10/845,849, filed on May 14, 2004.

(51) Int. Cl.
   G01B 9/02 (2006.01)

(52) U.S. Cl. .................................................. 356/479

(58) Field of Classification Search ................ 356/477, 356/479, 497; 250/227.19, 227.27; 385/12
   See application file for complete search history.

(56) References Cited

U.S. PATENT DOCUMENTS

| | | | |
|---|---|---|---|
| 4,596,466 A * | 6/1986 | Ulrich ........................ 356/497 |
| 4,883,953 A | 11/1989 | Koashi | |
| 5,202,745 A | 4/1993 | Sorin | |
| 5,321,501 A | 6/1994 | Swanson | |
| 5,341,205 A | 8/1994 | McLandrich | |
| 5,383,467 A | 1/1995 | Auer | |
| 5,398,681 A | 3/1995 | Kupershmidt | |
| 5,434,791 A | 7/1995 | Koko | |
| 5,459,570 A | 10/1995 | Swanson | |
| 5,465,147 A | 11/1995 | Swanson | |
| 5,491,552 A | 2/1996 | Knuttel | |
| 5,501,226 A | 3/1996 | Petersen | |

(Continued)

FOREIGN PATENT DOCUMENTS

| EP | 0831312 A1 | 3/1998 |
|---|---|---|
| EP | 0831312 B1 | 10/2001 |
| WO | WO9932897 A2 | 12/1997 |
| WO | WO9957507 A1 | 4/1998 |

(Continued)

OTHER PUBLICATIONS

Aryan Vink, "Atherosclerotic Plaques: How Vulernable is the Definition of the Vulnerable Plaque"? Journal of Interventional Cardiology, vol. 16, No. 2, 2003, pp, 115-122.

(Continued)

*Primary Examiner*—Hwa (Andrew) Lee
*Assistant Examiner*—Michael A. Lyons
(74) *Attorney, Agent, or Firm*—Cantor Colburn LLP

(57) ABSTRACT

A method and system for determining a characteristic of a biological sample including directing light at the biological sample and receiving that light; directing the light at a reference reflecting device and receiving that light; adjusting an effective light path length to facilitate an interference of the light reflected from the biological sample corresponding to a first depth and the light reflected from the reference reflecting device; and detecting the broadband light resulting from the interference, to provide an interference signal. The method also includes: determining a first phase associated with the interference signal corresponding to the first depth; varying the effective light path length to define a second depth; determining a second phase associated with the interference signal corresponding to the second depth; and determining the characteristic of the biological sample from the phases.

70 Claims, 23 Drawing Sheets

U.S. PATENT DOCUMENTS

| | | |
|---|---|---|
| 5,507,288 A | 4/1996 | Bocker |
| 5,549,114 A | 8/1996 | Petersen |
| 5,565,986 A | 10/1996 | Knuttel |
| 5,582,171 A | 12/1996 | Chornenky |
| 5,710,630 A | 1/1998 | Essenpreis |
| 5,830,145 A | 11/1998 | Tenhoff |
| 5,835,215 A | 11/1998 | Toida |
| 5,835,642 A | 11/1998 | Gelikonov |
| 5,836,877 A | 11/1998 | Zavislan |
| 5,847,827 A | 12/1998 | Fercher |
| 5,850,287 A * | 12/1998 | Sorin et al. .................. 356/503 |
| 5,867,268 A | 2/1999 | Gelikonov |
| 5,877,856 A | 3/1999 | Fercher |
| 5,883,717 A | 3/1999 | DiMarzio |
| 5,892,583 A | 4/1999 | Li |
| 5,905,572 A | 5/1999 | Li |
| 5,920,390 A | 7/1999 | Farahi |
| 5,921,926 A | 7/1999 | Rolland |
| 5,943,133 A | 8/1999 | Zeylikovich |
| 5,956,355 A | 9/1999 | Swanson |
| 5,962,852 A | 10/1999 | Knuettel |
| 5,991,697 A | 11/1999 | Nelson |
| 5,994,690 A | 11/1999 | Kulkarni et al. ............ 250/216 |
| 6,002,480 A | 12/1999 | Izatt |
| 6,006,128 A | 12/1999 | Izatt |
| 6,014,214 A | 1/2000 | Li |
| 6,020,963 A | 2/2000 | DiMarzio |
| 6,037,579 A | 3/2000 | Chan |
| 6,053,613 A | 4/2000 | Wei |
| 6,057,920 A | 5/2000 | Fercher |
| 6,069,698 A | 5/2000 | Ozawa |
| 6,072,765 A | 6/2000 | Rolland |
| 6,111,645 A | 8/2000 | Tearney |
| 6,124,930 A | 9/2000 | Fercher |
| 6,134,003 A | 10/2000 | Tearney |
| 6,141,577 A | 10/2000 | Rolland |
| 6,144,449 A | 11/2000 | Knuettel |
| 6,152,875 A | 11/2000 | Hakamata |
| 6,160,826 A | 12/2000 | Swanson |
| 6,175,669 B1 | 1/2001 | Colston |
| 6,198,540 B1 | 3/2001 | Ueda |
| 6,201,608 B1 | 3/2001 | Mandella |
| 6,208,415 B1 | 3/2001 | De Boer |
| 6,219,055 B1 | 4/2001 | Bhargava |
| 6,226,089 B1 | 5/2001 | Hakamata |
| 6,233,055 B1 | 5/2001 | Mandella |
| 6,252,666 B1 | 6/2001 | Mandella |
| 6,268,921 B1 | 7/2001 | Seitz |
| 6,282,011 B1 | 8/2001 | Tearney |
| 6,288,784 B1 | 9/2001 | Hitzenberger |
| 6,304,373 B1 | 10/2001 | Zavislan |
| 6,307,633 B1 | 10/2001 | Mandella et al. |
| 6,307,634 B2 | 10/2001 | Hitzenberger |
| 6,330,063 B1 | 12/2001 | Knuettel |
| 6,351,325 B1 | 2/2002 | Mandella |
| 6,370,422 B1 | 4/2002 | Richards-Kortum |
| 6,377,349 B1 | 4/2002 | Fercher |
| 6,381,015 B1 | 4/2002 | Sonehara |
| 6,381,025 B1 | 4/2002 | Bornhop |
| 6,381,490 B1 | 4/2002 | Ostrovsky |
| 6,384,915 B1 | 5/2002 | Everett |
| 6,385,358 B1 | 5/2002 | Everett |
| 6,390,978 B1 | 5/2002 | Irion |
| 6,407,872 B1 | 6/2002 | Lai |
| 6,419,360 B1 | 7/2002 | Hauger |
| 6,421,164 B2 | 7/2002 | Tearney |
| 6,423,956 B1 | 7/2002 | Mandella |
| 6,430,455 B1 | 8/2002 | Rebello |
| 6,437,867 B2 | 8/2002 | Zeylikovich |
| 6,441,356 B1 | 8/2002 | Mandella |
| 6,445,939 B1 | 9/2002 | Swanson |
| 6,445,944 B1 | 9/2002 | Ostrovsky |
| 6,456,769 B1 | 9/2002 | Furusawa |
| 6,466,713 B2 | 10/2002 | Everett |
| 6,469,489 B1 | 10/2002 | Bourquin |
| 6,477,403 B1 | 11/2002 | Eguchi |
| 6,485,413 B1 | 11/2002 | Boppart |
| 6,496,267 B1 | 12/2002 | Takaoka |
| 6,498,948 B1 | 12/2002 | Ozawa |
| 6,501,551 B1 | 12/2002 | Tearney |
| 6,507,747 B1 | 1/2003 | Gowda |
| 6,519,076 B2 | 2/2003 | Fisher |
| 6,522,913 B2 | 2/2003 | Swanson |
| 6,525,862 B2 | 2/2003 | Fisher |
| 6,527,708 B1 | 3/2003 | Nakamura |
| 6,538,817 B1 | 3/2003 | Farmer |
| 6,546,272 B1 | 4/2003 | MacKinnon |
| 6,549,801 B1 | 4/2003 | Chen |
| 6,552,796 B2 | 4/2003 | Magnin |
| 6,564,087 B1 | 5/2003 | Pitris |
| 6,564,089 B2 | 5/2003 | Izatt |
| 6,570,659 B2 | 5/2003 | Schmitt |
| 6,571,117 B1 | 5/2003 | Marbach |
| 6,577,394 B1 | 6/2003 | Zavislan |
| 6,615,071 B1 | 9/2003 | Casscells |
| 6,701,181 B2 | 3/2004 | Tang et al. |
| 2001/0047137 A1 | 11/2001 | Moreno |
| 2003/0023152 A1 | 1/2003 | Abbink |
| 2003/0028100 A1 | 2/2003 | Tearney |
| 2003/0055307 A1 | 3/2003 | Elmaleh |
| 2003/0076528 A1 | 4/2003 | Cornsweet |
| 2003/0112444 A1 | 6/2003 | Yang et al. .................. 356/486 |
| 2003/0137669 A1 | 7/2003 | Rollins |
| 2003/0171691 A1 | 9/2003 | Casscella |
| 2005/0254058 A1 | 11/2005 | Alphonse ..................... 356/479 |

FOREIGN PATENT DOCUMENTS

| | | |
|---|---|---|
| WO | WO0112060 A2 | 8/2000 |
| WO | WO2002/02080767 | 3/2002 |
| WO | WO2003/010510 A2 | 7/2002 |
| WO | WO2003/088817 | 10/2003 |
| WO | WO2005/114094 A1 | 12/2005 |

OTHER PUBLICATIONS

Gerard A. Alphonse, "Design of High-Power Superluminescent Diodes with Low Spectral Modulation," *Proceedings of SPIE*, vol. 4648, pp. 125-138 (2002).

Andrew M. Rollins and Joseph A. Izatt, "Optical Interferometer Designs for Optical Coherence Tomography," *Optics Lett.* vol. 24, No. 21, Nov. 1, 1999, pp. 1484-1486.

Rinat O. Esenaliev, Kirill V. Larin and Irina V. Larina, "Noninvasive Monitoring of Glucose Concentration with Optical Coherence Tomography," *Optics Lett.* vol. 28, No. 13, Jul. 1, 2001, pp. 992-994.

H.C. Casey, Jr. and M.B. Panish, *Heterostructure Lasers Parts A and B*, Academic Press, New York, 1978.

R. W. Waynant, V.M. Chenault, Overview of Non-Invasive Fluid Glucose Measurement Using Optical Techniques to Maintain Glucose Control in Diabetes Mellitus, *LEOS Newsletter*, vol. 12, No. 2, Apr. 1998.

R.J. McNichols, G.L. Cote, Optical Glucose Sensing in Biological Fluids: An Overview, Journal of Biomedical Optics, vol. 5, 2000, pp. 5-16.

Renu Virami, M.D., "Pathology of the Thin-Cap Fibroatheroma: A Type of Vulnerable Plaque," Journal of Interventional Cardiology, vol. 16, No. 3, 2003, pp. 267-272.

S.L. Jacques, Skin Optics, Oregon Medical Laser Center News, Jan. 1998.

J. T. Bruulsema, et al, "Correlation Between Blood Glucose Concentration in Diabetics and Noninvasively Measured Tissue Optical Scattering Coefficient," *Optics Letters*, vol. 22, No. 3, Feb. 1, 1997, pp. 190.

M. Kohl, M. Cope, M. Essenpries, D. Bocker, "Influence of Glucose Concentration on Light Scattering in Tissue-Simulating Phantoms," *Optics Letters*, vol. 19, No. 2, Dec. 15, 1994, pp. 2170.

J. M. Schmidt, S.H. Xiang, K.M. Yung, "Speckle in Optical Coherence Tomography" *J. of Biomedical Optics*, vol. 4, No. 1, Jan. 1999, pp. 95-105.

J. M. Schmitt, G. Kumar, Optical Scattering Properties of Soft Tissue: A Discrete Particle Model, *Applied Optics*, vol. 37, No. 13, May 1, 1998, pp. 2788-2797.

Aristide Dogariu and Gabriel Popsecu, "Measuring the Phase of Spatially Coherent Polychromatic Fields," School of Optics, University of Central Florida, vol. 89, No. 24, Dec. 9, 2002, pp. 1-2.

Valery V. Tuchin, "Light Propagation in Tissues with Controlled Optical Properties," *J. Biomedical Optics* 2(04), 1997, pp. 401-417.

Kirill V. Larin, Massoud Motamedi, Taras V. Ashitkov, and Rinat O. Esenaliev, "Specificity of Noninvasive Blood Glucose Sensing Using Optical Coherence Tomography Technique: A Pilot Study," Physics in Medicine and Biology, Phys. Med. Biol. 48 (2003) pp. 1371-1390.

Sid Bennett and Steven R. Emge, "Fiber Optic Rate Gyro for Land Navigation and Platform Stabilization," Sensors Exp 1994, Cleveland, Ohio, Sep. 20, 1994.

Morteza Naghavi MD, "From Vulnerable Plaque to Vulnerable Patient," *Circulation*, Oct. 7, 2003, pp. 1664-1672.

A. F. Fercher, K. Mengedoht, and W. Werner, "Eye-Length Measurement By Interferometry with Partially Coherent Light," *Optic Letters*, Optical Society of America, vol. 13 No. 3, Mar. 1988, pp. 186-188.

Kazumasa Takada, Itaru Yokohama, Kazumori Chida, and Juichi Noda, "New Measurement System for Fault Location in Optical Waveguide Devices Based on an Interferometric Technique," *Applied Optics*, vol. 26, No. 9., May 1, 1987, pp. 1603-1606.

B.L. Danielson and C.D. Whittenberg, "Guided-wave Reflectometry with Micrometer Resolution," *Applied Optics*, vol. 26, No. 14, Jul. 15, 1987.

Robert C. Youngquist, Sally Carr and D.E.N. Davies, Optical Coherence-Domain Reflectometry: A New Optical Evaluation Technique, *Optics Letters*, vol. 12, No. 3, Mar. 1987.

Renu Virami, "Lessons from Sudden Coronary Death," Arterioscler Thromb Biol., May 2000, pp. 1262-1275.

Aristide Dogariu, "High-Resolution Patial and Spectral Characterization of Optical Fields," Optics & Photonics News, Dec. 2002, pp. 21.

C. Lentner, ed. Geigy Scientific Tables, Ciba-Geigy, Basle, Switzerland, 1984, pp. 69.

Joseph M. Schmitt, "Optical Coherence Tomography (OCT): A Review," *IEEE J. Select Topics in Quant*. Elect. vol. 5, No. 4, Jul./Aug. 1999, pp. 1205-1215.

Akira Ishimaru, "Diffusion of Light in Turbid Material," *Applied Optics*, vol. 28, No. 12, Jun. 15, 1989, pp. 2210-2215.

* cited by examiner $G(\Delta l).\cos(2\pi\Delta l/\lambda_O)$ $G(t).\cos(2\pi f_c t + \phi_c)$

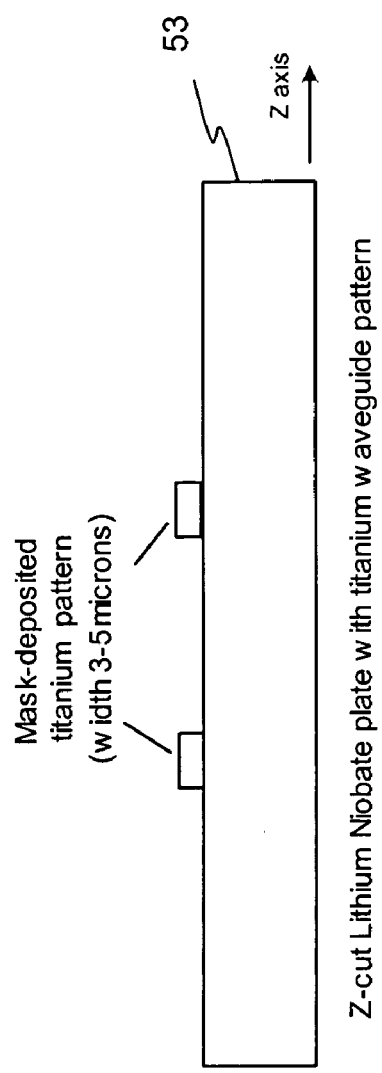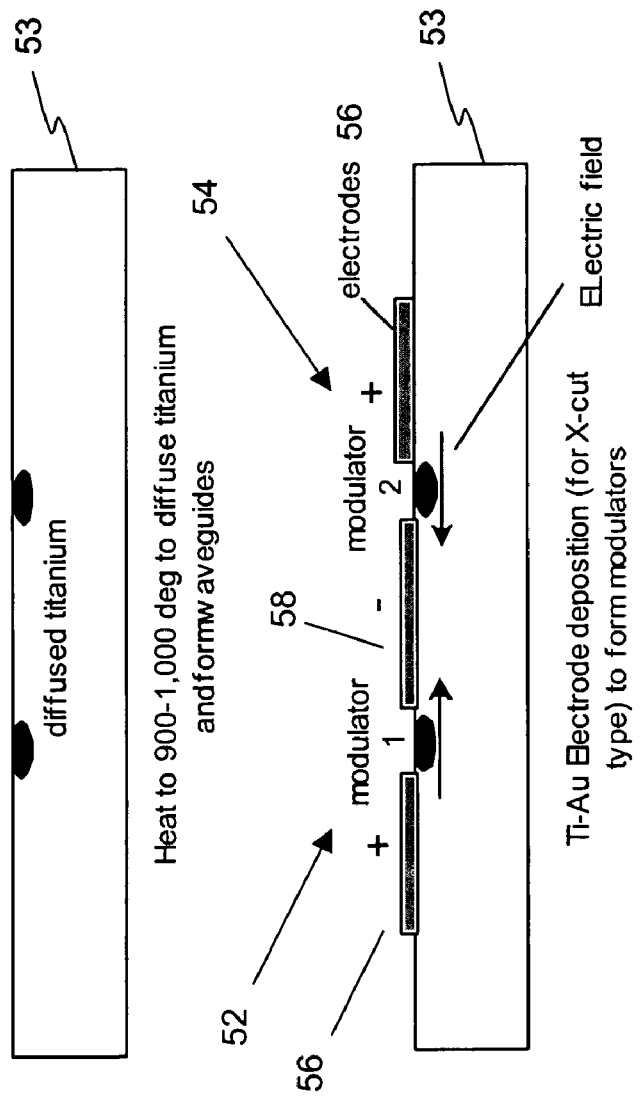

LOW COHERENCE INTERFEROMETRY FOR DETECTING AND CHARACTERIZING PLAQUES

CROSS-REFERENCE TO RELATED APPLICATIONS

This is a continuation-in-part application of U.S. Ser. No. 10/845,849, filed May 14, 2004 the contents of which are incorporated by reference herein in their entirety.

BACKGROUND

The invention concerns a low coherence interferometric (LCI) method for detecting plaques. For example, a method and apparatus for the analysis and detection of atheromas and/or atherosclerotic plaques in arterial walls. More particularly, in one embodiment, a methodology and system for detecting and evaluating vulnerable atherosclerotic plaques in a blood vessel. Further, measurement of the interface between the plaque and lipid pool between the plaque and the artery and measurement the thickness of the plaque with a high accuracy. An application area of interest is that of the diagnosis and management of cardiovascular diseases (CVD).

Coronary Heart Disease (CHD) accounts for approximately fifty percent of the death toll attributed to CVD. Despite major advances in the treatment of coronary heart disease patients, a large number of victims of CHD who are apparently healthy die suddenly without prior symptoms. Available screening and diagnostic methods are insufficient to identify the victims before the catastrophic event occurs. The recognition of the role of the vulnerable plaque has opened new avenues of opportunity in the field of cardiovascular medicine. Vulnerable plaques have been defined as any atherosclerotic plaque with high likelihood of thrombotic complications and rapid progression. Researchers have found that many people who experience heart attacks do not have arteries that have been severely narrowed by plaque. In fact, vulnerable plaque may be buried inside the arterial wall. It has also been found that in these individuals, that vulnerable plaque manifested itself as more than just debris clogging an artery, but that it was filled with different cell types that induce blood clotting. One particularly lethal type of vulnerable plaque is generated through an inflammation process, leading to the formation of a large lipid core inside the artery wall, covered by a thin fibrous cap. When this thin covering over the plaque cracks and bleeds, it spills the contents of the vulnerable plaque into the bloodstream, creating clots large enough to block the artery.

Therefore, there is considerable interest in the identification of plaques prior to the occurrence of thrombosis. Early detection would enhance therapies, while leading to trials of novel preventive measures. Multiple new technologies to improve characterization of plaque in patients are under development. These techniques seek to identify the histologic features, of plaques suspected to represent vulnerability, and provide additional information that heretofore has not been available. Data on structure, composition, deformability, pathophysiology, metabolism, temperature, and the like will enhance characterization. The additional information is key to the accurate detection, characterization and management of vulnerable plaque, with positive outcome for the patients.

Peripheral Vascular Disease (PVD) affects 8 to 12 million Americans and is associated with significant disability and mortality. PVD is a condition in which the arteries that carry blood to the arms or legs become narrowed or clogged. This narrowing or clogging interferes with the normal flow of blood, sometimes causing pain but often exhibiting no symptoms at all. The most common cause of PVD is atherosclerosis, a gradual process in which cholesterol and scar tissue build up, forming a substance called "plaque" that clogs the blood vessels. In some cases, PVD may be caused by blood clots that lodge in the arteries and restrict blood flow. In extreme cases, untreated PVD can lead to gangrene, a serious condition that may require amputation of a leg, foot or toes.

In general, atheromatous or atherosclerotic plaques characteristically comprise a fibrous cap surrounding a central core of extracellular lipids and debris located in the central portion of the thickened vessel intima, which is known as the "atheroma". On the luminal side of the lipid core, the fibrous cap is comprised mainly of connective tissues, typically a dense, fibrous, extracellular matrix made up of collagens, elastins, proteoglycans and other extracellular matrix materials. In the case of arterial plaques the chronically stenotic plaque in which calcified material builds up in the artery to cause occlusion as discussed above may readily be distinguished from the rupture-prone vulnerable plaque, which consists of a thin fibrous cap and a large lipid core in the wall of the artery. The stenotic plaque is easily detected with MRI, ultrasound, and other diagnostic techniques. Once detected, it is opened up using a stent within a catheter.

With an active atheromatous or atherosclerotic plaque, at the edges of the fibrous cap overlying the lipid core comprises the shoulder region and is enriched with macrophages. The macrophages continually phagocytose oxidized LDL through scavenger receptors, which have a high ligand specificity for oxidized LDL. Continuous phagocytosis results in the formation of foam cells, a hallmark of the atherosclerotic plaque. Foam cells, together with the binding of extracellular lipids to collagen fibers and proteoglycans, play an important role in the formation and growth of the lipid-rich atheroma.

Examination of atheromatous/atherosclerotic plaques has revealed substantial variations in the thickness of fibrous caps, the size of the atheromas, the extent of dystrophic calcification, and the relative contribution of major cell types. Atheromatous plaques include a significant population of inflammatory cells, such as monocytes or macrophages and T lymphocytes. The emigration of monocytes into the arterial wall, and their subsequent differentiation into macrophages and ultimately foam cells, remains one of the earliest steps in plaque formation. Once there, these cells play a critical role in secreting substances that further contribute to atherosclerosis.

The causative agent of acute coronary syndrome is fissure, erosion or rupture of a specific kind of atheromatous plaque known as a "vulnerable plaque." It has been determined that vulnerable plaques are responsible for the majority of heart attacks, strokes, and cases of sudden death. A vulnerable plaque is structurally and functionally distinguishable from a stable atheromatous plaque. For example, a vulnerable plaque is characterized by an abundance of inflammatory cells (e.g., macrophages and/or T cells), a large lipid pool, and a thin fibrous cap. Pathologic studies have also provided a further understanding of why vulnerable plaques have a higher propensity for rupture than other atheromatous plaques. The thickness and integrity of the fibrous cap overlying the lipid-rich core is a principal factor in the stability of the plaque. Generally, atheromatous plaques prone to rupture can be characterized as having thinner fibrous areas, increased numbers of inflammatory cells (e.g., macrophages and T cells), and a relative paucity of vascular smooth muscle cells. Vascular smooth muscle cells are the major source of extra cellular matrix production, and therefore, the absence of vascular smooth muscle cells from an atheromatous plaque contributes to the lack of density in its fibrous cap.

While the fibrous tissue within the cap provides structural integrity to the plaque, the interior of the atheroma is soft, weak and highly thrombogenic. It is rich in extracellular lipids and substantially devoid of living cells, but bordered by a rim of lipid-laden macrophages. The lipid core is a highly thrombogenic composition, rich in tissue factor, which is one of the most potent procoagulants known. The lesional macrophages and foam cells produce a variety of procoagulant substances, including tissue factor. The fibrous cap is the only barrier separating the circulation from the lipid core and its powerful coagulation system designed to generate thrombus. Essentially, the rapid release of procoagulants into the blood stream at the site of rupture forms an occlusive clot, inducing acute coronary syndrome. Thus, the thinner the fibrous cap, the greater the instability of the thrombogenic lipid core and the greater the propensity for rupture and thrombosis. Generally, it has been determined that the critical thickness of the cap is of the order of 70 microns.

Common methods of plaque detection include angiography and angioscopy. Except in rare circumstances, angiography gives almost no information about the characteristics of plaque components. However, angiography is only sensitive enough to detect hemodynamically significant lesions (>70% stenosis), which account for approximately 33% of acute coronary syndrome cases. Angioscopy is a technique based on fiber-optic transmission of visible light that provides a small field of view with relatively low resolution for visualization of interior surfaces of plaque and thrombus. Because angioscopic visualization is limited to the surface of the plaque, it is generally insufficient for use in detecting actively forming atheromatous plaques and/or determining vulnerable plaques.

Several methods are being investigated for their ability to identify atheromatous plaques. One such method, intravascular ultrasound ("IVUS") uses miniaturized crystals incorporated at catheter tips and provides real-time, cross-sectional and longitudinal, high-resolution images of the arterial wall with three-dimensional reconstruction capabilities. IVUS can detect thin caps and distinguish regions of intermediate density (e.g., intima that is rich in smooth muscle cells and fibrous tissue) from echolucent regions, but current technology does not determine which echolucent regions are composed of cholesterol pools rather than thrombosis, hemorrhage, or some combination thereof. Moreover, the spatial resolution (i.e., approximately 100 μm) does not distinguish the moderately thinned cap from the high risk cap (i.e., approximately 25–75 μm) and large dense calcium deposits produce acoustic echoes which "shadow" so that deeper plaque is not imaged.

Intravascular thermography is based on the premise that atheromatous plaques with dense macrophage infiltration give off more heat than non-inflamed plaque. The temperature of the plaque is inversely correlated to cap thickness. However, thermography may not provide information about eroded but non-inflamed lesions, vulnerable or otherwise, having a propensity to rupture.

Raman spectroscopy utilizes Raman effect: a basic principle in photonic spectroscopy named after its inventor. Raman effect arises when an incident light excites molecules in a sample, which subsequently scatter the light. While most of this scattered light is at the same wavelength as the incident light, some is scattered at a different wavelength. This shift in the wavelength of the scattered light is called Raman shift. The amount of the wavelength shift and intensity depends on the size, shape, and strength of the molecule. Each molecule has its own distinct "fingerprint" Raman shift. Raman spectroscopy is a very sensitive technique and is capable of reporting an accurate measurement of chemical compounds. Conceivably, the ratio of lipid to proteins, such as collagen and elastin, might help detect vulnerable plaques with large lipid pools. However, it is unlikely that actively forming and/or vulnerable plaques will be reliably differentiated from stable plaques based solely on this ratio.

Radiation-based methods for detection of diseased tissue are also known in the art. Some devices include an ion-implanted silicon radiation detector located at the tip of a probe with a preamplifier contained within the body of the probe, and connected to the detector as well as external electronics for signal handling. Another device provides radio-pharmaceuticals for detecting diseased tissue, such as a cancerous tumor, followed by the use of a probe with one or more ion-implanted silicon detectors at its tip to locate the radio labeled diseased tissue; the detector is preferentially responsive to beta emissions.

Optical coherence tomography ("OCT") measures the intensity of reflected near-infrared light from tissue. OCT is an application of to form 3D images. OCT provides images with high resolutions that are approximately 10 to 20 times higher than that of IVUS, which facilitates detection of a thin fibrous cap. Advantageously, while other methodologies may exhibit the capability to detect the presence of lipids within the vessel wall, OCT techniques have been shown to exhibit the spatial resolution sufficient for resolving the parameters directly responsible for plaque ruptures. Unfortunately, OCT is an imaging technique and, as a result, is computationally intensive and very time consuming. The resulting images from OCT require skilled interpretation for the detection of vulnerable plaques.

Low Coherence Interferometry (LCI) is an optical technique that allows for accurate, analysis of optical interfaces, and is very adaptable to the analysis of the scattering properties of heterogeneous optical media such as layered biological tissue. Furthermore, the interface between two regions in biological tissues exhibiting different optical characteristics is characterized by change in scattering, absorption, and refractive index characteristics. Of particular interest, are sensitive methods to measure the important features of the signal at the discontinuity e.g., such as between a fibrous cap and lipid pool. In LCI, light from a broad bandwidth light source is first split into sample and reference light beams which are both retro-reflected, from a targeted region of the sample and from a reference mirror, respectively, and are subsequently recombined to generate an interference signal having maxima at the locations of constructive interference and minima at the locations of destructive interference. The interference signal is then employed to evaluate the characteristics of the sample. LCI exhibits very high resolution as the detectable interference occurs only if the optical path difference between them is less than the coherence length of the source. LCI can be used in the detection and characterization of blockage sites in peripheral arteries. The LCI interferometer can be made out of optical fibers, and therefore can be easily integrated with catheters used by interventional radiologists to open blood vessels. Unfortunately, current LCI techniques, such as OCT, rely on amplitude measurements of the interferences signal and may lack the high resolution required for accurate detection and characterization of vulnerable plaques.

The term "biological sample" denotes a body fluid or tissue of a living organism. Biological samples are generally optically heterogeneous, that is, they contain a plurality of scattering centers scattering irradiated light. In the case of biological tissue, especially skin tissue, the cell walls and other intra-tissue components form the scattering centers.

In spite of these endeavors, attempts to make available an effective sensor for practical operation to detect vulnerable plaque have thus far, proved inadequate. What is needed in the art is a new approach for LCI-based plaque detection and characterization based on the measurement of the phase of the interferometric signal to facilitate accurate detection and characterization of atheromatic/atherosclerotic plaques and particularly vulnerable plaques.

BRIEF SUMMARY

The above discussed and other drawbacks and deficiencies of the prior art are overcome or alleviated by the measurement system and methodology disclosed herein. Disclosed herein in an exemplary embodiment is a method for determining a characteristic of a biological sample, the method comprising: directing broadband light by means of a sensing light path at the biological sample, the sensing light path having an effective light path length; receiving the broadband light reflected from the biological sample by means of the sensing light path; directing the broadband light by means of a reference light path at a reference reflecting device, the reference light path having an effective light path length; and receiving the broadband light reflected from the reference reflecting device by means of the reference light path. The method also includes: adjusting the effective light path length of at least one of the reference light path and the sensing light path to facilitate an interference of the broadband light reflected from the biological sample corresponding to a first depth in the biological sample and the broadband light reflected from the reference reflecting device; and detecting the broadband light resulting from the interference of the broadband light reflected from the biological sample corresponding to the first depth in the biological sample and the broadband light reflected from the reference reflecting device, to provide an interference signal indicative of the broadband light resulting from the interference. The method also includes: determining a first phase associated with the interference signal indicative of the broadband light resulting from the interference of the broadband light reflected from the biological sample corresponding to the first depth in the biological sample and the broadband light reflected from the reference reflecting device; varying the effective light path lengths of at least one of the reference light path and the sensing light path to define a second depth; determining a second phase associated with the interference signal indicative of the broadband light resulting from the interference of the broadband light reflected from the biological sample corresponding to the second depth in the biological sample and the broadband light reflected from the reference reflecting device; and determining the characteristic of the biological sample from the first phase and the second phase.

Also disclosed herein in an exemplary embodiment is a system for determining a characteristic of tissue in a biological sample, the system comprising: a broadband light source for providing a broadband light; a sensing light path receptive to the broadband light from the broadband light source, the sensing light path configured to direct the broadband light at the biological sample and to receive the broadband light reflected from the biological sample; a reference reflecting device; and a reference light path receptive to the broadband light from the broadband light source, the reference light path configured to direct the broadband light at the reference reflecting device and to receive the broadband light reflected from the reflecting device, the reference light path coupled with the sensing light path to facilitate interference of the broadband light reflected from the biological sample and the broadband light reflected from the reference reflecting device. The system also includes means for adjusting the effective light path length of at least one of the reference light path and the sensing light path to facilitate an interference of the broadband light reflected from the biological sample corresponding to a first depth in the biological sample and the broadband light reflected from the reference reflecting device; a detector receptive to the broadband light resulting from the interference of the broadband light reflected from the biological sample and the broadband light reflected from the reference reflecting device; and means for varying effective light path lengths of at least one of the reference light path and the sensing light path to define a second depth. The system further includes a processor configured to: (1) determine a first phase associated with the broadband light resulting from the interfering of the broadband light reflected from the biological sample and the broadband light reflected from the reference reflecting device based on the first depth; (2) determine a second phase associated with the broadband light resulting from the interference of the broadband light reflected from the biological sample and the broadband light reflected from the reference reflecting device based on a second depth; and (3) determine the characteristic of the biological sample from the first phase and the second phase.

Further disclosed herein in yet another exemplary embodiment is system for determining a characteristic of tissue in a biological sample, the system comprising: means for directing broadband light by means of a sensing light path at the biological sample, the sensing light path having an effective light path length; means for receiving the broadband light reflected from the biological sample by means of the sensing light path; means for directing the broadband light by means of a reference light path at a reference reflecting device, the reference light path having an effective light path length; and means for receiving the broadband light reflected from the reference reflecting device by means of the reference light path. The system also includes: means for adjusting the effective light path length of at least one of the reference light path and the sensing light path to facilitate an interference of the broadband light reflected from the biological sample corresponding to a first depth in the biological sample and the broadband light reflected from the reference reflecting device; and means for detecting the broadband light resulting from the interference of the broadband light reflected from the biological sample corresponding to the first depth in the biological sample and the broadband light reflected from the reference reflecting device, to provide an interference signal indicative of the broadband light resulting from the interference. The system further includes: means for determining a first phase associated with the interference signal indicative of the broadband light resulting from the interference of the broadband light reflected from the biological sample corresponding to the first depth in the biological sample and the broadband light reflected from the reference reflecting device; means for varying the effective light path lengths of at least one of the reference light path and the sensing light path to define a second depth; means for determining a second phase associated with the interference signal indicative of the broadband light resulting from the interference of the broadband light reflected from the biological sample corresponding to the second depth in the biological sample and the broadband light reflected from the reference reflecting device; and means for determining the characteristic of the biological sample from the first phase and the second phase.

Also disclosed herein in yet another exemplary embodiment is a storage medium encoded with a machine-readable computer program code for determining a characteristic of tissue in a biological sample, including instructions for causing a computer to implement the abovementioned method.

Further in yet another exemplary embodiment there is disclosed a computer data signal embodied in a computer readable format for determining a characteristic of tissue in a biological sample, the computer data signal including instructions for causing a computer to implement the abovementioned method.

BRIEF DESCRIPTION OF THE DRAWINGS

These and other features and advantages of the present invention may be best understood by reading the accompanying detailed description of the exemplary embodiments while referring to the accompanying figures wherein like elements are numbered alike in the several figures in which:

FIG. 19A depicts a process for fabricating the splitter-modulator module in accordance with an exemplary embodiment;

FIG. 19B depicts a process of fabricating the splitter-modulator module in accordance with an exemplary embodiment;

FIG. 19C depicts a process of fabricating the splitter-modulator module in accordance with an exemplary embodiment;

DETAILED DESCRIPTION OF AN EXEMPLARY EMBODIMENT

Figure 1:
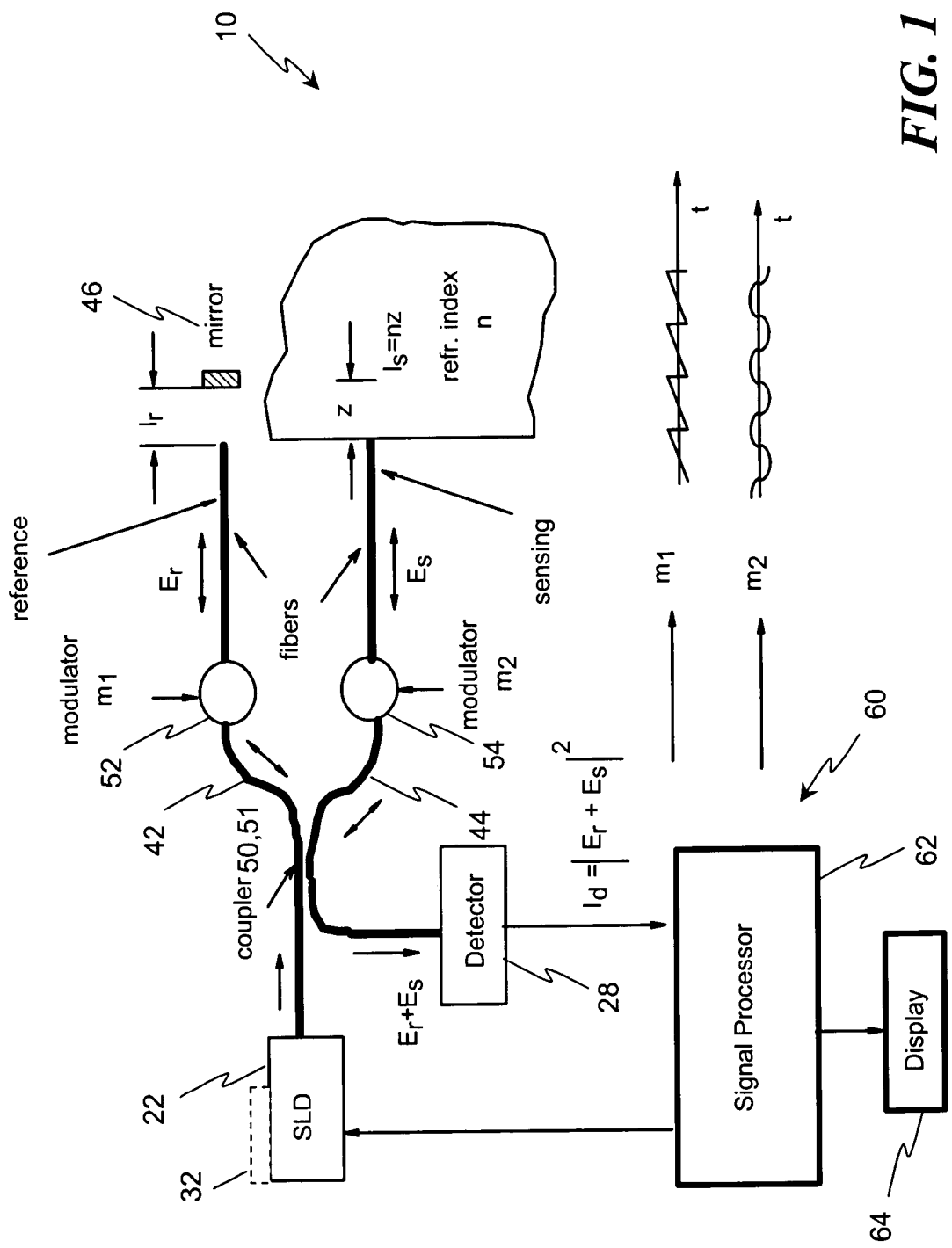
FIG. 1 is a basic all-fiber low-coherence interferometer (LCI)

Disclosed herein, in several exemplary embodiments are high-sensitivity low coherence interferometric (LCI) systems (instruments) for optical metrology, for use in a variety of sensing and monitoring applications, including, but not limited to, trace chemical sensing, optical properties and changes thereof, medical sensing such as detecting and characterizing vulnerable plaques and others. In an exemplary embodiment, the instrument is miniaturized, using integrated optics components such as waveguides, splitters and modulators on a single substrate such as, but not limited to, a $LiNbO_3$ (Lithium Niobate) chip. The exemplary embodiments may also involve the use of a "circulator" type of optical component, including of a polarizing beam splitter and quarterwave plate, which can be combined with the light source and detector into a miniature module that prevents optical feedback into the light source while doubling the detected light. Alternatively, instead of the polarizing beam splitter and quarter wave plate, one or more isolators and a waveguide coupler or devices using Faraday rotation in magneto-optic films may be employed in a similar module to accomplish the same purpose. Disclosed herein in the exemplary embodiments are multiple methodologies and associated systems employed to derive information from the magnitude and/or phase of an interferometric signal for detecting and characterizing vulnerable plaques.

It will be appreciated that while the exemplary embodiments described herein are suitable for the detection and characterization of vulnerable plaques, the embodiments may further be applicable to detection of other lesions such as skin cancer and lesions lining the walls of internal organs such as the esophagus, colon, etc. It may be further appreciated that the methods discussed herein generally permit an absolute measurement of the characteristics of atheromatic/atherosclerotic plaque, such as its thickness, as well as relative measurement from a given baseline for a given medium. Therefore, for relative measurements, calibration to establish a baseline may be required. For instance, for one exemplary embodiment, a calibration strip is employed to facilitate calibration. Other methodologies, such as using a sample of known index of refraction may also be employed.

It should also be noted that the light wavelengths discussed below for such methods may be in the range of about 300 to about several thousand nanometers (nm), that is, in the spectral range from near ultraviolet to near infrared light. In an exemplary embodiment, for the sake of illustration, a wavelength of about 1300 nm is employed. The term "light" as used herein is not to be construed as being limited or restricted to the visible spectral range. However, it should be appreciated that LCI can occur in any interferometric system using broad frequency or wavelength bandwidth.

It will also be noted that for a homogeneously scattering medium for which a specific property such as the refractive index is to be measured, it is sufficient to probe at a single depth, as the desired information can be obtained from the phase of the interferometric signal, presumed to be independent of the amplitude. In this case, an instrument as described herein can be configured for measurement at a single depth. However, in an exemplary embodiment, to probe for inhomogeneities (local changes of absorption, reflection, or refractive index), as would be expected for the several layers of a atheromatic/atherosclerotic plaque the instrument may be configured to measure both the amplitude and the phase of the interferometric signal as functions of depth. Described herein in an exemplary embodiment is a system configured to probe at variable depths and for general imaging purposes, while later embodiments may be employed for measurement at fixed depth. For example, probes at various depths may be employed to identify the various layers and the respective thickness for each layer of an atherosclerotic plaque, while single depth measurements may be employed to ascertain particular characteristics of the medium of a layer, be it the cap, lipid or otherwise.

Finally, it will also be appreciated that while the exemplary embodiments disclosed herein when implemented with an extensible fiber/guidewire and catheter arrangement are described with reference and illustration to detecting and characterizing atheroma and/or atherosclerotic plaques, applications and implementations for determination of other biological constituents or analytes may be understood as being within the scope and breadth of the claims. For example, the embodiments disclosed herein may readily be adapted for invasive or non-invasive applications including, but not limited to detection and evaluation of analytes such as glucose and glucose concentration.

Another important consideration is that, as a tool, particularly for medical diagnostic applications, the LCI system of the exemplary embodiments is preferably configured to be rather small, fiber-optic based, using non-ionizing optical radiation and when implemented with an extensible fiber/guidewire and catheter arrangement facilitates convenient measurements without bulky equipment and apparatus. In addition, the techniques described in the exemplary embodiments provide for characterization of both the tissue structure and biochemistry. Moreover, the exemplary embodiments advantageously provide real-time results with excellent spatial resolution (~10 microns or better), which, for a typical broadband light source at 1,300-nm center wavelength and 60 nm bandwidth, is approximately 10 times better than other techniques such as intravenous ultrasound, MRI, and the like. Furthermore, unlike MRI or computerized tomography, and other imaging methodologies, the techniques of the exemplary embodiments do not require expensive facilities and are relatively inexpensive to manufacture and use. In any case, emphasis is also placed on miniaturization, portability, low power and low cost.

To facilitate appreciation of the various embodiments of the invention reference may be made to FIG. 1, depicting an all-fiber low-coherence interferometer (LCI) system and the mathematical equations developed herein. Referring also to FIGS. 6, 7, 16, and 17, wherein like elements are numbered alike, in an exemplary embodiment, an LCI systems 10, 10$b$ includes, but is not limited to two optical modules: a source-detector module 20$a$ and a splitter-modulator module 40$a$, and associated processing systems 60. The source-detector module 20$a$ including, but not limited to, a broad-band light source 22, such as a super luminescent diode (SLD) denoted hereinafter as source or SLD, attached to a single-mode fiber 23 or waveguide, an isolator 24 configured to ensure that feedback to the broad band light source 22 is maintained at less than a selected threshold. The source-detector module 20$a$ also includes an optical detector 28.

The splitter-modulator module 40$a$ includes, but is not limited to, a waveguide input 41, a waveguide output 43, a splitter/coupler 50, and two waveguide light paths: one light path, which is denoted as the reference arm 42, has adjustable length lr with a reflecting device, also referred to as a mirror 46 at its end; the other light path, which is denoted as the sensing arm 44, allows light to penetrate to a distance z in a medium/object and captures the reflected or scattered light from the medium. It will be appreciated that the captured reflected or scattered light is likely to be only the so-called "ballistic photons", i.e., those that are along the axis of the waveguide. Provision is also made for one or more modulators 52, 54 in each of the reference arm 42 and sensing arm 44 respectively.

Figure 17:
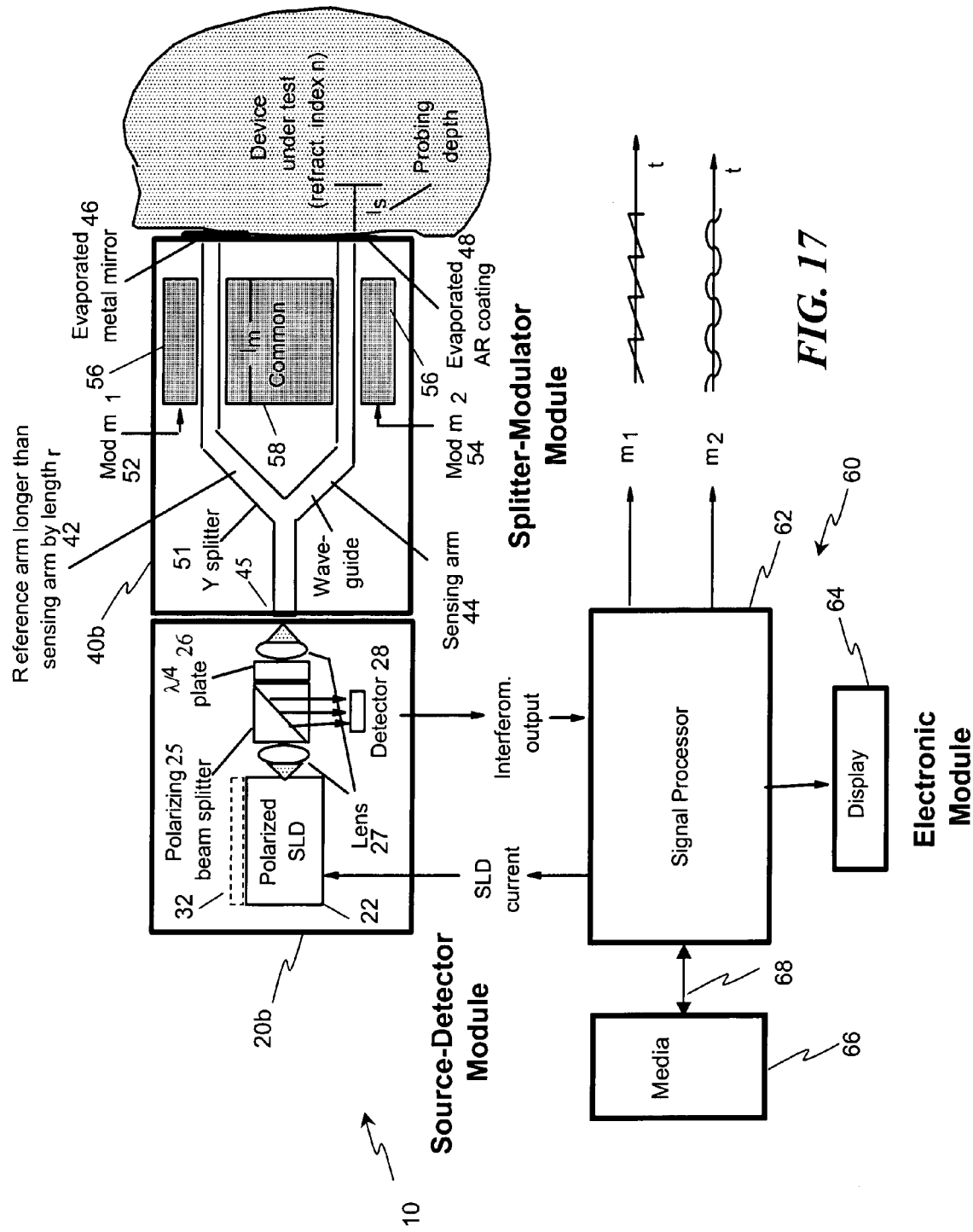
FIG. 17 depicts a configuration of an interferometer system in accordance with an exemplary embodiment of the invention.

Continuing with the Figures, and in particular, FIG. 17, in another exemplary embodiment, the source-detector module 20$b$ includes, but is not limited to, a polarized broad-band light source 22, attached to a single-mode fiber 23. The source-detector module 20$b$ also includes a polarizing beam splitter 25 with an quarter wave plate 26 employed to ensure a selected polarization configured to facilitate ensuring that feedback to the broad band light source 22 is maintained at less than a selected threshold. The source-detector module 20$b$ also includes an optical detector 28.

The splitter-modulator module 40b of this embodiment includes, but is not limited to, a waveguide inputs/output 45, a Y-splitter-combiner 51, and the two waveguide arms: reference arm 42, and sensing arm 44. Once again, provision is also made for one or more modulators 52, 54 in each of the reference arm 42 and sensing arm 44 respectively.

It will be appreciated that while certain components have been described as being in selected modules, e.g., 20, 40 such a configuration is merely illustrative. The various components of the LCI system 10 may readily be distributed in one or more various modules e.g., 20, 40 as suits a given implementation or embodiment. Furthermore, in an exemplary embodiment the waveguide arms 42, 44 and/or fibers 23 are configured for single-transverse-mode transmission, and preferably, but not necessarily, polarization-maintaining waveguides or fibers. Furthermore it will be appreciated that in any of the exemplary embodiments disclosed herein the waveguide and/or fiber tips of each component joined are configured e.g., angled-cleaved in a manner to minimize reflection at the junctions.

In order to perform the prescribed functions and desired processing, as well as the computations therefore (e.g., the computations associated with detecting and utilizing the interference signal, and the like), the LCI system 10, 10b, and more particularly, the processing system 60, may include, but is not limited to a computer system including central processing unit (CPU) 62, display 64, storage 66 and the like. The computer system may include, but not be limited to, a processor(s), computer(s), controller(s), memory, storage, register(s), timing, interrupt(s), communication interface(s), and input/output signal interfaces, and the like, as well as combinations comprising at least one of the foregoing. For example, computer system may include signal input/output for controlling and receiving signals from the source-detector module 20 as described herein. Additional features of a computer system and certain processes executed therein may be disclosed at various points herein.

The processing performed throughout the LCI system 10, 10b may be distributed in a variety of manners as will also be described at a later point herein. For example, distributing the processing performed in one ore more modules and among other processors employed. In addition, processes and data may be transmitted via a communications interface, media and the like to other processors for remote processing, additional processing, storage, and database generation. Such distribution may eliminate the need for any such component or process as described or vice versa, combining distributed processes in a various computer systems. Each of the elements described herein may have additional functionality that will be described in more detail herein as well as include functionality and processing ancillary to the disclosed embodiments. As used herein, signal connections may physically take any form capable of transferring a signal, including, but not limited to, electrical, optical, or radio.

The light reflected from the reference mirror 46 (Electric field $E_r$) in the reference arm 42 and the light reflected or scattered from depth z within the medium or sample (Electric field $E_s$) in the sensing arm 44 are combined at the optical detector 28, whose output current is proportional the combined electric fields. For example, in one instance, the output of the detector 28 is proportional to the squared magnitude of the total electric field $E_t = E_r + E_s$.

The detector current $I_d$ is given by:

$$I_d = \eta |E_r + E_s|^2 = I_r + I_s + i_o(\Delta l) \quad (1)$$

where $\eta$ is the detector quantum efficiency (typically <1), $I_r = \eta E_r E_r^*$ is the detector current due to $E_r$ alone, $I_s = \eta E_s E_s^*$ is the detector current due to $E_s$ alone, and the * represents the complex conjugate. $E_r E_r^*$ and $E_s E_s^*$ represent the optical power in the reflected reference field and reflected sensing field, respectively. The quantity $i_o(\Delta l)$ is the interference or cross-correlation signal between the two optical fields, and is the signal of interest. It is given by:

$$i_o(\Delta l) = 2\sqrt{I_r I_s}\, |G(\Delta l)| \cos \phi_s \quad (2)$$

$$\text{where } |G(\Delta l)| = \exp\left[-\left(\frac{\Delta l}{L_c}\right)^2\right] \text{ and } \phi_s = \frac{2\pi}{\lambda_o} \Delta l,$$

and where $\lambda_o$ is the center wavelength of the light source 22, $\Delta l$ is the optical path difference between the reference and sensing arms, given by:

$$\Delta l = l_r - l_s \text{ where } l_s = nz \quad (3)$$

where $l_r$ is the path length change in the reference arm 42, $l_s$ is the penetration of the sensing light to depth z in the sample, n is the refractive index at the location in the sample, and $L_c$ is the coherence length of the light source and, for a light source having a Gaussian spectrum, it is given by:

$$L_c = \frac{2\sqrt{\ln 2}}{\pi} \frac{\lambda_o^2}{\Delta \lambda} = 0.44 \frac{\lambda_o^2}{\Delta \lambda}. \quad (4)$$

where $\Delta \lambda$ is the FWHM (full width half maximum) linewidth of the light source 22.

Figure 2:
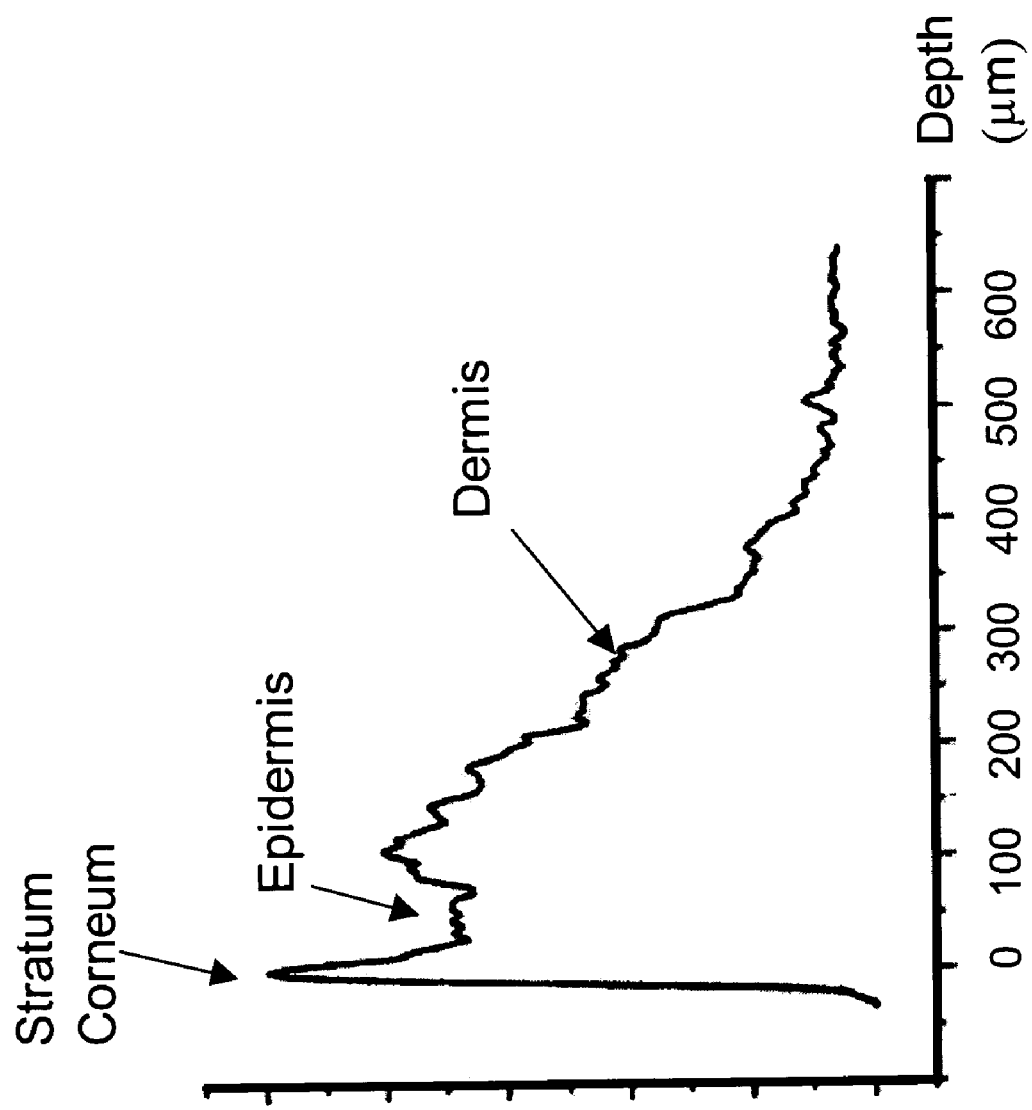
FIG. 2 depicts an illustrative exponential dependence on z for a scattering material such as human tissue as a sample.

It may readily be appreciated that in Equation (1), the square root term represents the magnitude $I_s$ of the LCI signal. It is a function of its starting depth in the sample and the reflection, transmission, and scattering properties of the sample. In particular, if the sample is a scattering material such as human tissue, theory shows $I_s$ to have an exponential dependence on z, as illustrated in FIG. 2 for a skin sample. This type of profile is predicted by scattering theory in general. The specific profile depends on the type of medium or tissue being examined. One of the main features of LCI as applied to scattering tissues is to experimentally obtain this profile for arbitrary tissues, whether skin for determining features such as glucose concentration, or arterial walls for the detection and characterization of vulnerable plaques.

Figure 3A:
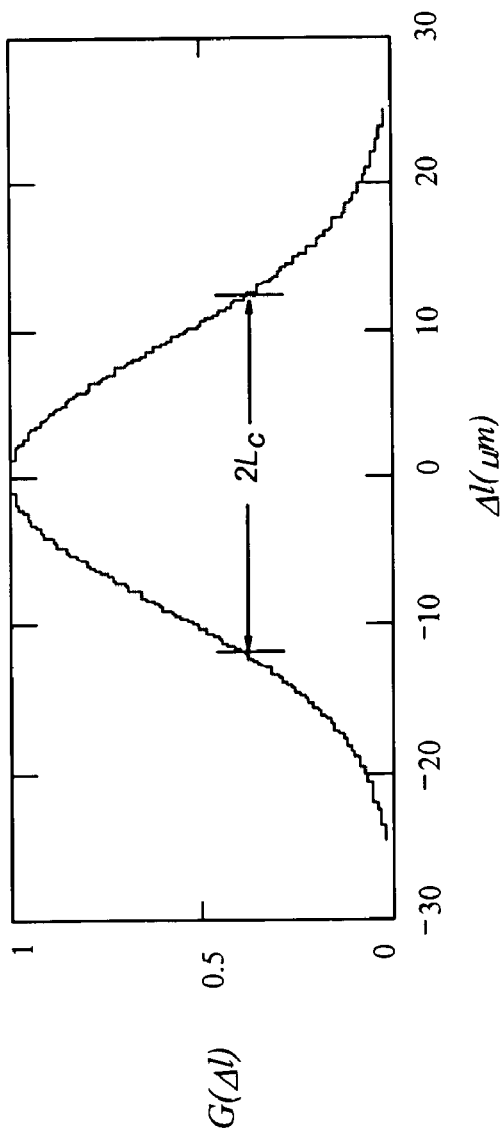
FIG. 3A depicts a plot of an illustrative envelope function $G(\Delta l$.
Figure 3B:
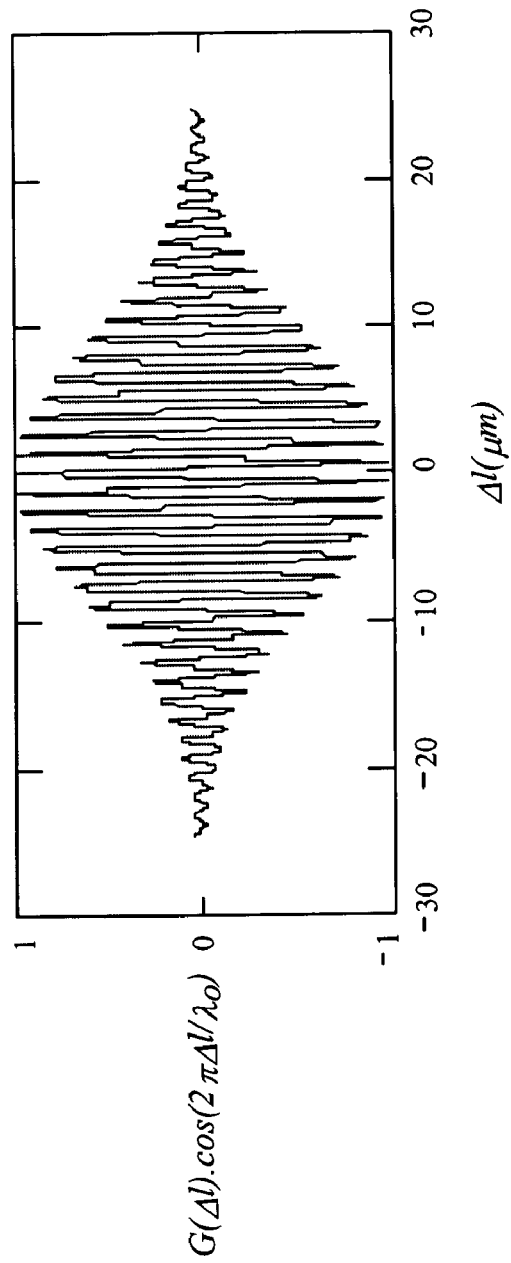
FIG. 3B depicts a plot of an illustrative interference signal $G(\Delta l)\cos \phi_s$.
Figure 4B:
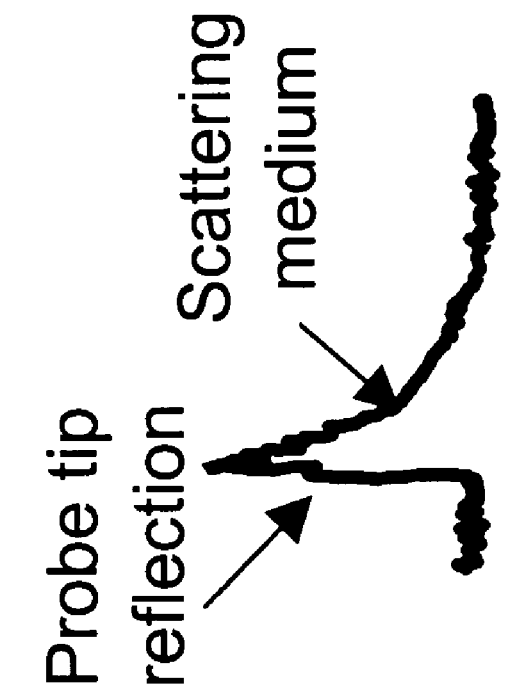
FIG. 4B depicts an illustrative exponential decay for a homogeneous scattering sample with the probe tip immersed in the sample.
Figure 4A:
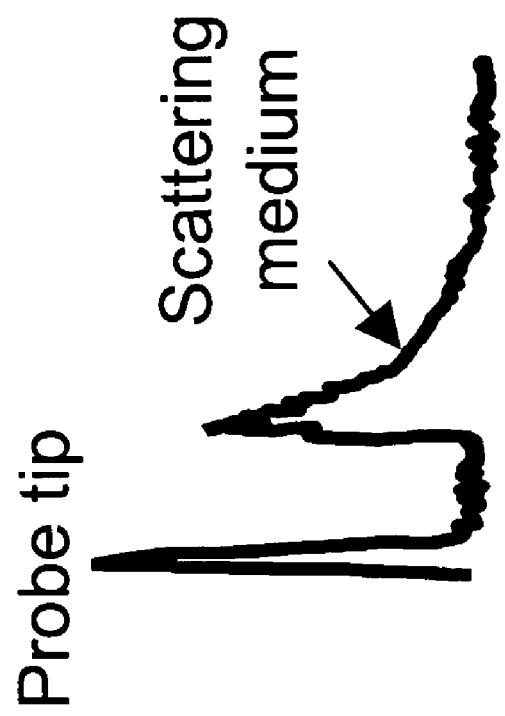
FIG. 4A depicts an illustrative exponential decay for a homogeneous scattering sample with space between the probe tip and the sample.

A plot of the envelope (gating) function $G(\Delta l)$ and of the interference signal $G(\Delta l)\cos \phi_s$ is shown in FIGS. 3A and 3B respectively, for an interferometer with a light source 22 having center wavelength $\lambda_o = 1.3$ μm and FWHM bandwidth $\Delta \lambda = 60$ nm (coherence length $L_c = 12.4$ μm). In FIG. 3A, the detected interference signal exhibits a maximum when the interferometer is balanced, i.e., when the path difference $\Delta l = 0$. As the system 10 becomes increasingly unbalanced, e.g., $\Delta l \neq 0$, the interference signal exhibits maxima and minima of decreasing amplitude over a range determined by $\Delta l$. The cosine term is the real interference. It undergoes maxima and minima and has a $2\pi$ or 360 deg phase shift every time $\Delta l$ changes over a distance equal to the center wavelength of the light. A plot of $G(\Delta l)\cos \phi_s$ is shown in FIG. 3B for an interferometer with the 1,310 nm light source.

It will be appreciated that the interference signal $i_o$ exhibits significant amplitude only over a spatial window of approximately twice the coherence length $L_c$. As the optical bandwidth increases, the coherence length $L_c$ decreases and the spatial measurement window narrows. The existence of this gating function highlights the ability of LCI to resolve depth or optical path length. It means that, out of all the possible sensing light components that are captured by or back-scattered to the sensing fiber in the interferometer, the only component that contributes to the LCI signal is that for which the reference arm length corresponds to a depth in the sample for which the interferometer is balanced, with a resolution corresponding to the coherence length. All other signals outside of the coherence length remain as parts of the dc current $I_s$. As the reference arm length is changed to a new value, the LCI signal obtained is one that corresponds to a new depth in the sample. By scanning the length of the reference arm over a given distance, then the measurement of the peak of the gating function gives the amplitude of the profile of the LCI signal as a function of depth. Thus, LCI provides a means for probing objects at precisely defined locations within the object. Furthermore, it will be appreciated that it may be highly desirable to perform a "quick" depth scan employing larger steps in depth to identify approximately the locations of targets of interest and then a second higher resolution scan particularly in the areas of interest e.g. around depths where a medium change is suspected. Such an approach saves time and processing complexity over employing a high-resolution scan alone throughout the entire depth profile of interest.

It is noteworthy to appreciate that the phase, $\phi_s$, (Equations (2), (5)) of the interference signal $i_o$ changes by $2\pi$ (from a maximum to a minimum then to another maximum) as $\Delta l$ varies from 0 to $\lambda_o$. Therefore, a small change in $\Delta l$ results in a large phase change. It will be further appreciated that the phase of the interference signal $i_o$ is highly sensitive to small changes of optical properties of the mediums, such as refractive indices, or depth z. Thus, while moderate to large changes may readily be observed by measuring the magnitude of the envelope $G(\Delta l)$, small changes are best detected by measuring the phase $\phi_s$ of the interference signal $i_o$. It will be further appreciated that, for certain applications, all the desired information is contained in the range from 0 to $2\pi$. For values of $\Delta l > \lambda_o$, the interference signal $i_o$ is repetitive. Thus, in such applications, the range from 0 to $2\pi$ as indicated in FIG. 3 is a range for which the desired information can be measured without ambiguity. It may also be noted however, that if the coherence length $L_c$ is short enough that the amplitude difference between the main peak and secondary peaks is measurable, or if a means is provided to record a particular point of the interference signal, then phase measurement beyond $2\pi$ may be realized by counting the fringes (the number of equivalent points traversed) starting from that point.

Therefore, it will readily be appreciated that there are two types of information, which can be derived from the interference signal $i_o$: the envelope $G(\Delta l)$, or its peak $G(\Delta l=0)$, which may represent scattering, reflection, and absorption; and the more sensitive changes in $\cos\phi_s$ due to small optical property changes in the specimen under study. In order to make any such measurements, it is first preferable to separate the DC components $I_r$ and $I_s$ from $G(\Delta l)$ and $\cos\phi_s$ in the interferometric signal $i_o$ described in Equation (5).

Figure 16:
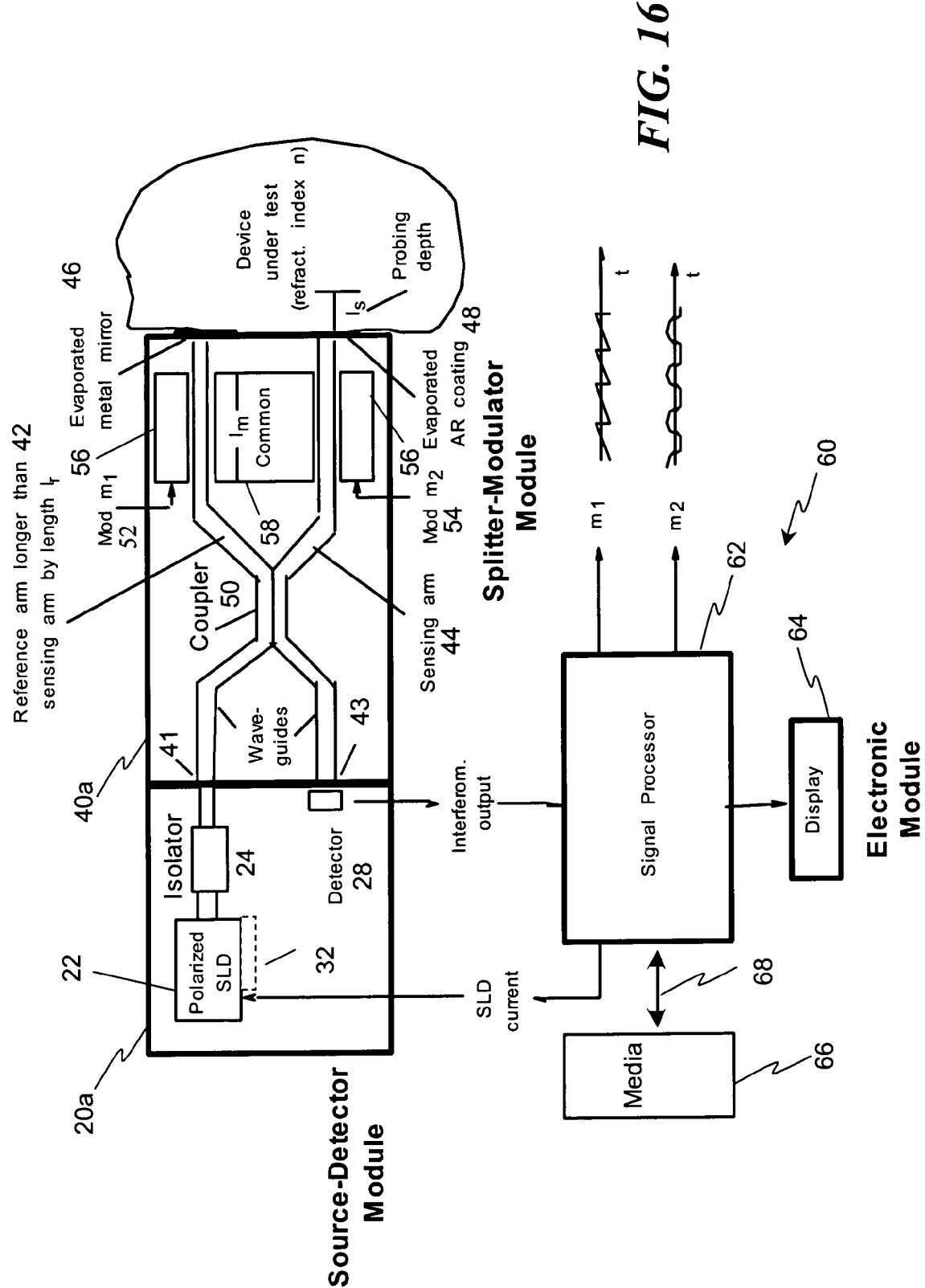
FIG. 16 depicts a minimum configuration interferometer system in accordance with an exemplary embodiment of the invention.

An LCI instrument is designed to measure the peak of the gating function as the reference arm 42 is scanned. This is done by rectifying the interference signal $i_o$ to obtain the envelope $G(\Delta l)$ and using a peak detector the obtain the value corresponding to $\Delta l=0$, which is the peak of the LCI signal. Every type of sample exhibits its own distinct trace signature or profile. For example, in the profile of the skin sample depicted in FIG. 3, the portions that correspond to the stratum corneum, the epidermis, and the dermis may readily be observed. A homogeneously scattering sample, such as milk or a solution containing microspheres in suspension would show a uniform exponential decay as shown in FIG. 16. In FIG. 16 there is a space between the tip of the interferometer probe and the homogeneously scattering sample. In FIG. 17, the probe is immersed in the fluid, so the signals from the probe tip and the beginning of the scattering profile coincide.

Figure 5B:
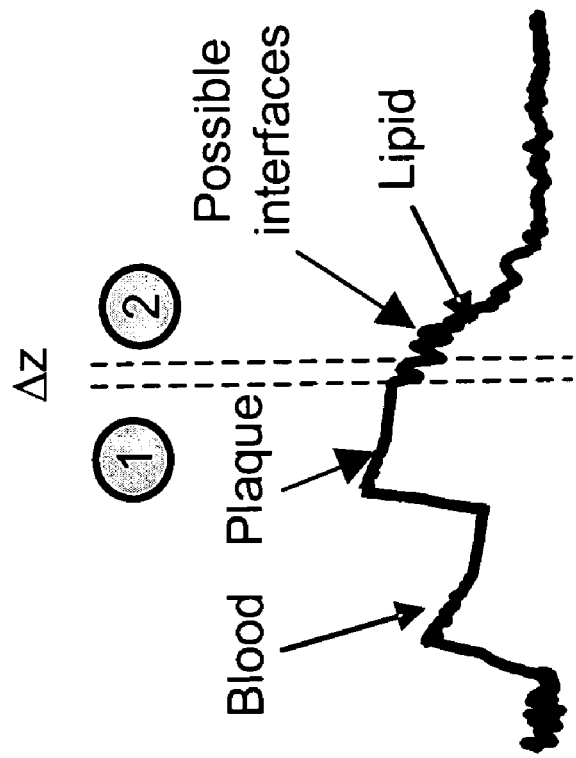
FIG. 5B depicts a representation of an LCI signal for a calcified plaque on an arterial wall with a lipid pool between the plaque and the arterial wall, looking through blood.
Figure 5A:
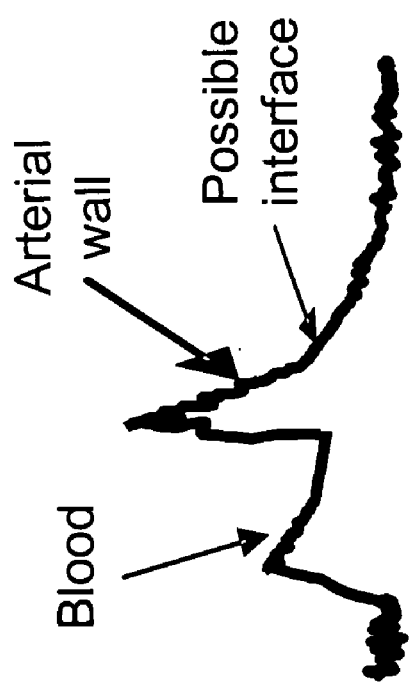
FIG. 5A depicts an example of an LCI profile based on observations of the walls of arteries through flowing blood.

When a medium contains several components, each component may have a different scattering coefficient, refractive index, and/or absorption coefficient. A change in the profile will occur at each interface, depending on the value of these parameters on each side of the interface. When the two media have significantly different scattering characteristics, the profile may exhibit a measurable amplitude step. FIG. 5 depicts an example of LCI profile based on observations of the walls of arteries through flowing blood. FIG. 5A depicts an LCI profile of an arterial wall in a set-up containing blood between the probe tip and the arterial wall simulated by a sheet of rubber. The blood is a scattering medium, and the left portion of the profile is based on the blood, while the arterial wall (rubber sheet) is more highly scattering than the blood and therefore the profile exhibits higher relative amplitude LCI. To the extent that enough light has penetrated through the blood to produce a measurable LCI for the rubber, one sees a larger LCI for the rubber, as indicated by the step in the sketch. FIG. 5B represents the LCI signal for a calcified plaque on an arterial wall with a lipid pool between the plaque and the arterial wall, looking through blood. In the profile depicted, the step increase due to the higher scattering coefficient of the plaque and a step decrease resultant from the lower scattering of the lipid pool may readily be observed. It will be appreciated that by then measuring from the beginning of the hump or step corresponding to the plaque to the beginning of the portion of the signal corresponding to the lipid pool, a measure of the thickness of the plaque cap may be ascertained.

The accuracy of such a measurement is determined by the accuracy with which the transition can be detected. In this example, the transition from the calcified plaque cap to lipid pool. Unfortunately, the transition may not be easily detected, with sufficient accuracy, by looking at only the amplitude of the interferometric signal $i_o$. Moreover, there may be subtle changes due to some possible other interfaces that cannot be readily measurable from the amplitude information alone. In the various exemplary embodiments described herein, it is established that such changes may be detected from the phase information in the LCI signal. In fact, any change in material property, whether it is refractive index, absorption, scattering (which can be treated as a change of absorption or reflection) will affect the phase of the interferometric signal $i_o$. If the change is abrupt at a given location, it will also translate into an abrupt phase shift in the signal at that location. Such abrupt changes can occur at the boundaries between two regions in a sample having different optical properties: refractive index, absorption, scattering, and so on. For example, as a depth scan is conducted the phase of the interferometric signal is expected to vary by a predictable amount for a given medium. When a different medium is encountered exhibiting different scattering properties a significant change in the properties beyond that expected for the previous medium will be encountered. Therefore, the thickness of the various layers of a vulnerable plaque may be ascertained by observing such changes in a layered structure and recording their positions. In one exemplary embodiment abrupt variations in phase and or index of refraction the order of about 0.1% per micron of scan distance are considered as likely changes in medium.

A calculation of the high sensitivity of the phase measurement can be shown for the simple case of only a small refractive index change in the transition from one medium (medium 1 in FIG. 5B) to another (medium 2 in FIG. 5B) over a small distance $\Delta z$. From Equation 3, the phase angle $\phi_s$ of the LCI signal, for a depth in the sample determined by $l_r$ for an interface at depth nz (which is $l_s$) is written as:

$$\phi_s = \frac{2\pi}{\lambda_o}\Delta l = \frac{2\pi}{\lambda_o}(l_r - nz). \tag{5}$$

In the transition from medium 1 to medium 2, a small change in nz, represented by $\Delta nz = n\Delta z + z\Delta n$, where $\Delta n = n_2 - n_1$, results in the phase change:

$$\Delta\phi_s = \frac{2\pi}{\lambda_o}(n_1\Delta z + z\Delta n). \tag{6}$$

For example, consider the transition from a plaque having a refractive index $n_1$ of 1.32 at a depth z of 50 microns to a lipid pool having refractive index $n_2$ of 1.319, over a transition distance $\Delta z$ of 0.5 microns. The reflection coefficient between the two regions, $R=(n_2-n_1)^2/(n_2+n_1)^2=(0.001/2.64)^2=1.43\times10^{-7}$, is too small to be detected in an amplitude measurement. However, a calculation of $\Delta\phi_s$ from these values indicates a phase change of 3.43 radians or 196 degrees for this condition, which is large and may readily be detected. One or more of the exemplary embodiments disclosed herein can easily detect a phase change of such magnitude. This approach makes it possible to observe phase changes discontinuities over a small fraction of wavelength. Thus, while amplitude measurements have a resolution of the order of the coherence length $L_c$, phase measurements provide a resolution of the order of a fraction of a wavelength $\lambda_0$. Advantageously, in applications such as the detection of vulnerable plaques in human arteries, the combination of amplitude change (when available) and phase change can thus provide resolution far exceeding that of amplitude measurements alone. In one or more exemplary embodiments, resolutions of the order of a fraction of a micron are achievable.

Another advantage to employing phase measurements of the LCI signal for detection of vulnerable plaques is that this large phase change occurs regardless of the amplitude of the envelope of the LCI signal, whether the signal is from a location near the surface of the sample or it is from a larger depth where the signal is much weaker due to scattering. This observation is especially significant with the study of vulnerable plaques in human arteries in the presence of blood. Scattering resultant from blood is significant and may reduce the optical signal strength by more than 20 dB before it reaches the arterial walls. Additionally, the light is further scattered by the tissues themselves. A phase measurement approach, permits measurement of plaque thickness with high accuracy, even when the signal strength; is highly reduced due to scattering through blood.

Amplitude changes, in addition to the phase change can be observed when there are large changes in material properties as a result of reflection and additional phase shifts. Reflection causes a fraction $\Gamma$ (the reflection coefficient at the boundary) of the light incident at a boundary to be reflected back to the source. In general, the reflection coefficient at a boundary between a first medium and a second medium having complex indices $n_1+ik_1$ and $n_2+ik_2$, respectively, where n is the real refractive index, k is the extinction coefficient and i the imaginary symbol ($i^2=-1$) and is of the form:

$$\Gamma = \frac{(n_2-n_1)+i(k_2-k_1)}{(n_2+n_1)+i(k_2+k_1)} = \Gamma_m e^{i\phi_m} \tag{7}$$

The extinction coefficient k is related to the absorption coefficient $\alpha$ by the relation $k=\alpha\lambda_o/2\pi$. For the sake of this analysis, the scattering coefficient $\mu$ can be considered analogous to the absorption coefficient, since they affect the exponential decay of the LCI signal in similar ways. This adds a term $\Gamma_m E_s e^{i\Phi_m}$ to the expression for the electric field E at the boundary between the two regions. Since the two media may have different scattering properties, the component of the LCI due to the scattering from the first medium may be identified as $S_1$ with respect to the incident electric field $E_i$ or its related optical power $I_i$. Similarly, the scattering component related to the second media may be identified as $S_2\Gamma$, where $S_2$ may be larger or smaller than $S_1$. Unfortunately, a direct solution for the interferometric signal is very complicated requiring a solution of Maxwell's equations together with the scattering equations. However, advantageously, in view of the above discussion, an empirical phenomenological approximation for the complete interferometric signal at the interface, including the scattering and absorption effects, can be written as:

$$i_o(\Delta l) = 2\sqrt{I_r S_1 I_i}\,|G(\Delta l)|\left[\cos(\phi_s+\Delta\phi_s) + \frac{S_2\Gamma_m}{S_1}\cos(\phi_s+\phi_m)\right] \tag{8}$$

Application of some algebraic manipulation facilitates reduction this signal to the simpler form $$i_o(\Delta l) = 2D\sqrt{I_r S_1 I_i}\,|G(\Delta l)|\cos(\phi_s+\zeta) \tag{9}$$

where D is a new constant and $\zeta$ is the total phase shift. However, it should be appreciated that this derivation is not necessary to illustrate the results. It suffices to note that for the same small values of $\Delta n$ discussed above and for small values of $\Delta k$ (i.e., $k_2-k_1$), $\Delta\phi_s$ remains large at ~196 degrees whereas both the amplitude step $S_2\Gamma_m/S_1$ and the extra phase component $\phi_m$, or $\zeta$ are negligibly small. However, for $k_1=10\,k_2$ (transition from a medium with large scattering to one with low scattering, then $S_2\Gamma_m/S_1\sim1.9$ (a measurable increase) and the additional phase shift $\phi_m$ is ~36 degrees, also measurable. Nevertheless, advantageously, $\Delta\phi_2$ remains the largest measurable change.

Various methodologies and systems have been disclosed for the detection of the amplitude and phase information in LCI signals. For example, commonly assigned U.S. patent application Ser. No. 10/845,849, filed May 14, 2004 by Alphonse discloses a method and apparatus for a method for low coherence interferometry of a biological sample, using phase. Disclosed herein in several exemplary embodiments, there are disclosed methodologies and systems for the detection of both the amplitude and the phase of the LCI information for the detection of vulnerable plaque, preferably employing the phase information in the interferometric signal. A first embodiment employs a Michelson interferometer, while another employs an autocorrelator, each implementation yielding similar results.

Figure 6:
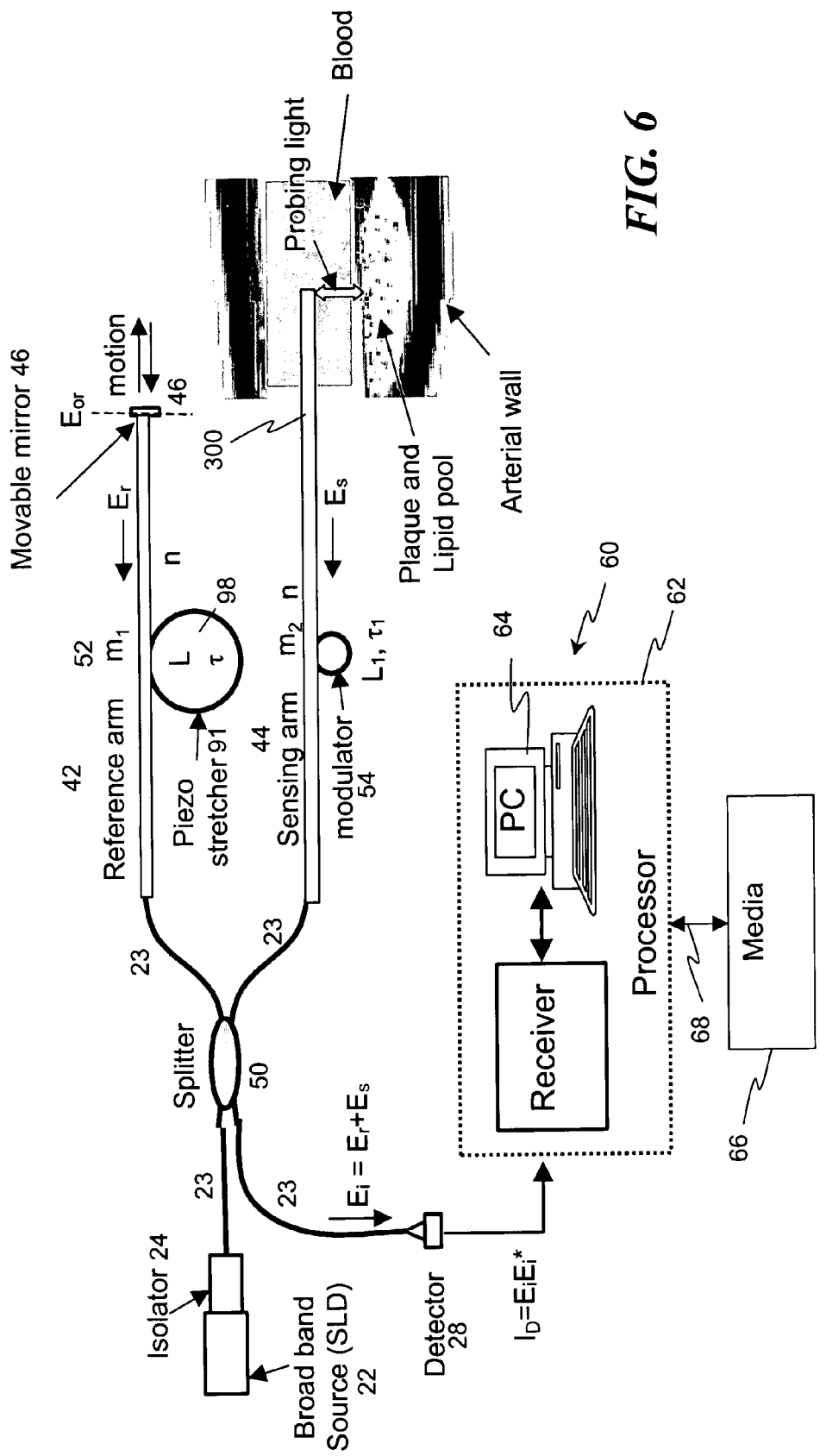
FIG. 6 depicts a system for detecting and characterizing vulnerable plaque in accordance with an exemplary embodiment.

FIG. 6 depicts system for detecting and characterizing vulnerable plaque in accordance with an exemplary embodiment. In one embodiment a Michelson interferometer similar to the interferometer of FIG. 1, is employed, but also including a fiber-sensing probe 300 designed such that it can fit inside a catheter 304 to facilitate directing probing light toward the arterial walls. Furthermore, provision is made for allowing the length of the reference arm 42 to vary as needed. One way to change the length of the reference arm is by using a moving mirror 46 such that the length of the air gap due to the mirror displacement provides the desirable length adjustment for matching a specific depth in the sample. When the length of the adjustment desired is sufficiently small, the mechanical motion of a movable reflecting device 46, e.g., mirror can be replaced by a cable fiber stretcher 91 applied to a length of fiber optic cable 23. In an exemplary embodiment, the cable stretcher 91 may be implemented by wrapping a portion of fiber 23 in the reference arm 42 around a PZT drum 98 and applying a voltage between the inner and outer wall of the drum 98. In the case of plaque detection, displacement of 5 to 6 millimeters is sufficient to facilitate the profiling required to characterize plaque in a blood vessel. This displacement may readily be achieved and scanned by applying a voltage ramp of 500–600 volts to a 20–30 millimeters (mm) diameter PZT drum 98 with a few meters length of fiber wound around it. For longer displacement, a longer length of fiber 94 or a higher voltage can be used, up to the strain limit of the fiber, or one or more individual fiber stretchers 91 can be used in tandem. Logically, a longer, but smaller diameter drum may also be used to achieve the desired displacements based on a selected length of fiber 23.

Figure 7:
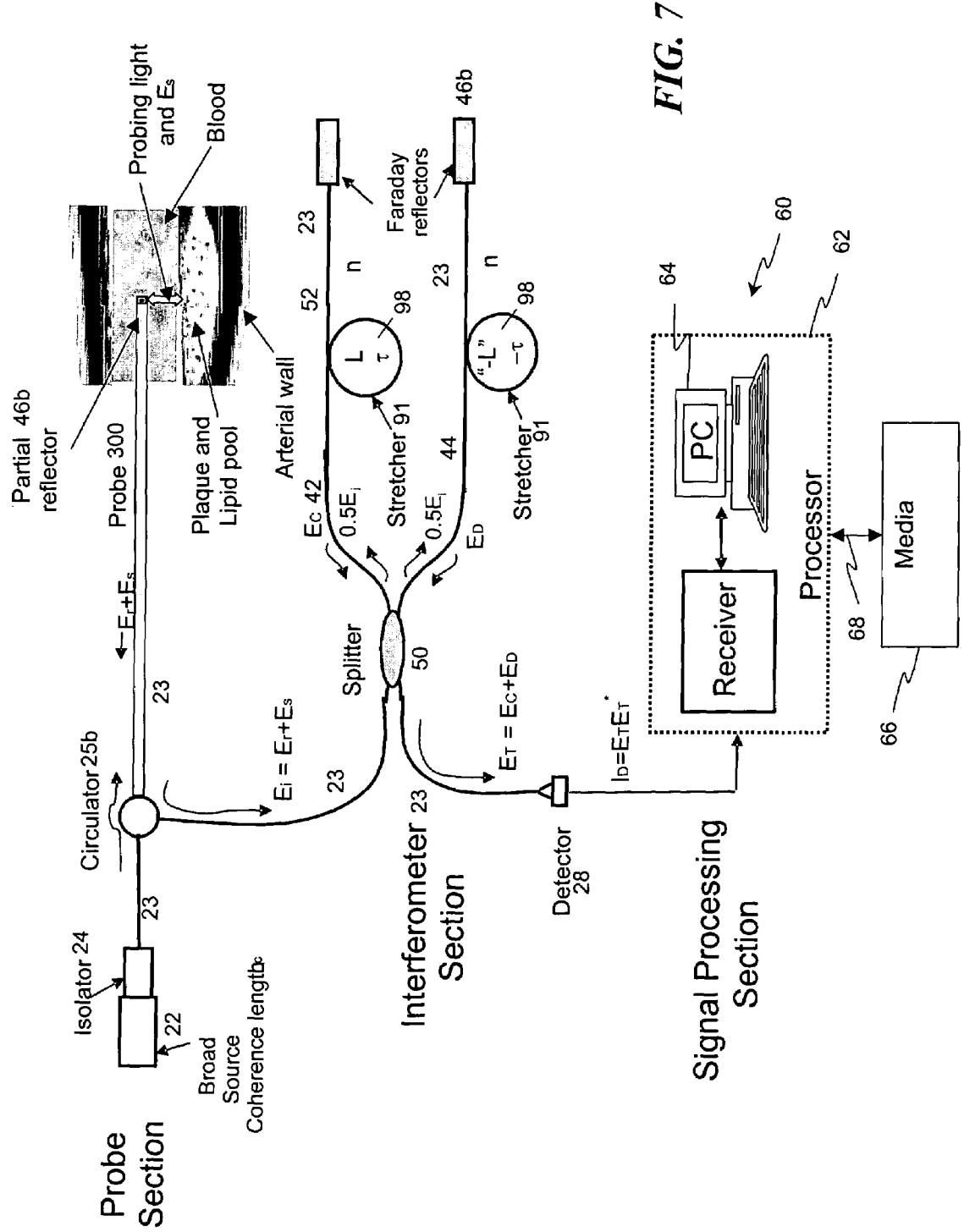
FIG. 7 depicts another system for detecting and characterizing vulnerable plaque in accordance with another exemplary embodiment.

Also disclosed herein in another exemplary embodiment is another system implementation for detecting plaque. FIG. 7 depicts a LCI system 10b utilizing an autocorrelator in accordance with an exemplary embodiment. The autocorrelator-based LCI system 10b includes three sections. First, an independent probe 300, which in this instance includes a fiber 23, which carries both the reference light and the sensing light. A partial mirror 46b is employed at the tip of the fiber 23 from which part of the light can be reflected and part transmitted is employed. The partially reflected light is denoted and used as the reference light, while the light that is transmitted beyond the partial mirror 46 toward the sample and back-scattered into the fiber 23 is denoted and used as the sensing light. For certain applications, the ideal reflection for the reference light from the partial mirror 46 is about 33%. However, when the sensing light is very small e.g., there is little back-scattered light, then it is preferable to make the reflection as low as possible, perhaps less than 1 percent, to prevent detector saturation by the reference light and maintain sufficient signal to noise ratio (SNR) in the detector 28. Furthermore, this approach prevents the shot noise at the detector 28 from overpowering the detected interference signal. In another exemplary embodiment, rather than employing a reference mirror 46, it may also be advantageous to coat the fiber probe 300 tip with an antireflection layer and even use the light reflected from the front surface of the object (plaque) as the reference light. It should be noted that there is a distinct delay between the reference and sensing light. The delay being twice the distance the light travels beyond the fiber tip and into the sample (the distance through blood plus the penetration depth into sample). This distance is expected to be significantly larger than the coherence length of the light source 22, and therefore the reference and object light cannot interfere with each other as described earlier. Thus, to compensate for this difference a path length an interferometer section in this LCI system 10b provides the correction or compensation.

Continuing with FIG. 7, the probe 300 is connected to the broadband source 22 by means of a circulator 25b via an optional isolator 24. As employed in an exemplary embodiment, a circulator 25b is a three-port device in which, light injected at one port is transmitted to a second port, but the light reflected from the second port is deflected to a third port (similarly, an isolator together with a splitter (similar to 25 of another embodiment) may also be used, but the circulator 25b is more efficient). The electric field of the reference light is designated as $E_r$, starting from the value $E_{or}$, (not shown) at the reflector 46b. The field from the sensing light is designated as $E_s$, and its initial value is $E_{os}$ from within the sample (not shown). The total electric field in the probe, which is the sum of $E_r$ and $E_s$ is directed to the interferometer section from the third port of the circulator. This light serves as the input to the interferometer.

It should be appreciated that, in an embodiment using the interferometer, as depicted in FIG. 6, it may be preferred for an exemplary embodiment to employ polarization-maintaining (PM) fiber. In the autocorrelator embodiment, as depicted in FIG. 7, one advantage of having the reference and sensing lights in the same fiber is that ordinary single-mode (SM) fibers may be used instead of polarization maintaining (PM) fibers for the optical system by virtue of the fact that the relative polarization between the reference light and sensing light is always maintained automatically. For an interferometer using standard SM fibers, this would not be the case because such fibers are susceptible to polarization fluctuations caused by birefringence, handling, temperature variations, and other environmental conditions. Maintaining polarization ensures accurate interference between the reference and sensing lights.

The interferometer section of the LCI system 10b includes two arms denoted here 42b and 44b for consistency with a means to provide a variable relative delay between them. The delay may be attained by mechanical means, such as a moving reflector denoted 46b at the end of one arm, for example arm 42b. A preferred means is to achieve a delay is to avoid moving apparatus associated with moving mirrors and utilize an electrically activated fiber-stretching device such as cable stretcher 91 described above. Once again, in an exemplary embodiment, a stretching device 91 may be implemented by winding a length of the fiber 23 in each arm 42b, 44b around a PZT drum 98 and applying a voltage to the PZT drum 98. The application of a voltage of one polarity expands the drum, hence stresses the fiber 23 to increase its length by the amount L and provide a delay τ. If a bias voltage is previously applied to the PZT or if the fiber 23 is wound under tension, then applying the reverse polarity will have the opposite effect. By applying a voltage of one polarity to one drum 98 and of the opposite polarity to another drum 98, one can get a round trip effective path difference of 4L or a delay of 4τ. As mentioned earlier, in an exemplary embodiment, a 15-meter length of fiber wound around a 20–30 mm PZT drum provides a length nL of 5–10 mm, with the application of a peak voltage of about 500 volts in a 50-millisecond ramp. For delays in the 5–20 mm range, it is acceptable for the physical lengths of the fiber arms 42b, 52b to be the same and for the desired delay to be provided only by the PZT stretchers 91, without the slower mechanical displacement. Similar to the probe, as described above, when the interferometer is made from single-mode fibers, it is preferable to maintain the same polarization relationship between its two arms. Furthermore, to avoid the possibility of polarization changes upon reflection, Faraday rotator reflectors denoted 46b are used on each of the two arms 42b and 44b at the ends of the in the interferometer.

Considering now the operation, of interferometer portion of the LCI system 10b. As depicted in the figure, the interferometer input light $E_i=E_r+E_s$ is fed to the interferometer from the circulator 23. A splitter/coupler 50 is employed to split the input light $E_i$ into two substantially equal components, which are transmitted to, and reflected back from the Faraday mirrors 46b. The returning lights denoted $E_C$ and $E_D$, with their respective delays are combined in splitter coupler 50 and transmitted to the detector 28. Therefore, the total light input to the detector is $E_T=E_C+E_D$. Mathematical analysis of this system shows the usual DC terms, some cross-product terms with delays that are always much larger than $L_c$ (the coherence length) and therefore are vanishing and do not contribute to the interferometric signal, and two terms which combine to give the current $i_s(z)$ $$i_s(z) = (1-R)\sqrt{R}\sqrt{I_r I_s(z)}\exp\left[-\left(\frac{\Delta}{L_c}\right)^2\right]\cos\left(\frac{2\pi\Delta}{\lambda_o}\right) \quad (10)$$

where R is the power reflection coefficient at the probe tip, and where $$\Delta = 4nL - 2(n_s z) \quad (11)$$

This result is the same as for the ordinary LCI system with a Michelson interferometer except for the fact that $\Delta$ is double the difference between the scan length and the excess path length between the reference light and sensing light. It can be seen that by adjusting L, $\Delta$ can be brought to zero, thereby, the common optical path between the reference and sensing signal cancels out. Thus, although the optical path difference between the reference and sensing lights is much larger than the coherence length, $L_c$ the interferometer path difference L facilitates compensation for this difference to bring the interference signal under the coherence gating function. In particular, the peak of the signal corresponding to any depth z within the sample is obtained when $2nL=n_s z$. Any of the various means for adjusting an optical path length may be employed to adjust L, including but not limited to cable stretcher, 91 modulators e.g. 52, 54, movable reflecting devices, e.g., 46, and the like, as well as combinations including at least one of the foregoing. In fact, in an exemplary embodiment a separate cable stretcher 91 may be employed for the compensation addressed above and a second modulator e.g., 52, 54 employed for the magnitude and phase detection as described herein. A particular advantage of the autocorrelator configuration the LCI system 10b over the interferometer based LCI system 10 is that the optical circuit may be constructed employing simple low cost SM fibers, whereas, the a Michelson interferometer based LCI system of FIG. 6 could require that the optical system to be made out of PM fibers, particularly if the probe is to be part of a catheter. Polarization maintaining fiber is much more expensive than single mode fiber.

In one or more exemplary embodiments of the invention, several methodologies are disclosed for extracting the pertinent information from the interference signal $i_o$ described in Equation (5). A first methodology addresses detection of the amplitude/magnitude of the envelope of the interference signal, while others address detecting the phase, or more specifically a particular phase shift $\phi_s$ of the interference signal $i_o$ with respect to a depth scan. In an exemplary embodiment the process for the measurement of the phase of the LCI signal is applied to the detection of vulnerable plaques in a blood vessel. Detection of plaques with the phase of the interferometric signal includes a means to measuring phase changes and discontinuous phase change, such as occur at the interface between two media, particularly scattering media for example between blood and a fibrous cap, or between the cap and the lipid pool.

Furthermore, while the descriptions herein are further directed to the determination of $\Delta l$ with reference to the interferometer embodiments as depicted in FIG. 6, it should be appreciated that the methodologies disclosed herein are equally applicable to the autocorrelator embodiments as depicted in FIG. 7 with $\Delta$, as in equation (11), substituted for $\Delta l$ for the purposes of the derivations. For example, from equation (5) the phase of the interferometer signal is given as $$\phi_s = \frac{2\pi}{\lambda_o}\Delta l = \frac{2\pi}{\lambda_o}(l_r - n_s z),$$

where $n_s$ is the refractive index of the sample, while for the autocorrelator, an analogous equation given as $$\phi_s = \frac{2\pi}{\lambda_o}\Delta = \frac{2\pi}{\lambda_o}(4nL - 2(n_s z)),$$

where n is the refractive index for the fiber. Likewise, as Equation 6 identifies $\Delta\phi_s$, for the interferometer, the analogous equation for the autocorrelator would similarly be given by $$\Delta\phi_s = \frac{4\pi}{\lambda_o}(n_s \Delta z + z\Delta n_s).$$

In one embodiment, it may be desirable to measure sudden phase changes to facilitate locating boundaries between media. The processor 60 may be configured to cause the phase and/or magnitude of the interferometric signal to be measured discretely or continuously from one target depth to another target depth. If there is no material discontinuity in the process, the phase shift is generally linear with scanning distance (or time), and its slope (rate of change, first derivative) would be substantially a constant, and the change in the slope (second derivative) would be zero. Any material discontinuity at a given point would be manifested as both in a change of the slope, and in the fact that the second derivative would have a value that is different from zero. Such a value would be positive or negative, depending on whether the index change is positive or negative. The process for evaluating these changes in phase can easily be implemented digitally by storing the phase for each selected target depth during a depth scan and taking the numerical first and second derivatives.

Similarly, looking to the magnitude, as mentioned earlier, if there is no material discontinuity in the process, the magnitude varies generally with an exponential decay with scanning distance (or time). Once again, any material discontinuity at a given point would be manifested as an abrupt change in the difference and both in a change of magnitude and thereby, the slope, and in the fact in the second derivative. The process for evaluating these changes in magnitude can easily be implemented digitally by storing the magnitude for each selected target depth during a depth scan and taking the numerical first and second derivatives.

It will be appreciated that there are numerous numerical methods for implementation of a numerical derivative. As used herein the derivative may not need to be mathematically robust, but simply an approximation that captures the trend information of the phase of the interferometric signal. For example, considering the phase, given by $$\phi = \frac{2\pi}{\lambda_o}(l_r - nz)$$

so that in scanning from location $z_1$ to location $z_2$ within a medium of constant or slowly varying refractive index n, the phase changes from $$\phi_1 = \frac{2\pi}{\lambda_o}(l_r - nz_1) \text{ to } \phi_2 = \frac{2\pi}{\lambda_o}(l_r - nz_2)$$

such that its first derivative is the constant A given as:

$$A = \frac{\phi_2 - \phi_1}{z_2 - z_1} = \frac{2\pi}{\lambda_o}n \text{ radians/micron}$$

Thus, if $\lambda_o$=1.3 microns and n=1.3, then A is $2\pi$ radians/micron or 360 degrees/micron. However, if during a change from $z_1$ to $z_2$ there is also a change in refractive index, from $n_1$ to $n_2$, then the quantity A is no longer a constant. It changes from $A_1$ to $A_2$, and its rate of change, or derivative, or second derivative of the phase, is B given by:

$$B = \frac{2\pi}{\lambda_o}\frac{(n_2 - n_1)}{(z_2 - z_1)} = A_1\frac{(\Delta n/n_1)}{\Delta z} \text{ or } \frac{\Delta n}{n_1} = \frac{B}{A_1}\Delta z$$

The threshold for measuring the abruptness of the change is the smallest value of B that can be measured, and is a function of the sensitivity of the instrument, which ultimately depends on the detection noise (e.g., Johnson, shot, and excess intensity noises), and bandwidth in the instrument. Thus, suppose $A_1$ is 360 radians/micron, and suppose that, without going to the ultimate limit of measurement capability, the instrument is designed to measure accurately a value of B equal to 0.36 degree/micron per micron. Then the abrupt index change threshold would be 0.1% per micron of scan distance. It was shown in a previous application that the minimum measurable phase change, as determined by noise is of the order of $10^{-5}$ radian or about $6 \times 10^{-4}$ degrees. This would place the available sensitivity at about $2 \times 10^{-6}$ degrees per micron of displacement. Finally, it will be appreciated that while the description above for an exemplary embodiment pertains to the phase shift of the interferometric signal, an analogous approach may readily be applied for the magnitude. Once again, while the descriptions herein are further directed to the determination of $\Delta l$ with reference to the interferometer embodiments as depicted in FIG. 6, it should be appreciated that the methodologies disclosed herein are equally applicable to the autocorrelator embodiments as depicted in FIG. 7 with $\Delta$, as in equation (11), substituted for $\Delta l$ for the purposes of the derivations.

Magnitude Detection

Continuing now with FIGS. 1, 6, and 7, the first approach uses a periodic ramp applied to one of the modulators 52, 54. Another approach, also called a homodyne methodology employs a sine wave applied to one of the modulators 52, 54. It will be appreciated that while for the purposes of description of one or more exemplary embodiments, a particular modulator in a particular arm of the LCI system 10 is described as including a modulator, other configurations are conceivable. For example, while the description of an exemplary embodiment calls for modulation of the length of the reference arm of the LCI system 10, 10*b*, manipulation of other optical lengths in the LCI system 10 may be employed for establishing the interference signal and the level of modulation required to achieve the particular desired result.

Using one of the modulators, ($m_1$ 52, for example) a ramp modulation is applied to one of the interferometer arms, the reference arm 42, for example, changing $l_r$ over a distance from –b to a over a time period T, such that:

$$\Delta l = \frac{a}{T}t - b \text{ for } t < 0 < T \text{ and if periodic,} \quad (12)$$

$$\Delta l(t + T) = \Delta l(t).$$

This yields:

$$G(\Delta l)\cos\left(\frac{2\pi}{\lambda_o}\Delta l\right) = \exp\left[-\left(\frac{\frac{a}{T}t - b}{L_c}\right)^2\right]\cos\left[\frac{2\pi}{\lambda_o}\left(\frac{a}{T}t - b\right)\right] \text{ and,} \quad (13)$$

$$i_o(t) = 2\sqrt{I_rI_s}\cos(2\pi f_c t - \phi_c) \text{ where} \quad (14)$$

$$f_c = \frac{a}{\lambda_o T} \text{ and } \phi_c = \frac{2\pi b}{\lambda_o}.$$

Figure 8A:
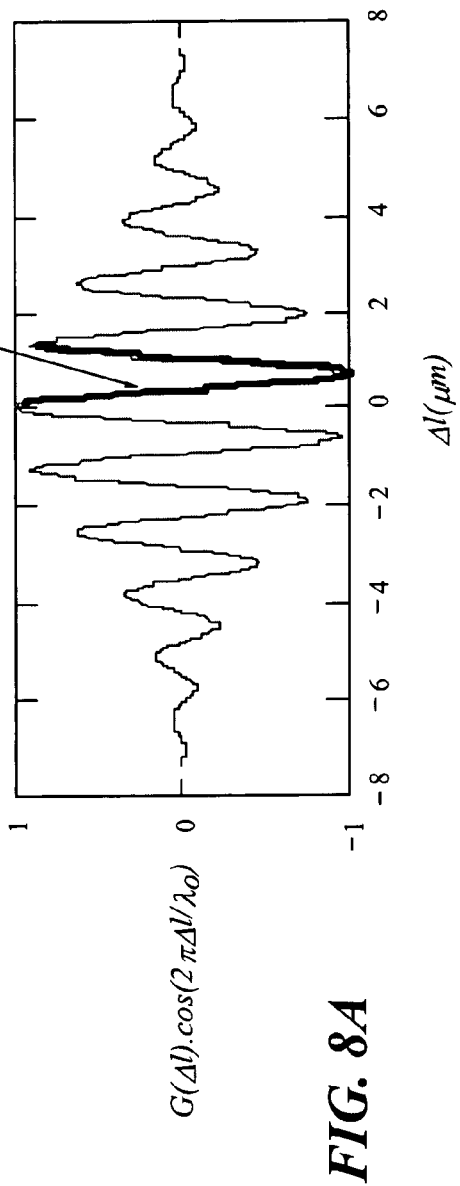
FIG. 8A depicts a range of unambiguous measurement for a periodic interference signal.
Figure 8B:
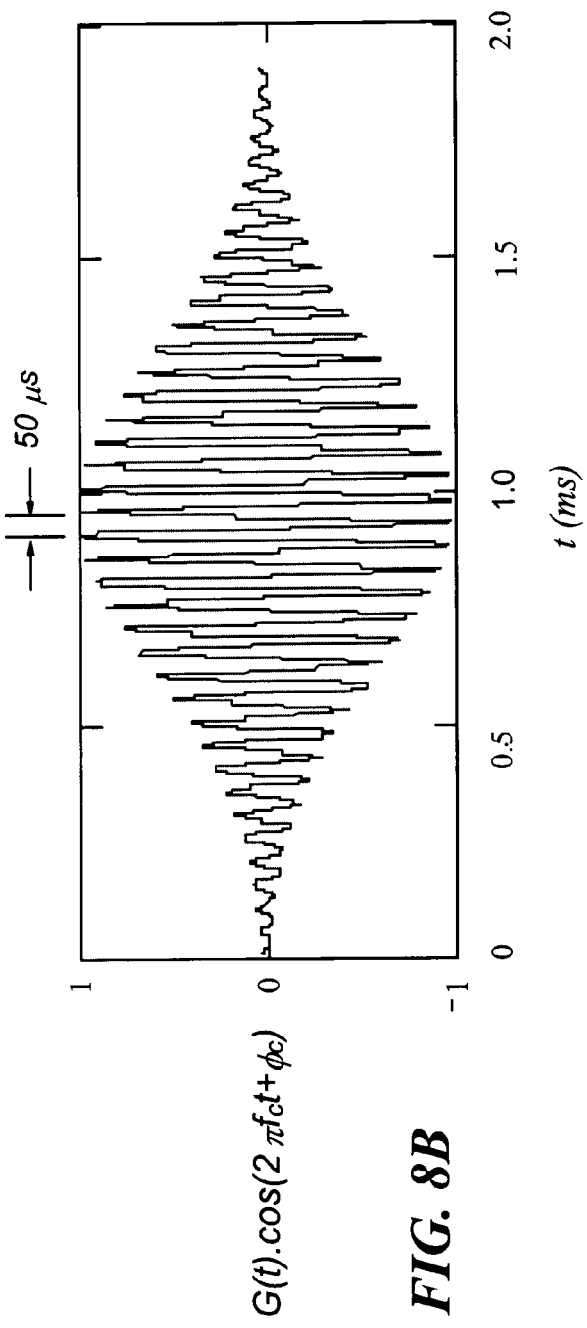
FIG. 8B depicts a plot of the interference signal for a single ramp.

The resultant of the modulation represents a sine wave of frequency $f_c$ with an arbitrary phase $\phi_c$ determined by b, which is amplitude-modulated (AM) by the G($\Delta l$) envelope function, now also a function of time. FIGS. 8A and 8B depicts a plot of the function in equation (13) for a single ramp sweeping over $\pm 2L_c$ for the light source example used earlier, with a=$4L_c$ and b=$2L_c$, and for T=1.9 ms, we get $f_c$=20 KHz. When the ramp function used for modulation is periodic, this signal repeats with the periodicity of the ramp function. Advantageously, the signal may be readily envelope-detected in similar fashion to an AM receiver signal to obtain G($\Delta l$), and peak-detected to yield G($\Delta l$=0), which can then be digitized for further processing.

Figures 9, 10:
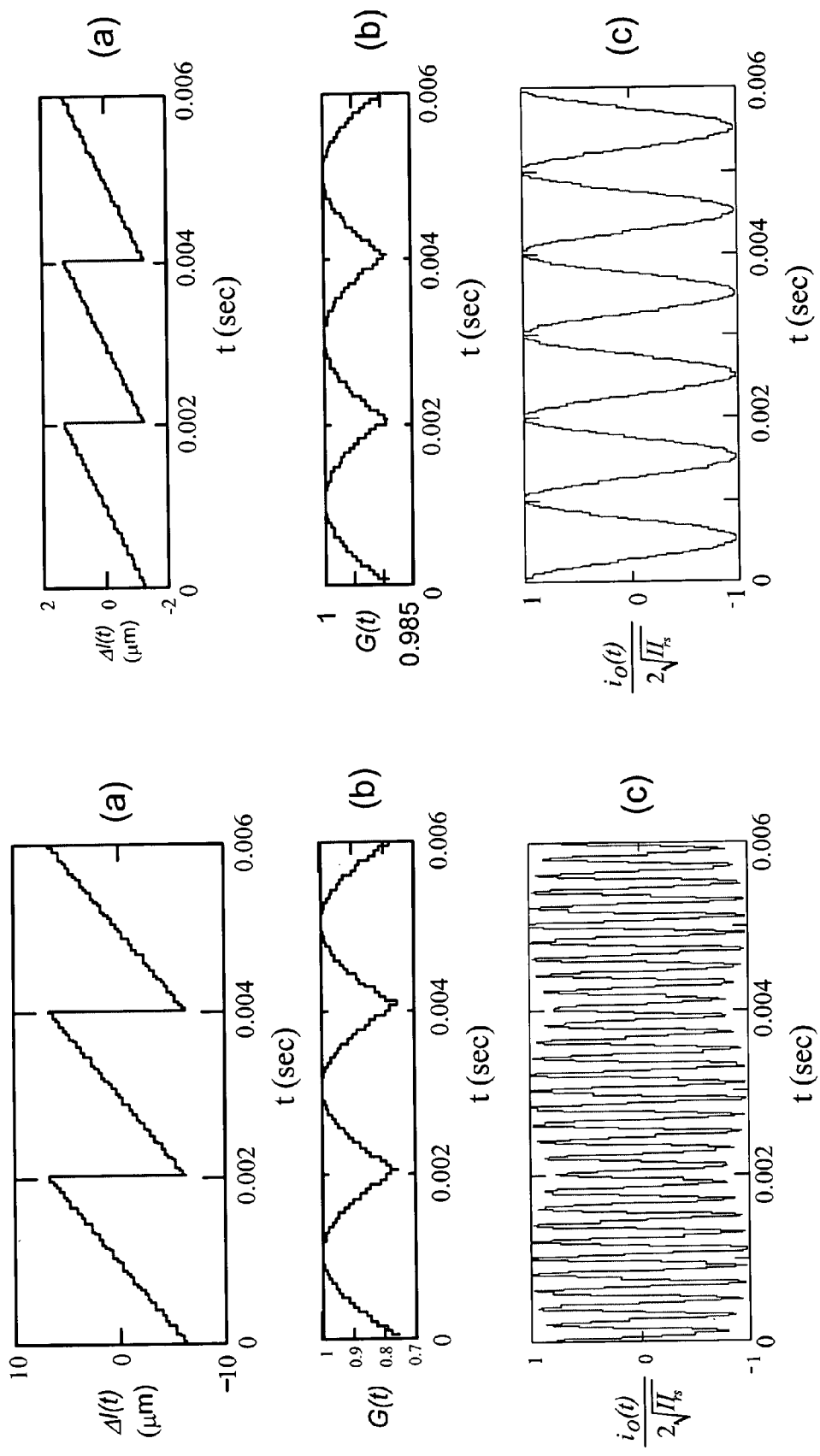
FIG. 9A depicts the values of $\Delta l$ for a periodic ramp for $a=5\lambda_o$ and $b=0.5a$.
FIG. 9B depicts the envelope function as a function of time for the particular $G(t)$ for $a=5\lambda_o$ and $b=0.5a$.
FIG. 9C depicts the output current or interference signal for $a=5\lambda_o$ and $b=0.5a$.
FIG. 10A depict the values of $\Delta l$ for a periodic ramp for $a=\lambda_o$ and $b=0.5a$.
FIG. 10B depicts the envelope function as a function of time for the particular $G(t)$ for $a=\lambda_o$ and $b=0.5a$.
FIG. 10C depicts the output current or interference signal for $a=\lambda_o$ and $b=0.5a$.

It should be noted that it is not essential to scan over such a wide range (e.g., $\pm 2L_c$) in order to obtain the peak of the envelope, e.g., G($\Delta l$=0). Advantageously, it is sufficient to ramp over as little as just one wavelength, using a=$\lambda_o$ and b=$\lambda_o/2$. The resultant signal is almost a pure sine wave or one that is slightly amplitude-modulated by G($\Delta l$). FIGS. 9 and 10 illustrate the response to a periodic ramp for modulator sweeps with a=$5\lambda_o$ and for a=$\lambda_o$ respectively, and b=a/2. FIGS. 9A and 10A depict the values of $\Delta l$, while FIGS. 9B and 10B depict the envelope function as a function of time for the particular G(t) $\Delta l$ respectively, and FIGS. 9C and 10C depict the output current or interference signals for each $\Delta l$, respectively.

Observation of the figures makes it evident that for a=$\lambda_o$ there is little need for filtering before peak detection to obtain the amplitude as the ripples in the envelope from peak to peak are quite small. For larger values of a, as depicted for FIGS. 9A–9C, a simple filtering technique with a center frequency around $f_c$ is sufficient to separate the modulation G($\Delta l$) [or now G(t)] from the carrier at $f_c$ if desired.

In an exemplary embodiment, once the magnitude of the interferometric signal $i_o$ is ascertained, for a selected target depth z, additional LCI signal magnitudes corresponding to other target depths are acquired. Furthermore, if desired, in order to obtain averaged distributions of the LCI signal intensity vs. depth multiple scans corresponding to multiple target depths may be employed. As disclosed herein, there are several methodologies and exemplary LCI systems that may be employed to acquire an interferometric signal $i_o$ corresponding to selected depths. In one exemplary embodiment, the modulator $m_1$ 52 may be employed to add an additional offsets denoted as $\Delta$ to the reference arm 42 corresponding to a group of target depth variations $\Delta z$ in the vicinity of target depth z. This approach is readily implemented employing the LCI system 10 of FIGS. 1, 6, 7, 16, and 17. It will be appreciated that the extent of such variations in the target depth $\Delta z$ are a function of the geometry of the waveguide arm and modulators employed. Additional details regarding the waveguide arms 42, and 44 and the configuration of the modulators $m_1$ 52 and $m_2$ 54 are addressed at a later point herein. In addition, an extension module (described at a later point herein) may also be implemented to facilitate variations in target depth and depth scans for some embodiments.

Figure 11:
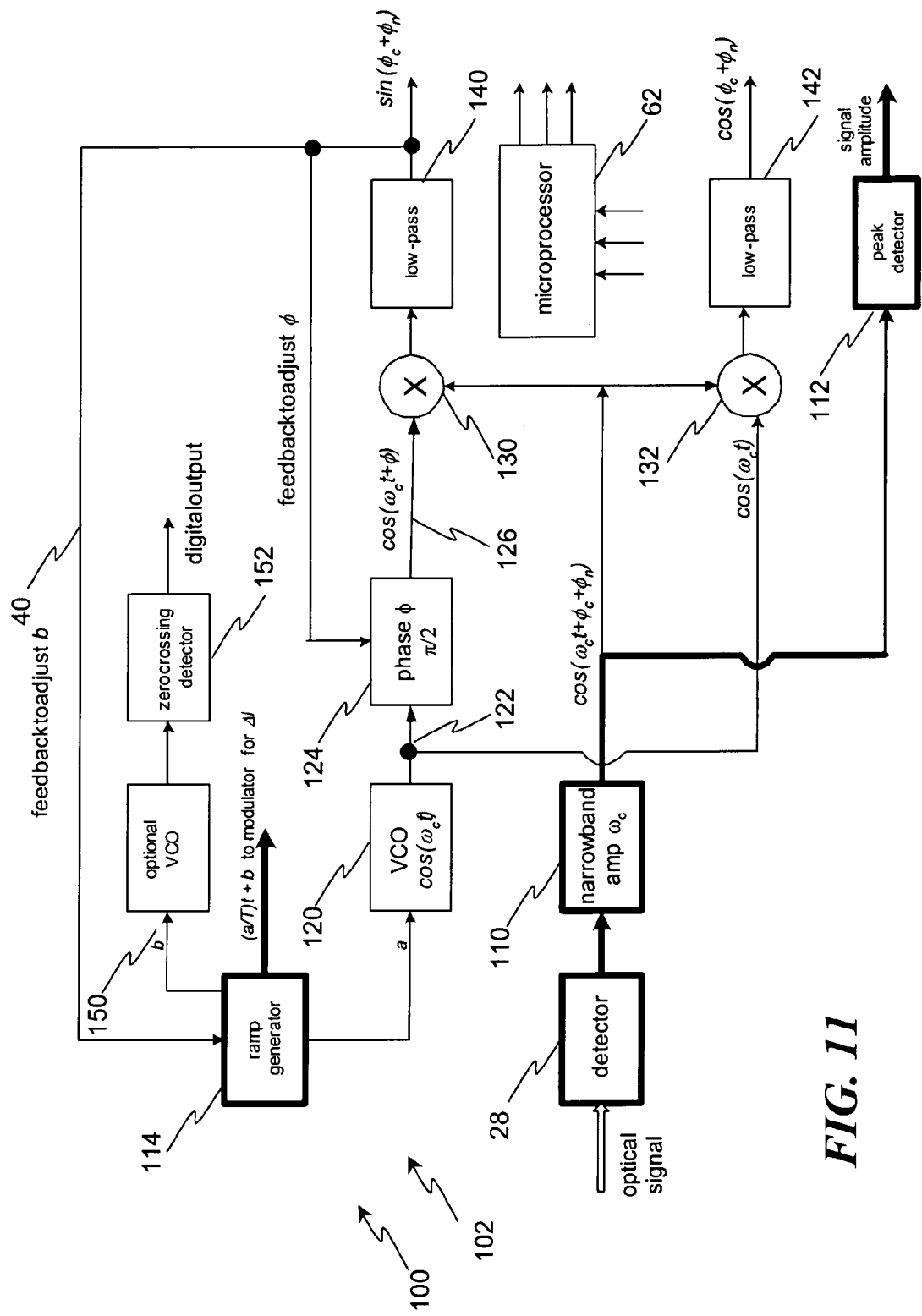
FIG. 11 depicts an as a simplified block depicting a detection scheme employing ramp modulation.

FIG. 11 depicts a illustrative implementation of the processes 100 that may be employed in accordance with an exemplary embodiment of the invention for determination of the magnitude and/or phase of the interference signal $i_o$. The bolded portions of FIG. 11 depict an implementation of a detection scheme using the ramp modulator for magnitude determination. The optical signal is observed at the optical detector 28 and applied to a narrowband amplifier/filter 110 resulting in the interference signal $i_o$. The interference signal is applied to a peak detector 112 to facilitate determination of the magnitude of the envelope of the interference signal $i_o$. A ramp generator 114 is utilized as the input to modulator $m_1$ 52 (FIGS. 1, 6, 7, 16, and 17) to facilitate manipulation of the length of one of the arms, in this instance, the reference arm 42 of the LCI system 10.

Phase Detection—Ramp Modulation

As discussed earlier, the most sensitive interferometric information can be derived from the phase variations of the interference signal $i_o$ resulting from small changes in material properties. For example, referring to Equation (5), a small change $\Delta n$ in the refractive index n, at a depth z in the sample, will result in a corresponding change in $\Delta l$ by the amount $z\Delta n$. To analyze such a change by a ramp modulation method as described above, the ramp described above in Equation (12), is applied to the modulator $m_1$ 52, but, in addition, an extra optical path length $z\Delta n$ is also included to facilitate addressing the phase shift in the interference signal $i_o$, yielding:

$$\Delta l = \frac{a}{T}t - b + z\Delta n, \text{ for } 0 \le t \le T \text{ and } \Delta l(t+T) = \Delta l(t) \quad (15)$$

and writing $G(\Delta l) \sim 1$ for $a \sim \lambda_o$, yields:

$$i_o(t) = 2\sqrt{I_r I_s} \cos(2\pi f_c t - \phi_c + \phi_n), \text{ where } \phi_n = \frac{2\pi}{\lambda_o}z\Delta n. \quad (16)$$

The phase shift of interference signal $i_o$ may readily be detected using a homodyne process 101 such as depicted in the block diagram of FIG. 11, which produces output signals proportional to the sine and cosine of the phase shift to be measured. In an exemplary embodiment, the change in $\Delta l$ produced by the ramp modulation generates the interferometric signal $i_o$ in the form of a sine wave, $\cos(\omega_c t + \phi_c + \phi_n)$ as in Equation (16), with an additional phase shifting component, denoted $\phi_n$ resulting from the change in the refractive index, $\Delta n$. At the same time, the parameter a of the ramp modulator 114 is applied to a voltage control oscillator (VCO) 120, configured to generate a sinusoidal function at a frequency $\omega_c$ proportional to the magnitude a from the ramp modulation. In an embodiment, a closed loop controller is employed to facilitate determination of $\phi_n$ as will be described herein. The sinusoidal function, $\cos(\omega_c t)$ 122 from the VCO 120 is phase shifted with phase angle $\phi$, as depicted at phase shifting process 124. The phase angle $\phi$ is set to $\pi/2$, to facilitate formation of quadrature sinusoidal signals. The phase-shifted sinusoid 126 is applied to a first multiplying demodulator 130 configured for the loop closure and denoted as a lock-in amplifier. The sinusoidal function $\cos(\omega_c t)$ 122 from the VCO 120 (without the phase shift $\phi$) is also applied to a second multiplying demodulator 132. Similar to the earlier embodiments, the interferometric signal $i_o$ from the optical detector 28 is amplified and filtered through a narrow band filter 110 around $\omega_c$, to extract the signal $\cos(\omega_c t + \phi_c + \phi_n)$, which is then applied to both multipliers 130 and 132 for multiplication by the sinusoidal signal 122 and the phase shifted sinusoidal signal 126. Using the relation $\cos(x)\cos(y) = 0.5\cos(x+y) + 0.5\cos(x-y)$, it will be appreciated that the output of the first multiplier 130 contains a term at frequency $2\omega_c$ and a DC term $\cos(\phi_c + \phi_n - \phi)$. Advantageously, the DC term $\cos(\phi_c + \phi_n - \phi)$ may be readily extracted by low-pass filtering as depicted at filtering process 140, and becomes $\sin(\phi_c + \phi_n)$ if $\phi = \pi/2$. Similarly, for the second multiplier 132, following similar low-pass filtering at process 142, the dc term is $\cos(\phi_c + \phi_n)$. Thus, after filtering the following two dc output signals are obtained:

from the first modulator: $I_{LP} = \sqrt{I_r I_s} \sin(\phi_c + \phi_n)$ and (17)

from the lower modulator: $I_{LP} = \sqrt{I_r I_s} \cos(\phi_c + \phi_n)$ (18)

It will be readily appreciated that both signals i.e., sine and cosine, contain the desired information, but the first provides better sensitivity to small $\Delta n$ changes. Preferably, both signals e.g., Equations 17 and 18, are used with their signs being compared to determine the quadrant in which the phase is located to properly obtain the index change. For example, for phase shifts determined to be between 0 and $\pi/2$, both signals are positive and increase or decrease in opposite manner. For phase shifts between $\pi2$ and $\pi$, they have opposite signs. For phase shifts between $\pi$ and $3\pi/2$, both are negative, and for phase shifts between $3\pi2$ and $2\pi$, they have opposite sign.

Therefore, by measuring the two outputs and observing their signs, the phase can be unambiguously ascertained for the range from 0 to $2\pi$. It is noteworthy to appreciate that this $2\pi$ limitation applies only if the variations of $G(\Delta l)$ [i.e., $G(t)$] are so small that the difference between the main peak (the absolute peak) and the adjacent ones is not readily measurable. If that difference is measurable, then it is possible to use the above algorithm, together with envelope detection, to ascertain the absolute peak, as well as the secondary peaks, and thus be able to measure phase shifts much in excess of $2\pi$ without ambiguity. (see FIGS. 3A and 8A as an example).

The index of refraction change $\Delta n$ can be retrieved in several ways. One methodology involves setting the value of b=0 (and thus $\phi_c=0$) and measuring the values for Equations (17) or (18) directly. Another methodology is to adjust/manipulate the value of b, using a feedback implementation, to result in a change to $\phi_c$ until the sine function of Equation (17) is nulled. When a null is achieved $\phi_c = -\phi_n$, which directly yields:

$$\Delta n = -\frac{b}{z} \qquad (19)$$

where z is the selected target probing depth and b is the magnitude of the change in optical path length introduced to balance the interferometer of the LCI system 10. For example, if the value of $\phi_c$ required for nulling is ascertained to be 5° (0.0873 radians) for $\lambda_o$=1.3 μm, it may be ascertained that (from $\phi=2\pi b/\lambda_o$) the value of b for nulling to be 0.018 μm, resulting in $\Delta n=1.8\times10^{-5}$ at z=1 mm. In one exemplary embodiment, a voltage proportional to b is transmitted to an optional VCO 150 to generate a sine wave of frequency proportional to b. That frequency may then be converted to a digital signal by means of an optional zero-crossing detector 152 for further utilization or display.

The expression of Equation (19) also indicates that greater sensitivity is obtained by probing deeper into the sample. Conversely, due to scattering and absorption in the probed sample e.g., tissue, the magnitude of the returned signal (Electric field $E_s$) and thus the interferometric signal $i_o$, is reduced at greater depth in the sample. However, it is also well known that if a signal is periodic, that signal may be retrieved by means of a high-gain narrow-bandwidth amplifier (at the expense of measurement time). Similarly, it can be retrieved by means of autocorrelation, again, at the price of measurement time. Thus, it may be inferred that, by using the phase detection methodology disclosed herein, the measurement sensitivity is, substantially independent of the magnitude of the interferometric signal $i_o$.

Phase Detection—Sine (Homodyne) Modulation

Figures 12A, 12B:
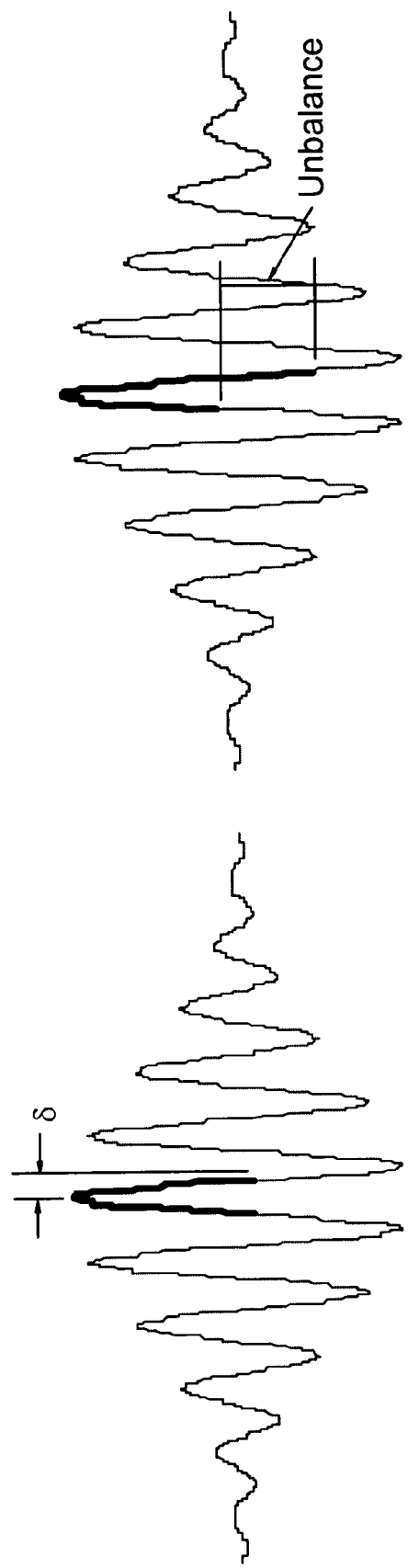
FIG. 12A shows a balanced interferometric signal resultant from sinusoidal modulation depicting a heavy portion oscillating at the frequency f over the peak.
FIG. 12B shows an unbalanced interferometric signal, and a shifted modulation pattern.

Turning now to another exemplary embodiment of the invention, in this case, the phase shift of the interference signal $i_o$ is determined utilizing a sinusoidal modulation technique. In order to detect the phase shift of the interference signal $i_o$, a small sine wave signal of amplitude δ and frequency f is applied to either of the modulators 52 or another modulator 54 ($m_1$ for example in FIG. 1 or FIG. 6 in this instance) for the interferometer based LCI system 10 or one of the cable stretching devices 98 of the autocorrelator configured LCI system 10b as depicted in FIG. 7. The small sinusoid results in a change to Δl as δcosωt, where ω=2πf, and forms a modulation pattern on the balanced interferometric signal such that it exhibits a "wiggle" or rides back and forth at the frequency f over the peak as shown by the heavy portion of the waveform in FIG. 12A. When the interferometer becomes unbalanced by virtue of a change in a material property, the modulation pattern (the heavy portion of the waveform) shifts resulting in the asymmetry as shown in FIG. 12B by virtue of the optical path change zΔn. Therefore, in an exemplary embodiment, for maintaining a controllable reference phase, provision is made to apply a fixed voltage to modulator $m_1$ 52 with a fixed displacement b and resulting in a phase shift $\phi_c$ as in the previous case.

Therefore, the general form of Δl at a given depth z with the sinusoidal modulation can be written as:

$$\Delta l = z\Delta n + b + \delta \cos\omega t \qquad (20)$$

and the general form of $\phi_s$ is:

$$\phi_s = \frac{2\pi}{\lambda_o}z\Delta n + \frac{2\pi}{\lambda_o}b + \frac{2\pi}{\lambda_o}\delta\cos\omega t = \phi_n + \phi_c + \phi_\delta\cos\omega t \qquad (21)$$

where ω=2πf and $\phi_\delta = 2\pi\delta/\lambda_o$.

Taking the cosine of the equation and converting yields:

$$\cos\phi_s = \cos(\phi_n + \phi_c)\cos(\phi_\delta \cos\omega t) - \sin(\phi_n + \phi_c)\sin(\phi_\delta \cos\omega t). \qquad (22)$$

The resultant is a phase-modulated signal, which can be expanded into the Fourier-Bessel series, using:

$$\cos\left(\frac{2\pi}{\lambda_o}\delta\cos\omega t\right) = J_o\left(\frac{2\pi}{\lambda_o}\delta\right) + \sum_n (-1)^n 2J_{2n}\left(\frac{2\pi}{\lambda_o}\delta\right)\cos 2n\omega t \qquad (23)$$

$$\sin\left(\frac{2\pi}{\lambda_o}\delta\cos\omega t\right) = \sum_n (-1)^{n+1} 2J_{2n-1}\left(\frac{2\pi}{\lambda_o}\delta\right)\sin(2n-1)\omega t \qquad (24)$$

where $J_n(x)$ is the Bessel function of the first kind of argument x and integer order n.

Substituting Equations (22), (23) and (24) into Equation (2) for $\cos\phi_s$, the interferometric signal now includes a DC term $J_0$, and an infinite number of harmonics $J_1$, $J_2$, $J_3$, etc. of decreasing magnitude. We keep the lowest terms by filtering through a low-pass filter, a filter centered at f and one centered at 2f respectively. We obtain the following outputs:

$$I_{oo} = 2\sqrt{I_r I_s}J_o(\phi_\delta)\cos(\phi_c + \phi_n) \text{ DC term} \qquad (25)$$

$$i_{o1}(t) = 4\sqrt{I_r I_s}J_1(\phi_\delta)\sin(\phi_c + \phi_n)\cos\omega t \text{ Fundamental term} \qquad (26)$$

$$i_{o2}(t) = 4\sqrt{I_r I_s}J_2(\phi_\delta)\cos(\phi_c + \phi_n)\cos 2\omega t \text{ Second harmonic term} \qquad (27)$$

where $G(\Delta l) \approx 1$, since $\Delta l \ll L_c$.

It is noteworthy to appreciate that the DC term $I_{oo}$ includes the same information with respect to the argument of interest $\phi_n$ as the second harmonic term $i_{o2}(t)$ and may be employed for ascertaining $\phi_n$. However, it is not as stable as $i_{o2}(t)$ and is subject to drift and other environmental factors. Furthermore, the DC term is not readily separable from the other detector DC components $I_r$ and $I_s$. On the other hand, $i_{o1}(t)$ and $i_{o2}(t)$ are locked to the oscillator frequency, which can be controlled accurately. Therefore, it is preferred that $i_{o1}(t)$ and $i_{o2}(t)$ are selected as the interferometer outputs. The amplitude of the fundamental and second harmonic terms may be ascertained, by various methodologies including, but not limited to, lock-in detection, multiplication and filtering as follows:

$$I_{o1} = 2\sqrt{I_r I_s}J_1(\phi_\delta)\sin(\phi_c + \phi_n) \qquad (28)$$

$$I_{o2} = 2\sqrt{I_r I_s}J_2(\phi_\delta)\cos(\phi_c + \phi_n). \qquad (29)$$

Figure 13:
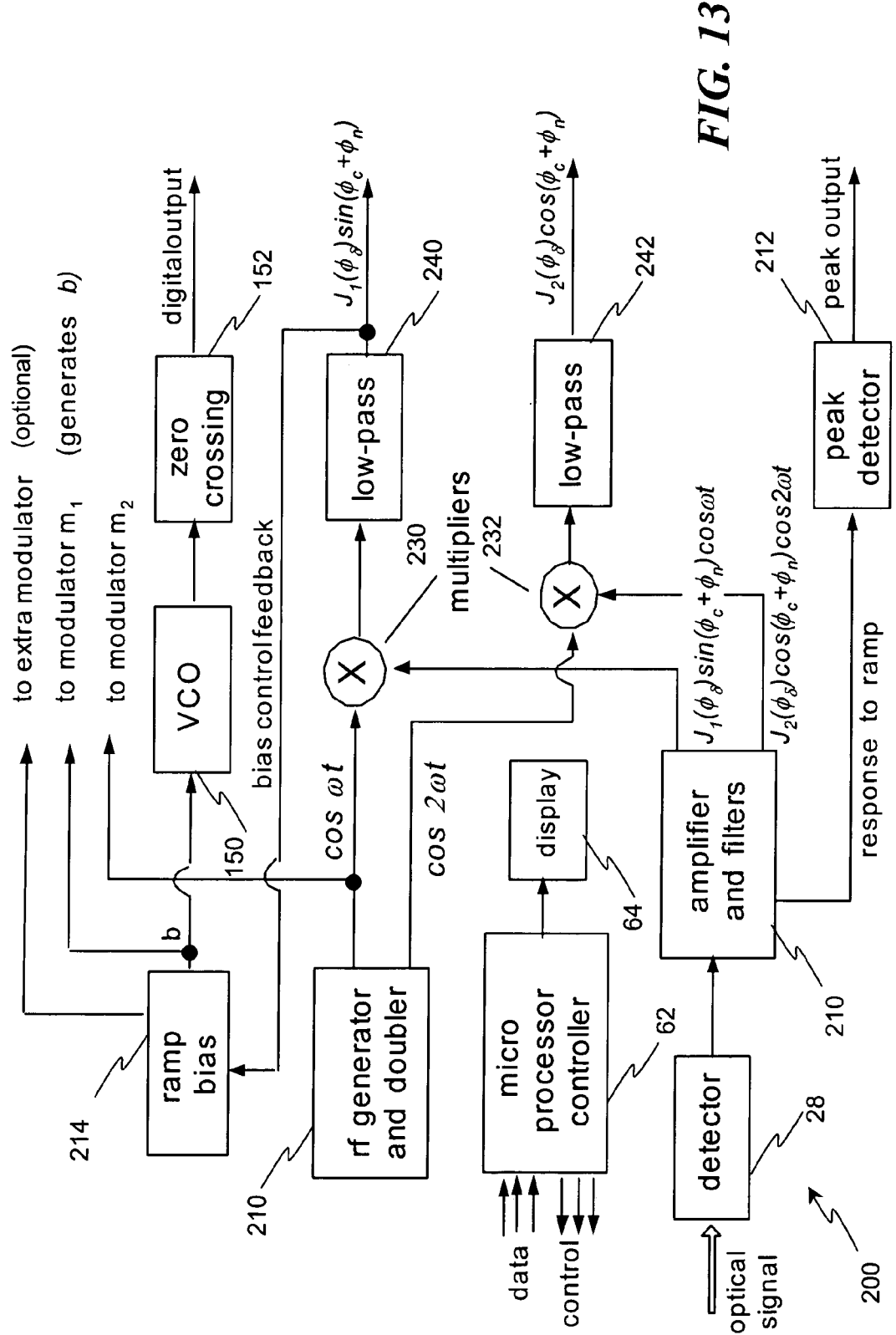
FIG. 13 depicts an implementation of a sinusoidal modulation or homodyne detection scheme.

FIG. 13 depicts an implementation of a sinusoidal modulation and detection or homodyne methodology shown generally as 200. Elements similar to earlier embodiments are similarly referenced but incremented by one hundred. A source 210 generates a sine wave denoted cos ωt of frequency f and second one of frequency 2f locked to the first one (for example, by means of a frequency doubler). In an exemplary embodiment a frequency f of about 100 KHz is employed, however, it will be evident that other frequencies may readily be utilized depending upon a particular implementation and application of the LCI system 10 or 10b. In fact, the frequency selected for modulation is not critical, and may be selected in accordance with a given implementation. The frequency selected is only limited by practical design constraints of a selected implementation e.g., size of components, processing requirements to implement functions, and the like. The sine wave at frequency f is fed to modulator $m_2$ 54 and to the upper multiplier 230 (e.g., a lock-in amplifier), and the sine wave at frequency 2f is applied only to the lower multiplier 232. A ramp generator 214 similar to that employed in the above embodiments, applies a dc voltage to the $m_1$ modulator 52 to produce the path length bias b, which is adjustable. In an exemplary embodiment, the path length bias b is adjusted to between 0 and $\lambda_o$ to produce a phase shift $\phi_c$ between 0 and $2\pi$. The detected interference signal $i_o$ is amplified and passed through narrow-band filters 210 to produce signals at $\omega$ and at $2\omega$, and these two signals are fed to the multipliers 230 and 232 respectively as shown. The output of the multipliers, after low-pass filtering at 240 and 242, are dc signals which correspond to the parameters in Equations (28) and (29).

It will be readily appreciated that except for the Bessel function coefficients, which are constants whose values are determined by their arguments $2\pi\delta/\lambda_o$, the functions in Equations (28) and (29) are identical to those in Equations (17) and (18) which were obtained from the ramp modulation scheme described earlier. However, advantageously, sinusoidal modulation is more robust and does not need special precautions to generate and control the reference frequency f and the $\pi/2$ electronic phase shift as in the previous case. In an exemplary embodiment the selection of the operating frequency f is arbitrary. However, it is preferable to keep it above the shot noise frequency range, i.e., above 120 KHz, where the shot noise is not significant.

It should also be noted that $\delta$ needs not be large in order to maximize $J_1$. It will be appreciated that the maximum value of $J_1(2\pi\delta/\lambda_o)$ occurs when $(2\pi\delta/\lambda_o)=1.85$, i.e., when $\delta=0.29\lambda_o$, giving $J_1(1.85)=0.582$ and $J_2(1.85)=0.311$. Equations (28) and (29) may then be utilized in a fashion similar to that employed with Equations (17) and (18) in order to measure the phase shift due to the change in index of refraction $\phi_n$ without ambiguity between 0 to $2\pi$.

Similarly, the value of $\Delta n$ may also be obtained from the values in Equations (28) and (29), the known values of $J_1$, $J_2$, and the magnitude of the $I_s$ and $I_r$ (which may be obtained via a calibration), and setting/driving $\phi_c$ to zero. Also as before, in an exemplary embodiment, an implementation employing feedback may be employed to adjust the bias b until the net phase shift is zero. Thereby, the resultant $\Delta n=-b/z$, may readily be obtained. Furthermore, using the value of b to set the frequency of a VCO 150 and zero crossing detector 152, a digital output indicative of the value of b may be obtained to facilitate the computation of $\Delta n$.

It should be further appreciated that the implementation depicted in FIG. 13 includes optional provisions to measure the peak of the interferometric signal $i_o$ under the application of a ramp to provide information on reflection and scattering coefficients. It also contains provision to apply a signal to an optional additional modulator (such as a fiber coil around a PZT drum) to facilitate ranging measurements by means of extra delays applied to the reference arm 42.

Another significant aspect of an exemplary embodiment of the invention employing the phase of the interferometric signal is the benefit achieved in measurement of the magnitude as described above. In another exemplary embodiment, the while the phase is measured and feedback loops nulled as described above, the magnitude of the interferometric signal is also measured. It should be appreciated that at the instant the added phase $\phi_c$ is set/driven to zero, the magnitude is at the absolute peak. Therefore, the phase measurement facilitates determination of the magnitude with the highest possible accuracy. Again, this approach is superior to existing magnitude detection methods because they do not employ the high resolution phase to control the measurement of the magnitude.

Figure 14:
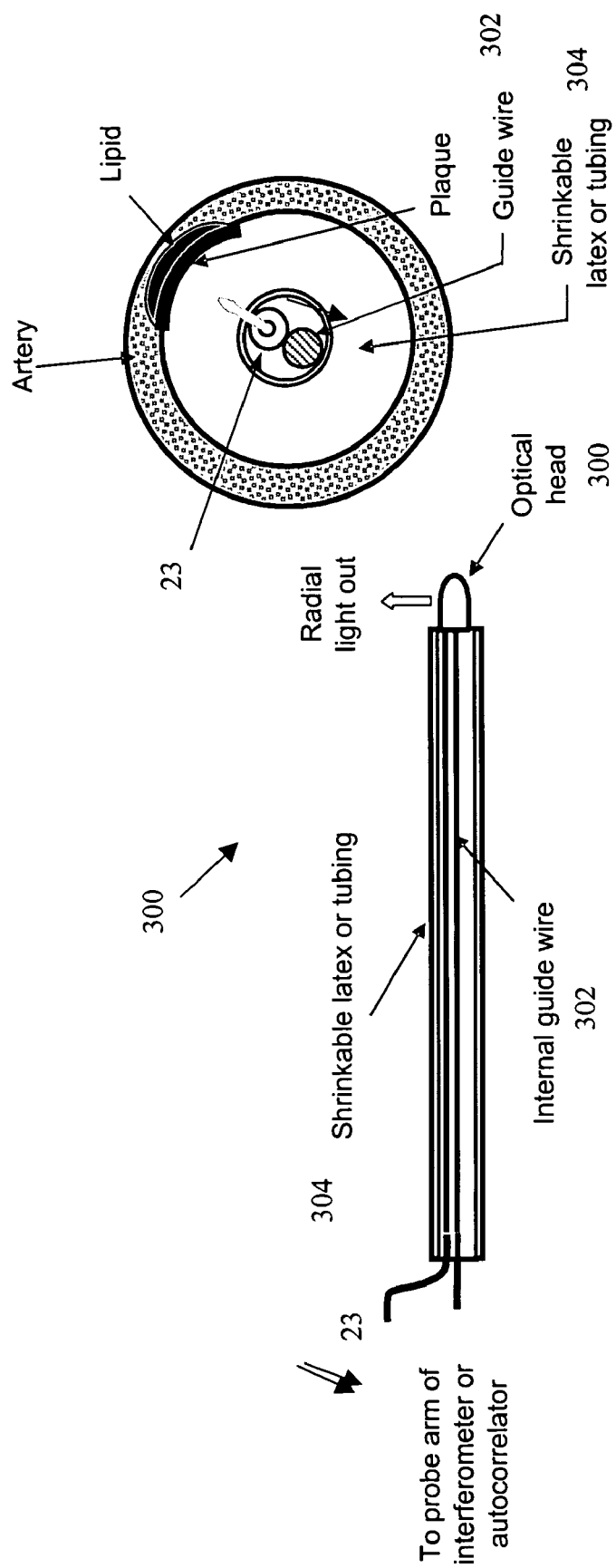
FIG. 14 depicts a fiber probe and guidewire in accordance with an exemplary embodiment.

FIG. 14 represents a possible embodiment of a probe 300 for the detection and measurement of vulnerable plaques and the way it "looks" at the wall of a blood vessel. In this particular instance, the probe 300 includes one or more fibers 23 placed around a guide wire or inside a guide wire 302 within a FDA-approved catheter 304. The illustration shows a blood vessel including a vulnerable plaque at a location corresponding to one of the probe elements (e.g., number 3 as indicated in the figure).

Figures 15A, 15B:
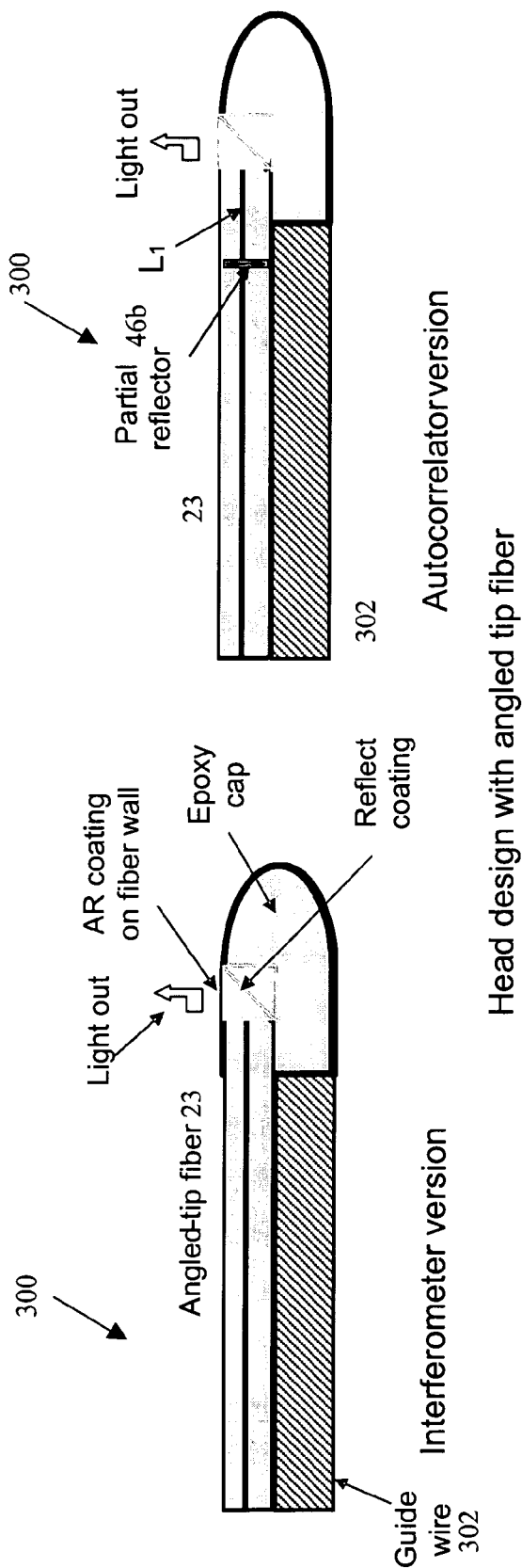
FIG. 15A depicts a probe tip in accordance with an exemplary embodiment.
FIG. 15B depicts a probe tip in accordance with another exemplary embodiment.

Cross-sections for configurations for the tip of the probe 300 in accordance with one or more exemplary embodiments are illustrated in FIG. 15. Several other configurations, such as some containing prisms, may readily be implemented as well. FIG. 15A depicts a configuration for a system that uses an interferometer as the sensing instrument e.g., LCI system 10. The tips of the fibers 23 are angled at about 45 degrees and the 45-degree surface is reflection-coated to maximize the light output toward the wall of the blood vessel. Furthermore, the tip of the probe 300 is preferably capped with an inert material such as epoxy and shaped such as to protect the fiber tips and prevent damage to the blood vessel. FIG. 15B depicts a similar embodiment for use in an autocorrelator configured LCI system 10b, where each fiber 23 element also includes a partial reflector 46b as discussed earlier and the optional extra delays 47 represented by lengths L1 and L2.

Sensitivity—Minimum Detectable Signal

Sensitivity is limited by noise, once the measurement interferometric signal $i_o$ is at or about the noise level it becomes impossible to discern the measurement from noise. Therefore, appreciation of the impact and contributions of noise components becomes instructive with respect to practical considerations of measurement limitations. The detection of the information in Equation (28) is limited by fluctuation noise. The minimum detectable signal is reached when it is equal to the noise, i.e., when the signal-to-noise ratio (SNR) is equal to unity. The noise power is expressed in terms of the photocurrent variance $\sigma_i^2$, which consists of the detector noise $\sigma_r^2$, the photon shot noise $\sigma_s^2$ and for the case of a broadband source 22, the excess photon noise $\sigma_e^2$. Hence, the total noise power is:

$$\sigma_i^2 = \sigma_r^2 + \sigma_s^2 + \sigma_e^2 \qquad (30)$$

The SNR (for signal $I_{o1}$ for a 1-ohm input resistance, for example), is given by:

$$SNR = \frac{I_{o/(rms)}^2}{\sigma_i^2}, \text{ where } I_{o/(rms)} = \frac{I_{o/}}{\sqrt{2}} \qquad (3)$$

The detector noise power is simply the thermal noise due to the input resistance of the receiver. It is given by $\sigma_r^2 = 4kTB$, where k is Boltzmann's constant ($k=1.38\times10^{-23}$ J/° K), T is the absolute temperature, and B is the bandwidth of the measurement. For a system having 1 KHz bandwidth at room temperature (T=300° K), its value is $1.66\times10^{-17}$ W.

The shot noise, or the noise due to the random arrivals of the photons on the detector 28 from a monochromatic source, obeys Poisson statistics. It is given by $\sigma_s^2 = 2eI_{dc}B$, where e is the electronic charge ($1.6 \times 10^{-19}$ coulombs) and $I_{dc}$ is the average detector DC current. If the total power incident on the detector 28 is of the order of about 1 mW and the detector quantum efficiency is of the order of unity, then $I_{dc}$ is of the order of 1 mA, and for the same detection bandwidth, the shot noise contribution is of the order of about $3.2 \times 10^{-19}$ W.

The excess intensity noise from a broadband source 22 is a Bose-Einstein process. It is given by (Rollins) $\sigma_e^2 = (1+V^2)I_{dc}^2 B/\Delta v$, where V is the degree of polarization of the light source 22, and $\Delta v$ its frequency bandwidth. From $v_o \lambda_o = c$, where c is the speed of light in vacuum, the frequency bandwidth is given by $c\Delta\lambda/\lambda_o^2$. For a source 22 with single polarization (V=0), center wavelength of 1.3 μm, FWHM wavelength bandwidth of 60 nm ($\Delta v = 1.07 \times 10^{13}$ Hz) and the same detector current and bandwidth as used previously, the excess intensity noise is about $\sigma_e^2 = 10^{-16}$ W.

All the noise components can be reduced by reducing the electrical bandwidth B. However, it is noteworthy to appreciate that for a broadband source, except at very low total optical power (e.g., corresponding to detector currents below 0.1 mA), the excess intensity noise is by far the dominant noise, followed the shot noise, then thermal noise for a high impedance detector or receiver. Thus, for moderate optical power:

$$SNR \approx \frac{I_{o/(rms)}^2}{\sigma_e^2}, \text{ where } \sigma_e^2 = I_{dc}^2 \frac{B}{\Delta v} \quad (32)$$

indicating for a broad band source only the excess intensity noise need be considered to evaluate sensitivity. In addition, analysis of the excess intensity noise permits determination of the advantages of employing a phase based techniques of detection/measurement of the interferometric signal $i_o$.

As an example, suppose it is desirable to determine the minimum detectable index change at a depth z in a given specimen with the 1.3-μm light source, 1 KHz detection bandwidth, etc. Assume $I_r \sim 1$ mA, $I_s \sim 0.1$ mA, $J_1 = 0.582$ and let $\Delta n$ be small enough that the sine term in Equation (28) can be replaced by its argument. Then, for SNR=1, the resultant from Equation (32) yields:

$$(z\Delta n)_{min} \approx 4 \times 10^{-6} \text{ μm} \quad (33)$$

As mentioned earlier, the minimum detectable index change depends inversely on the probing depth. At a depth of 1 mm, i.e., 1000 mm, the minimum index change is $\Delta n_{(min)} \sim 4 \times 10^{-9}$. At 2 mm probing depth then $\Delta n_{(min)} \sim 2 \times 10^{-9}$. It also depends on the square root of the detection bandwidth, so a factor of three reduction is obtained by reducing the bandwidth from 1 KHz to 100 Hz. The improvement in sensitivity of the phase measurement approach over the amplitude measurement approach stems from the phase factor $\sin(\phi_n)$ in the expression for the phase signal, which does not exist in the amplitude case. At low signal levels, it multiplies the amplitude signal by the factor $2\pi z\Delta n/\lambda_o$ in which the quantity $2\pi z/\lambda_o$ is of the order of 6,000 for the examples used in the calculations. For example, for optical power below approximately 0.1 mW or equivalently for detector current below approximately 0.1 mA, the dominant noise source is the thermal noise. The sensitivity is obtained in the same manner as above, but with the excess noise replaced by the thermal noise in the expression for the SNR. This changes $z\Delta n(min)$ somewhat, but does not change the fact that it is a small value.

Detectable Range Of Measurement Without Ambiguity

The interference signal $i_o$ repeats itself after the argument of the sine function in Equation (20) changes by $2\pi$, thus when the coherence length $L_c$ is (larger than about $10\lambda_o$) such that the maximum detectable phase change without ambiguity is $2\pi$, equivalent to $\Delta l=0$. This yields:

$$(z\Delta n)_{max} = \lambda_o \quad (34)$$

Thus, for example, at a 1.3-μm wavelength, $\Delta n^{(max)} \sim 1.3 \times 10^{-3}$ at 1-mm probing depth, and $\Delta n_{(max)} \sim 6.5 \times 10^{-4}$ at 2-mm probing depth. Just as the probing depth can be used to control the sensitivity, it can also be used to control the maximum detectable change. The range of the instrument is the ratio of the maximum to minimum detectable signals. For the examples discussed herein, this range is $3 \times 10^5$ or 55 dB. For a larger index change, methodology that may be employed is to use the envelope detection method or a combination of phase and envelope detections as described earlier.

Note that, since these results are independent of the overall magnitude of the interferometric signal, it is sufficient to make these measurements at only one depth. The depth needs to be changed only to change the scale of the LCI system 10.

Referring once again to FIGS. 16 and 17, broadband light sources 22 including, but not limited to, SLD's are laser type structures configured and designed to operate substantially without feedback, e.g., of the order of less than $10^{-3}$, preferably less than $10^{-4}$, more preferably less than $10^{-5}$. In the presence of feedback, the spectrum of the SLD light source 22 may be distorted, the coherence is significantly increased and the spectrum can exhibit very large ripples and even lasing spikes, and thereby may become lasers. Therefore, to prevent distortion and maintain spectral integrity, low coherence, and broadband characteristics, reflections back into the light source 22 are avoided to maintain a broadband light source 22. Thus, in an exemplary embodiment of the LCI system, isolation is provided to alleviate feedback to the light source 22.

Continuing with FIGS. 6 and 7 as well as 16 and 17, in an exemplary embodiment, the source-detector module 20a, 20b, is configured to prevent the reflected interferometer light from reaching the SLD light source 22 and upsetting its operation. The SLD source 22 is designed and configured such that it is linearly polarized. SLDs and lasers are "heterostructures", semiconductor devices consisting of a thin "active" layer sandwiched between two "cladding" layers of lower refractive index, all epitaxially grown on a single crystal substrate. One such process for fabrication is known as MOCVD (metalorganic chemical vapor deposition). One of the cladding layers is p-doped, and the other is n-doped. The substrate is typically n-doped, and the n-cladding layer is the first to be deposited on it. The structure forms a p-n semiconductor junction diode, in which the active layer is caused to emit light of energy equal to its bandgap upon the application of an electric current.

The structure is called heterostructure because the active and clad layers are made of different material. This is in contrast with ordinary diodes in which the p-n junction is formulated between similar materials of opposite doping. The use of heterostructure has made it possible to confine the electrical carriers to within the active region, thus providing high efficiency and enabling operation at room temperature.

In many heterostructures, light is emitted in both TE polarization (the electric field in the plane of the layer) and TM polarization (electric field perpendicular to the layer).

However, useful effects are obtained when the active layer is sufficiently thin such that quantum mechanical effects become manifest. Such thin layers are called "quantum well" (QW) layers. Furthermore, the active layer can be "strained", i.e., a slight mismatch (of about 1%) with respect to the substrate crystal lattice can be introduced during the deposition of the QW layer. The strain can modify the transition characteristics responsible for light emission in beneficial ways. In particular, the light is completely polarized in the TE mode if the strain is compressive. Thus, it is now possible to make a linear polarized laser or broadband SLD by compressive strain of the active layer. In an exemplary embodiment, such a linearly polarized light source 22 is employed.

In one exemplary embodiment, as depicted in FIG. 16, the light from the light source 22 is directed through an isolator 24 configured to transmit light in one direction, while blocking light in the opposite direction. The light is directed to a splitter/coupler 50 of the splitter-modulator module 40a. The source-detector module 20a also contains a detector 28 to receive from the splitter/coupler 50.

In another exemplary embodiment as depicted in FIG. 17, the linearly polarized light from the SLD light source 22 is collimated with lenses 27 and applied to a splitter 25. If a basic 50/50 splitter 24 is employed, half of the returned light goes to the detector 28 and the other half is directed to the SLD light source 22. Once again, in this configuration an isolator 24 may be employed to prevent feedback to the light source 22. Similarly, as stated earlier, in another exemplary embodiment, the splitter 25 is a polarizing beam splitter 25 operating in cooperation with a quarter wave plate 26, employed to prevent feedback light from reaching the light source 22. The polarizing beam splitter 25 facilitates the elimination of feedback to the SLD light source 22 by redirecting substantially all the reflected light from the splitter-modulator module 40b to the detector 28.

The splitter 25 transmits the horizontally polarized light to the quarter wave plate 26, which coverts the light to another polarization, (for example, circular polarization). Likewise, the returning, circularly polarized light is received by the quarter wave plate 26 and is reconverted to a linear polarization. However, the linear polarization opposite, for example, vertical. The vertically polarized light is transmitted to the polarizing beam splitter 25, which directs all of the light to the detector 28. Advantageously, this approach transmits substantially all of the light i.e., the interference signal, to the detector 28. Whereas embodiments employing the isolator 24 transmits approximately half of the light to the detector 28.

The polarizing beam splitter 25 is a device that transmits light of one polarization (say the horizontal, or TE-polarized SLD light) and reflects at 90° any light of the other polarization (e.g., vertical or TM-polarized). The quarter-wave plate 26 is a device that converts a linearly polarized incident light to circular polarization and converts the reflected circularly polarized light to a linearly polarized of the other polarization, which is then reflected at a 90° angle by the polarizing beam splitter 25 to the detector 28. Therefore, essentially all the light transmitted by the light source 22 is re-polarized and transmitted to the splitter-modulator module 40b and all the reflected light from the sample and reflecting device 48 is deflected by the polarizing beam splitter 25 to the detector 28. Advantageously, this doubles the light received at the detector 28 relative to the other embodiments, and at the same time minimizes feedback to the SLD light source 22.

In an exemplary embodiment an SLD chip for the light source 22 has dimensions of approximately 1 mm×0.5 mm×0.1 mm (length×width×thickness), and emits a broadband light typically of up to 50 mW upon the application of an electric current of the order of 200–300 mA. The light is TE-polarized if the active layer is a compressively strained QW. The FWHM spectrum is of the order of 2% to 3% of the central wavelength emission. A SLD light source 22 with 1.3 µm center wavelength emission and operating at 10 mW output power at room temperature would have a bandwidth of about 40 nm and would require about 200 mA of current. In an exemplary embodiment, for continuous wave (cw) operation at room temperature, the SLD light source 22 may be mounted on an optional thermoelectric cooler (TEC) 32 a few millimeters larger than the SLD light source 22 chip to maintain the temperature of the light source 22 within its specified limits. It will be appreciated that the SLD light source 22 and associated TEC 32 peripherals in continuous operation would have the largest power consumption in the LCI system 10. However, without the TEC 32, the SLD junction temperature would rise by several degrees under the applied current and would operate at reduced efficiency.

Advantageously, in yet another exemplary embodiment, the utilization of a TEC 70 may readily be avoided without incurring the effects of significant temperature rise by pulsed operation of the SLD light source 22. Pulsed operation has the further advantage of reducing the SLD electrical power requirement by a factor equal to the pulsing duty cycle. Moreover, for selected applications of digital technology and storage, only a single pulse is sufficient to generate an interference signal and retrieve the desired information. Therefore, for example, with pulses of duration 10 µs and 1% duty factor, the LCI system 10 of an exemplary embodiment can average 1000 measurements per second without causing the temperature of the SLD light source 22 to rise significantly. Thus, for low power consumption, the LCI system 10 should preferably be designed for the SLD light source 22 to operate in a pulsed mode with a low duty cycle and without a TEC 32. In such a configuration the source-detector module 20 would be on the order of about 2 centimeters (cm)×2 cm×1 cm.

The splitter-modulator module 40a, and 40b of an exemplary embodiment includes a splitter/coupler 50 and Y-splitter/combiner 51 respectively, with a "reference" arm 42 and a "sensing" arm 44, the reference arm 42 having a slightly longer optical path (for example, 1 to 3 mm for measurements in biological tissues) than the sensing arm 44. The optical path difference between the two arms 42, 44 is configured such that the LCI system 10 balanced for the chosen probing depth z. Provision is also made to include a modulator $m_1$ 52 and $m_2$ 54 in the reference arm 42 and sensing arm 44 respectively.

Figure 18:
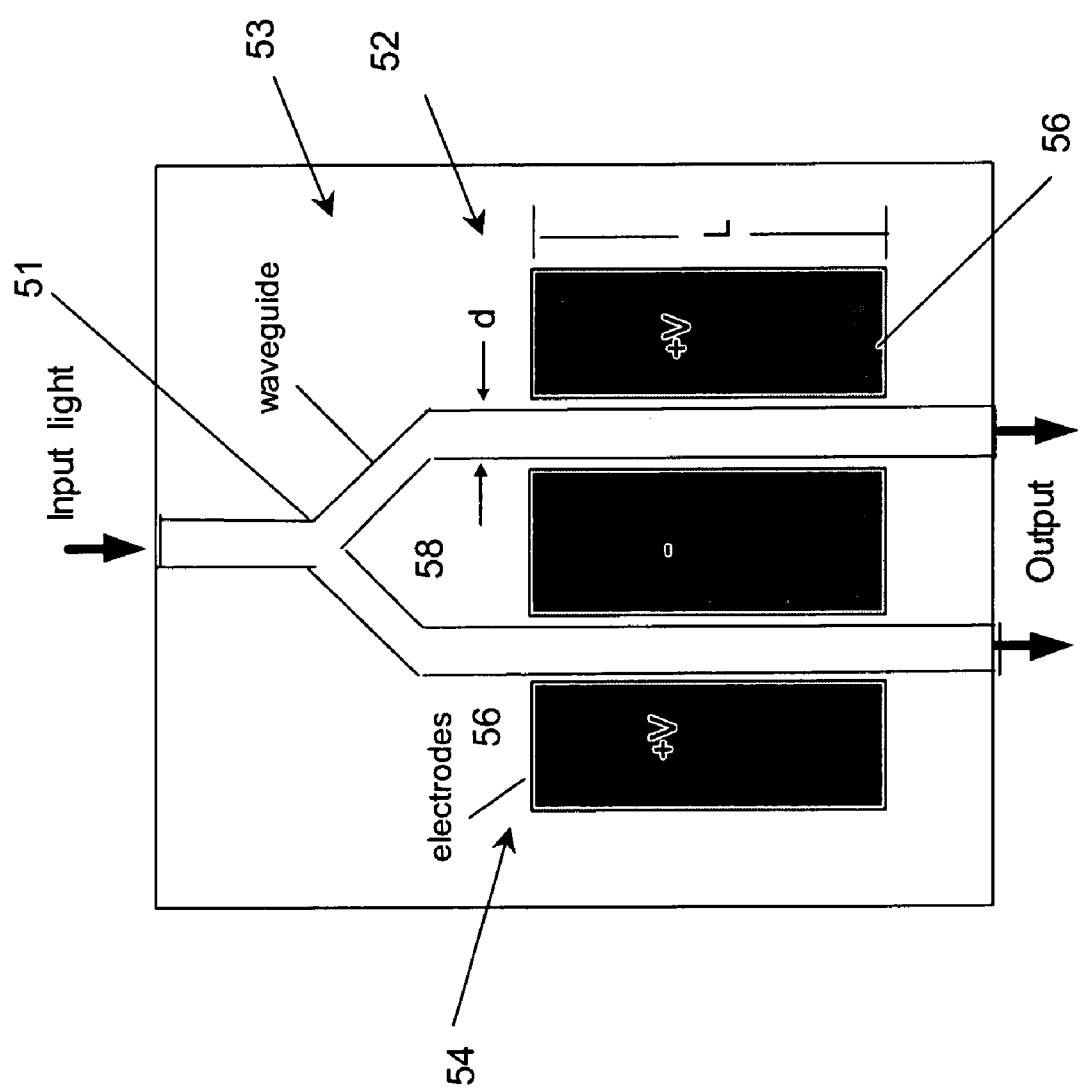
FIG. 18 depicts an illustration of a splitter-modulator module in accordance with an exemplary embodiment.

In another exemplary embodiment, the splitter/coupler 50, Y-splitter/combiner 51 reference arm 42 and a sensing arm 44 are formed as waveguides in a substrate 53. FIG. 18 depicts an illustration of a splitter-modulator module 40b with a Y-splitter 51 and two modulators 52, 54 integrated on a LiNbO3 substrate 53. However, other configurations are possible, including but not limited to separate components, waveguides, optical fiber, and the like. The substrate 53 for this module should preferably, but not necessarily, be selected such that the waveguides of the arms 42, 44 and modulators 52, 54 can be fabricated on/in it by standard lithographic and evaporation techniques. In one exemplary embodiment, the waveguides of the arms 42, 44 are fabricated by thermal diffusion of titanium or other suitable metal that increases the index of refraction of the substrate 53, evaporated through masks of appropriate width for single transverse-mode operation. In another exemplary embodiment, the waveguides are formed by annealed proton exchange in an acid bath. This process raises the refractive index in the diffusion region, thus creating a waveguide by virtue of the refractive index contrast between the diffusion region and the surrounding regions. In an exemplary embodiment, is lithium niobate (LiNbO3) is employed as a substrate 53. It will be appreciated that other possible materials, namely ferroelectric crystals, may be utilized such as lithium tantalite (LiTaO3) and possibly indium phosphide depending on configuration and implementation of the LCI system 10.

Lithium niobate is a ferroelectric crystal material with excellent optical transmission characteristics over a broad wavelength range from the visible to the infrared. It also has a high electro-optic coefficient, i.e., it exhibits a change of refractive index under the application of an external electric field. The refractive index change is proportional to the electric field. The speed of light in a transparent solid is slower than in vacuum because of its refractive index. When light propagates in a waveguide built into the electro-optic material, an applied electric field can alter the delay in the material, and if the electric field is time-varying, this will result in a phase modulation of the light. The LiNbO3 material is very stable, the technology for making it is mature, and LiNbO3 modulators, which can be compact and are commercially available.

In an exemplary embodiment, the high electro-optic coefficient (refractive index change with applied electric field) of lithium niobate is exploited to facilitate implementation of a modulator, such as modulators $m_1$ 52 and $m_2$ 54. In this embodiment, a modulator is implemented on or about the waveguide arms 42, 44, by depositing metal electrodes 56, 58 in close proximity to the waveguide arms. In one embodiment, the metal electrodes 56, 58 are deposited on the sides of the waveguide arms 42, 44. In another, the metal electrodes 56, 58 may be deposited on the waveguide arms 42, 44 with an appropriate insulation layer, in a selected region. FIGS. 16 and 17 also shows a diagrammatic depiction of a modulators $m_1$ 52, $m_2$ 54 in each arm 42, 44 fabricated by depositing metal films (electrodes) 56 on the outside the waveguides and a larger "common" electrode 58 between them. Modulation with modulator $m_1$ 52 is obtained by applying a voltage between the upper electrode 56 and the common electrode 58, and modulation with modulator $m_2$ 54 is obtained by applying a voltage between the lower 56 and the common electrodes 58. The change of refractive index with applied voltage results in a delay or a change of optical path between for the modulated arm 52, 54. For a given applied voltage, the optical path change depends on the length of the electrodes 56, 58.

The process of fabricating a modulator in an exemplary embodiment is illustrated in FIGS. 19A–C. Titanium and a lithium niobate substrate 53 are employed. In the diffusion process, a waveguide pattern is etched in a mask and a thin layer of titanium is vacuum-deposited onto the substrate 23 through the mask. The substrate 23 is then heated in an oven at about 900–1000 degrees C. to diffuse the titanium into the lithium niobate substrate 23. The index of refraction of the diffusion region is slightly higher than that of the surrounding material, and this constitutes waveguides in which light is guided in the diffusion region by virtue of its higher refractive index (just as in an optical fiber where the light propagates in the higher index core). Following diffusion, the metal electrodes 56 and 58 for the modulator(s) 52, 54 are deposited on the sides as shown, with a small spacing d between them. Application of a voltage V between one of the outer electrodes 56 and the negative center electrode 58 establishes an electric field of value V/d across the waveguide e.g. reference arm 42 and/or sensing arm 44. In an exemplary embodiment, the width of the waveguide is approximately 3–5 microns, and the spacing d is only a few more microns wider.

The refractive index change due to the electro-optic effect is given by $$\Delta n = -\frac{1}{2}n_o^3 r \frac{V}{d} \quad (35)$$

where $n_o$ is the refractive index, and r is the electro-optic coefficient. The phase shift of a light of wavelength λ propagating in a LiNbO3 modulator is given by $$\Delta\phi = \pi \frac{L}{\lambda} n_o^3 r \frac{V}{d} \quad (36)$$

where L is the length of the modulator electrodes 56, 58. In the context of the LCI systems 10 disclosed herein, this corresponds to an optical path length change of $$\Delta l = \frac{1}{2} n_o^3 r L \frac{V}{d} \quad (37)$$

Typical material properties are:

$r$=11.3×10$^{-12}$ m/V $n_o$=2.35

To obtain larger scale modulations, it will be appreciated that an increase in the voltage on/or the length of the modulator will result in larger changes in the index of refraction by the modulator, resulting in an increased variation of the corresponding phase delay. For example, with a configuration of d=10 microns, an applied voltage of only 3.6 volts is sufficient to yield a value of Δl or b (as discussed above) of 1.3 microns (the wavelength of the light discussed in the examples above). This illustrates that a modulator with a range equivalent to the wavelength λ (for example) 1.3 microns may readily be achieved employing the configuration described.

In an exemplary embodiment, the reference arm 42 is terminated in an evaporated mirror (metal or quarter-wave stack) 46, and the sensing arm 44 is terminated in an anti-reflection (AR) coating, or is covered with an index-matching agent 48 that prevents or minimizes reflection from the end of the sensing arm 44 when placed in contact with the object to be measured. In such a configuration splitter-modulator module 40 of an exemplary embodiment would be on the order of about 2 cm×2 cm×0.5 cm. Smaller and larger sized modules are envisioned based on the various implementations of the exemplary embodiments employed.

Calibration

Figure 20:
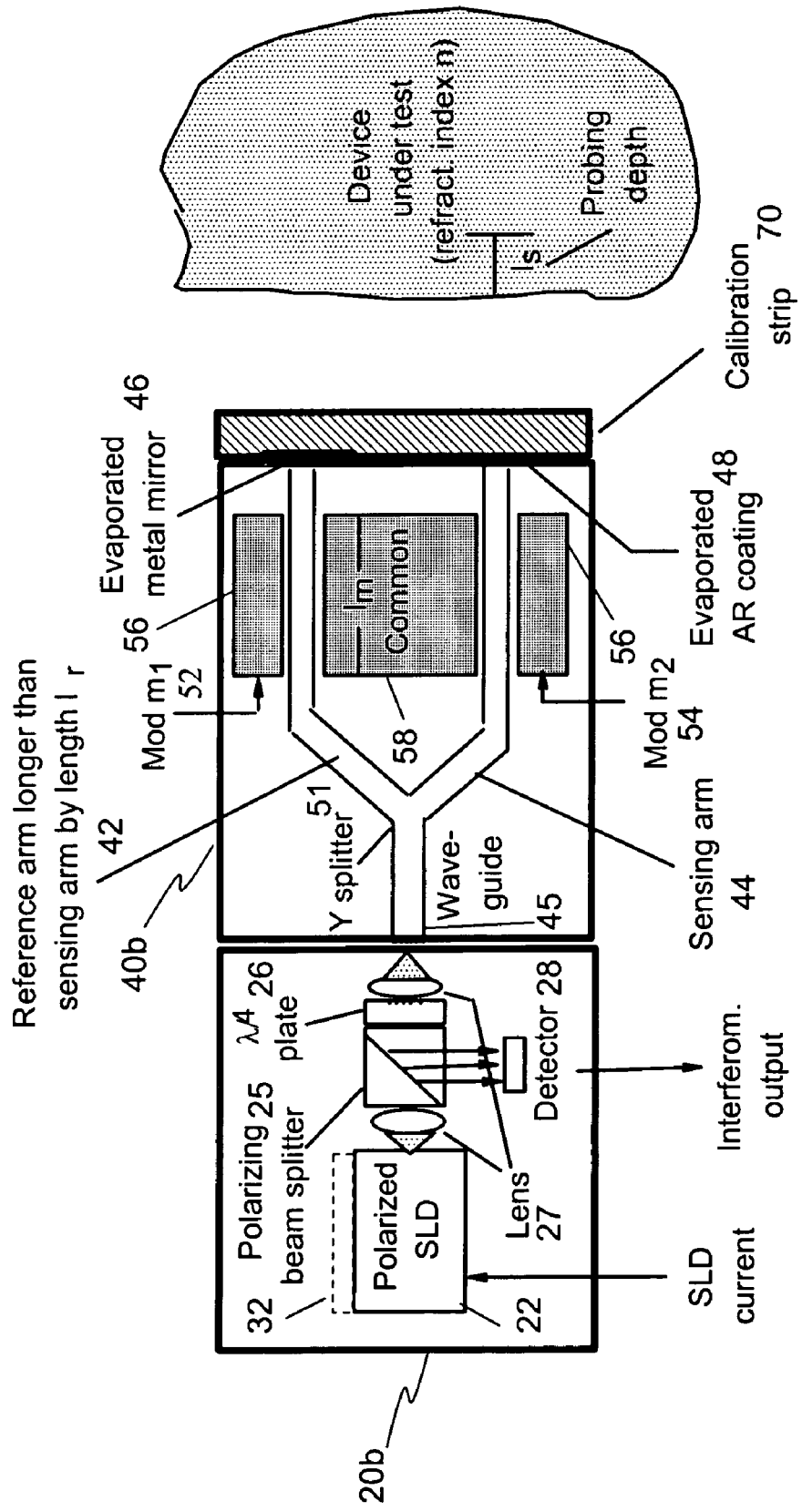
FIG. 20 depicts an adaptation of the interferometer system of FIG. 16/17 with a calibration strip.

FIG. 20 depicts an exemplary embodiment of the LCI system 10, 10b of FIGS. 16 and 17 with a calibration strip 70 in place. The calibration strip 70 can serve the dual purpose of calibration and refractive index matching. In an exemplary embodiment the phase associated with a selected length of the reference arm 42 is pre-calibrated to correspond to a set depth (or zero in one instance). The spot size for the light at the tip of the sensing fiber or waveguide of the sensing arm 44 is on the order of a few microns. The LCI system 10 may readily be calibrated by placing a strip of known parameters, e.g., refractive index (and the like) and appropriate thickness at the sensing end of the splitter-modulator module 40 prior to performing a measurement. Its placement in contact with the splitter-modulator module 40a, 40b (FIGS. 16 and 17) does not affect the reference arm 42, since the reference arm light does not penetrate it due to the presence of the end mirror 46. The calibration strip 70 and associated processing may be configured such that the LCI system 10 provides a first reading when the calibration strip 70 is not in contact with the LCI system 10 and a corrected reading when in contact with the calibration strip. Furthermore, the calibration strip may be configured as a disposable item.

Expansions for Ranging and Variable Depth Measurements

Figure 21:
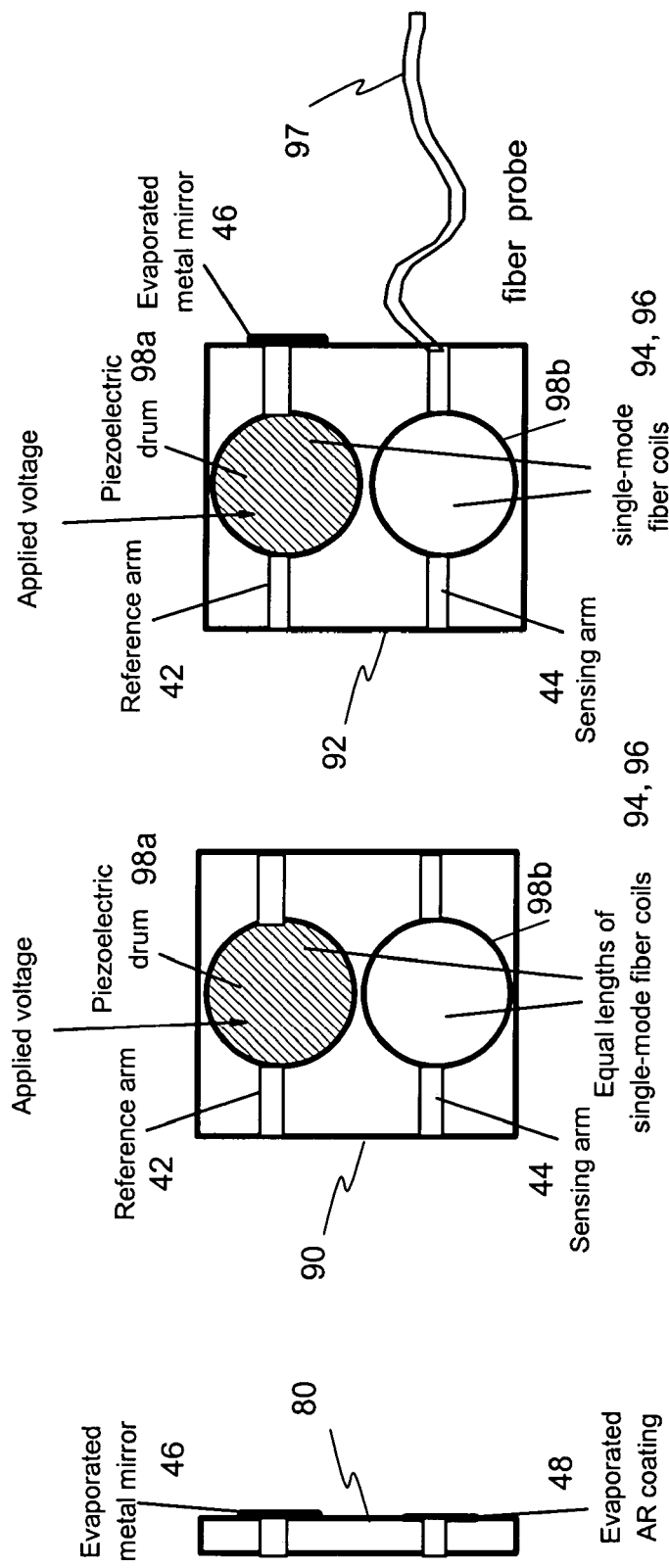
FIG. 21A depicts an interface for extension modules in accordance with another exemplary embodiment of the invention.
FIG. 21B depicts an interface for extension in accordance with another exemplary embodiment of the invention.
FIG. 21C depicts another interface for extension in accordance with yet another exemplary embodiment of the invention.

As describe above, some applications may require the probing depth to be dynamic to enable locating and or depth scanning. For example, in medical diagnostics or imaging, the operator may need to probe for features such as tumors, characterized by large changes of optical properties (absorption, reflection, or refractive index change due to a different density). FIGS. 21A–21C depict various adapters and several expansion or extension modules 90, 92, which can be attached to the modular LCI system 10, 10b of FIGS. 16 and 17, for example, to provide additional versatility and functionality. FIG. 21A, depicts an adapter 80, configured, in one exemplary embodiment as a short section of waveguides 82, preferably, but not necessarily, made of the same material as the splitter-modulator 40a, 40b, with mirror 46 and AR coating 48, which can be attached to the splitter-modulator 40a, 40b (with matching fluid) to operate as an interface for various extension modules 90, 92. The purpose of the extension module 90 is to provide for adequate lengths of the reference and sensing arms 42, 44 while using a minimum of space, and for adjusting the length of the reference arm 42 and/or sensing arm 44 to enable probing at various depths for example the extension modules may even be employed to facilitate the interferometer portion of the autocorrelator embodiment for the LCI system 10b of FIG. 17. It should be appreciated that the length of the arms 42, 44 can be adjusted in any number of ways, including mechanically changing an air gap between two sections of the reference arm, moving the mirror 46, actually modifying the length of the arm, and the like, as well as combinations including at least one of the foregoing. A preferred way to manipulate the length of an arm 42, 44, in this instance the reference arm 42, in order to maintain small size, accuracy, and stability, is to perform this operation electromechanically.

Referring now to FIGS. 21B and 21C, in yet another exemplary embodiment, an extension modules 90 and 92 including windings of two lengths of single-mode fibers 94, 96, preferably a polarization maintaining fiber (PMF), (reference and sensing arms respectively) on two drums 98a and 98b. In one embodiment, the drum for the reference arm 42 is made out of a piezoelectric material such as, but not limited to PZT (lead zirconate titanate). The diameter of the drums 98a, 98b is selected to be large enough to prevent radiation from the fibers 94, 96 due to the bending for example, about 3–4 centimeters (cm). The diameter of the fibers 94, 96 with claddings is of the order of 0.12 mm. The application of a voltage to the PZT drum 98a causes it to expand or contract, thus straining the reference fiber 94 (for example) and changing its effective length and thereby the optical path length for the reference arm 42. Therefore, as the total length of the unstrained fiber is increased, the total expansion increases as well. For example, if the strain limit for the fiber 94 is about $\Delta l/l$ is $10^{-4}$, then, it requires a 10-meter length of fiber 94 to provide for about a 1 mm extension. Advantageously, a length tens of meters is relatively easy to achieve if the fiber 94 is not too lossy. In the 1.3 μm to 1.55 μm wavelength range, the absorption in optical fibers 94, 96 is of the order of 0.2 dB/Km. There for the losses associated with a 10 meter length would be quite small. Thus, the approach of using a voltage applied a piezoelectric drum e.g., 98a wound with a fiber 94 coil is an effective means to provide changes of several millimeters in the optical path length of the reference arm 42.

Continuing with FIGS. 21B and 21C, the extension module 90 is configured to provide the extension of the reference and sensing arms 42 and 44 as described above and interfaces with an adapter 80 to facilitate depth profiling. Extension module 92 also includes an evaporated metal mirror 46 to terminate the reference arm 42, while the sensing arm 44 is terminated with a fiber probe 300 configured to facilitate probing such as may include a guidewire 302 and catheter.

Figure 22:
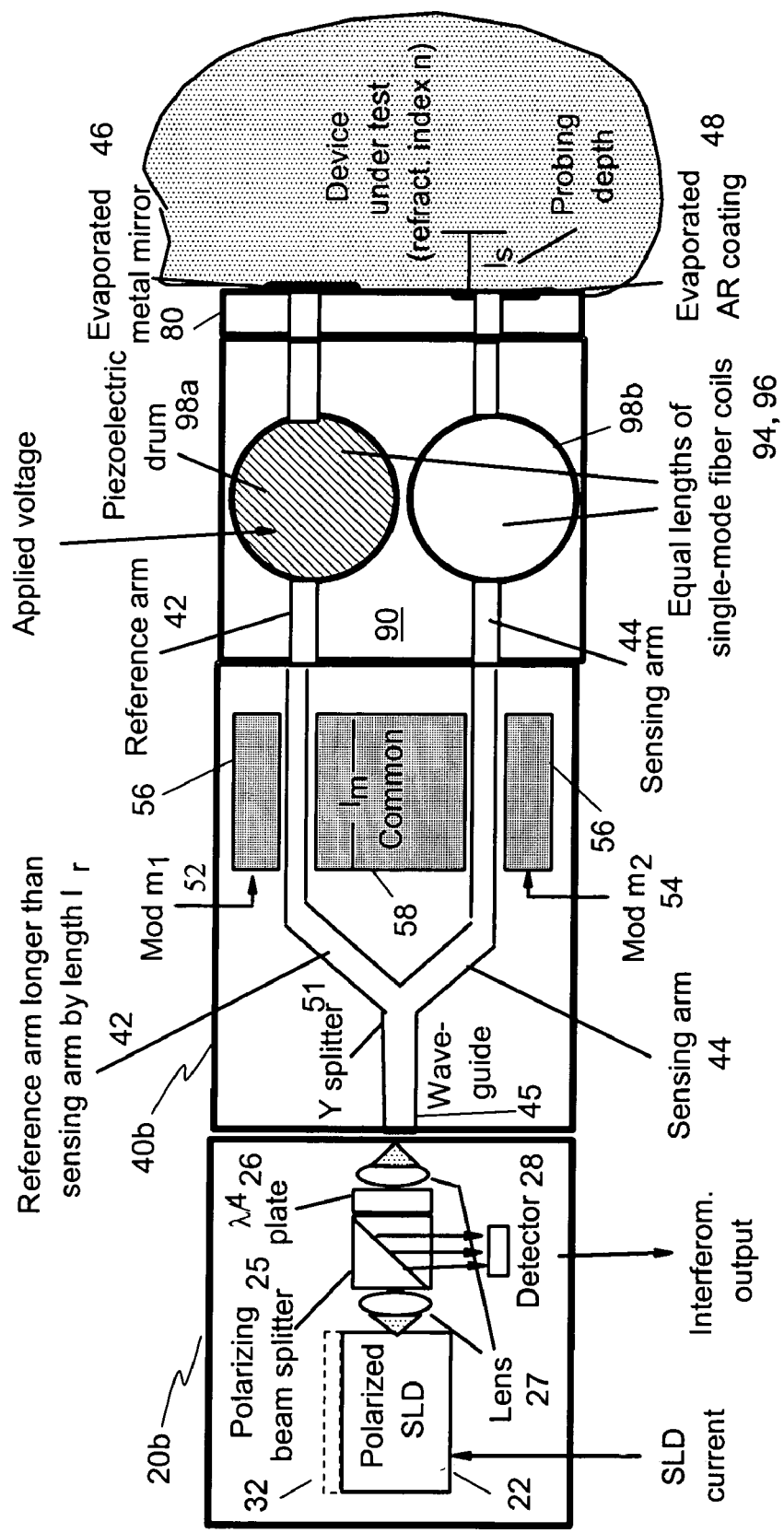
FIG. 22 depicts a miniaturized, handheld LCI system in accordance with an exemplary embodiment.
Figure 23:
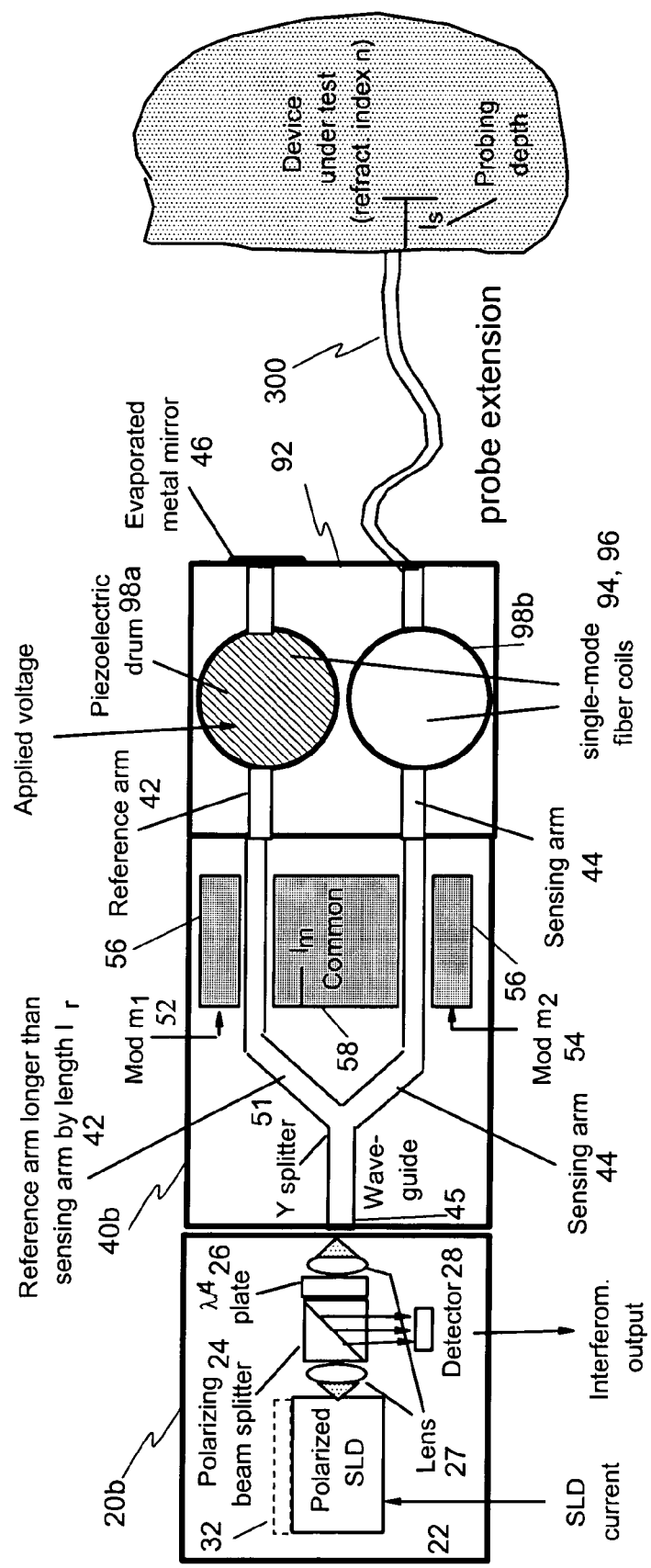
FIG. 23 depicts a miniaturized, handheld LCI system in accordance with an exemplary embodiment.

FIGS. 22 and 23 depict various implementations of the extended instrument starting from the base configuration depicted in FIGS. 16 and 17 and using the adapter and the extension modules 80, 90, and 92. FIG. 22 depicts a configuration of an exemplary embodiment where in addition to the source-detector module 20a, 20b and splitter modulator module 40a, 40b and extension module 90 and adapter 80 are employed. This configuration facilitates probing at various depths as well as facilitating depth profile scanning. FIG. 22 depicts a configuration of another exemplary embodiment where in addition to the source-detector module 20 and splitter modulator module 40 and extension module 92 including an external probe 300 are employed. This configuration facilitates probing either at a distance from the device or remote internal probing such as with a catheter and guidewire 302.

Figure 24:
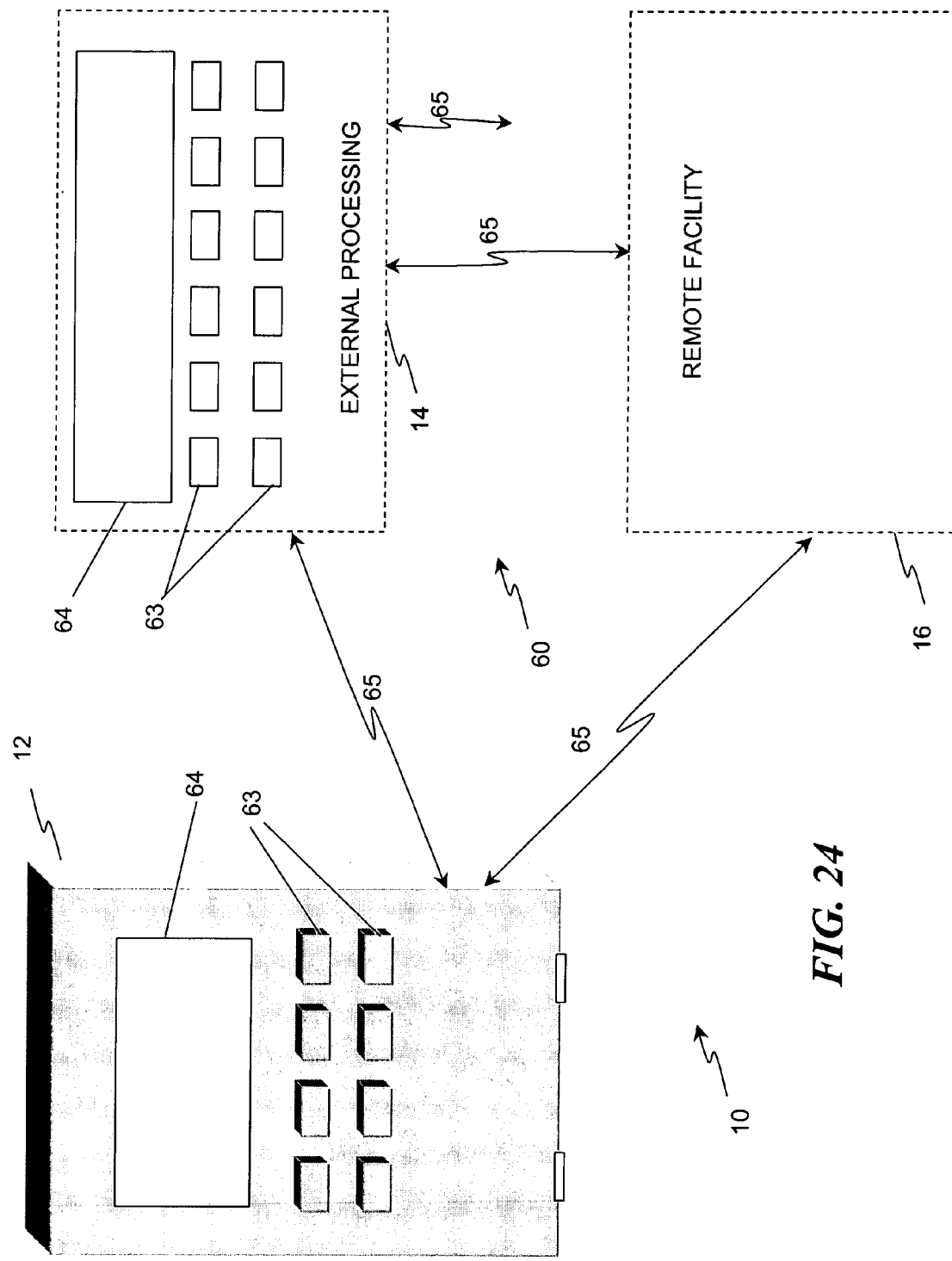
FIG. 24 depicts a miniaturized, handheld LCI system in accordance with an exemplary embodiment.

Referring now to FIG. 24, a miniaturized, optionally handheld, LCI system 10 is depicted in accordance with an exemplary embodiment. In an exemplary embodiment, the LCI system 10 is packaged in a small enclosure 12 and includes, but is not limited to, various modules including, but not limited to source-detector module 20a, 20b, splitter-modulator module 40a, 40b and may include one or more additional extension, adapter or interface modules such as 80, 90, and 92 or even calibration strip 70. In addition, also optionally packaged within the enclosure may be processing system 60, including processor 62 (not shown in this view) associated controls 63 e.g., keys, selectors, pointers, and the like, display 64, data media 66, as well as communication interfaces 65, and the like as well as rechargeable batteries. Therefore, in one exemplary embodiment the LCI system 10 as packaged in enclosure 12 should be comparable in size to that of a Personal Digital Assistant (PDA) or small handheld instrument, e.g., about 8 cm×12 cm×3 cm to readily facilitate handheld operation. It should be appreciated, that the package could be larger or smaller as needed to fit the desired component configurations.

Continuing with FIG. 24, it should also be appreciated as mentioned earlier, that various portions of the LCI system 10, and particularly, processing system 60 may be enclosed within the enclosure 12, or associated with an external processing unit 14, or remotely located, such as with a computer processing system 60 in another facility 16. In yet another exemplary embodiment, the LCI system 10 may also include communication interfaces 65, including wireless interfaces (e.g., infrared, radio frequency, or microwave transmitter/receiver) similar to modem computers, cell phones, PDAs, and the like to enable communication, including, but not limited to Internet communication, with external systems 14 and remote facilities 16. For example, a sensing portion including the source-detector module 20a, 20b and splitter-modulator module 40a, 40b can be detachable, in the form small handheld device, while the rest of the remainder of the LCI system 10 may be in a separate package, separate computer, and the like.

The disclosed invention can be embodied in the form of computer, controller, or processor implemented processes and apparatuses for practicing those processes. The present invention can also be embodied in the form of computer program code containing instructions embodied in tangible media 66 such as floppy diskettes, CD-ROMs, hard drives, memory chips, or any other computer-readable storage medium, wherein, when the computer program code is loaded into and executed by a computer, controller, or processor 62, the computer, controller, or processor 62 becomes an apparatus for practicing the invention. The present invention may also be embodied in the form of computer program code as a data signal 68 for example, whether stored in a storage medium, loaded into and/or executed by a computer, controller, or processor 62 or transmitted over some transmission medium, such as over electrical wiring or cabling, through fiber optics, or via electromagnetic radiation, wherein, when the computer program code is loaded into and executed by a computer 62, the computer 62 becomes an apparatus for practicing the invention. When implemented on a general-purpose processor the computer program code segments configure the processor to create specific logic circuits.

It will be appreciated that the use of first and second or other similar nomenclature for denoting similar items is not intended to specify or imply any particular order unless otherwise stated.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for diagnosing a human condition from a characteristic of tissue in a biological sample, the method comprising:
   directing broadband light by means of a sensing light path at the biological sample, said sensing light path having an effective light path length;
   receiving said broadband light reflected from the biological sample by means of said sensing light path;
   directing said broadband light by means of a reference light path at a reference reflecting device, said reference light path having an effective light path length;
   receiving said broadband light reflected from said reference reflecting device by means of said reference light path;
   directing said broadband light reflected from the biological sample and reflected from said reference reflecting device at a first reflecting device by means of a first light path and at a second reflecting device by means of a second light path, said first and second light paths having corresponding effective light path lengths;
   combining said broadband light reflected from said first reflecting device and reflected from said second reflecting device;
   modulating said effective light path lengths of said first and second light paths to minimize a difference to within about two coherence lengths of said broadband light, said difference corresponding to the effective light path lengths of said reference light path and said sensing light path;
   detecting said broadband light resulting from broadband light reflected from said first depth in the biological sample and said broadband light reflected from said reference reflecting device, to generate a signal indicative of an interference of said broadband light reflected from said first depth in the biological sample and said broadband light reflected from said reference reflecting device;
   determining a first phase from said signal indicative of said interference of said broadband light reflected from said first depth in the biological sample and said broadband light reflected from said reference reflecting device;
   changing the effective light path length of at least one of said reference light path and said sensing light path to define a second depth;
   detecting said broadband light resulting from said broadband light reflected from said second depth in the biological sample and said broadband light reflected from said reference reflecting device, to generate a signal indicative of an interference of said broadband light reflected from said second depth in the biological sample and said broadband light reflected from said reference reflecting device;
   determining a second phase from said signal indicative of said interference of said broadband light reflected from said second depth in the biological sample and said broadband light reflected from said reference reflecting device;
   determining the characteristic of the biological sample from said first phase and said second phase; and
   diagnosing a human condition from the characteristic.

2. The method of claim 1 wherein at least one of said first light path and said second light path includes at least one of an optical fiber and a waveguide.

3. The method of claim 2 wherein said modifying said effective light path lengths of said first and second light paths comprises modulating excitation to metallic electrodes disposed at an optical waveguide.

4. The method of claim 2 wherein said modifying said effective light path lengths of said first and second light paths comprises modulating excitation to a piezoelectric drum having said optical fiber wound thereon forming at least a portion of at least one of said first light path and said second light path.

5. The method of claim 2 wherein said modifying said effective light path lengths of said first and second light paths comprises moving at least one of said first reflecting device on said first light path and second reflecting device on said second light path.

6. The method of claim 1 wherein at least one of said first reflecting device and said second reflecting device is fixed.

7. The method of claim 1 wherein at least one of said reference light path end said sensing light path includes at least one of an optical fiber and a waveguide.

8. The method of claim 7 wherein said changing said effective light path lengths comprises modulating excitation to metallic electrodes disposed at an optical waveguide.

9. The method of claim 7 wherein said changing said effective light path lengths comprises modulating excitation to a piezoelectric drum having said optical fiber wound thereon forming at least a portion of at least one of said reference light path and said sensing light path.

10. The method of claim 1 wherein said changing said effective light path lengths comprises moving said reflecting device on said reference light path.

11. The method of claim 1 wherein said reference reflecting device is fixed.

12. The method of claim 1 wherein at least one of said determining a first phase and said determining a second phase comprises:
    modulating said effective light path lengths of at least one of said reference light path and said sensing light path In accordance with a modulator function having a phase component; and
    determining a magnitude of change of said effective light path lengths inhxoduced by said modulating when said phase component of said modulator function is generally null.

13. The method of claim 12 wherein said modulator function comprises a sinusoidal modulator function.

14. The method of claim 12 wherein said modulator function comprises ramp modulator function.

15. The method of claim 12 wherein said modulating comprises modulating excitation to metallic electrodes disposed at an optical waveguide.

16. The method of claim 12 wherein said modulating comprises modulating excitation to a piezoelectric drum having said optical fiber wound thereon forming at least a portion of at least one of said reference light path and said sensing light path.

17. The method of claim 12 wherein said determining said magnitude of change of said effective light pat lengths introduced by said modulating comprises balancing said broadband light resulting from interference of said broadband light reflected from the biological sample with a feed back loop.

18. The method of claim 1 further comprising calibrating at least one of said reference light path and said sensing light path by adjusting said effective light path lengths of at least one of said reference light path and said sensing light path based on a sample exhibiting known properties.

19. The method of claim 1 wherein said determining the characteristic of the biological sample comprises determining a difference between said first phase and said second phase based on said first depth and said second depth.

20. The method of claim 19 wherein said determining a difference between said first phase and said second phase based on said first depth and said second depth comprises:
    identifying the characteristic of the biological sample as within a medium if said difference between said first phase and said second phase is less than about a threshold; and
    identifying the characteristic of the biological sample as a boundary between mediums if said difference between said first phase and said second phase exceeds about said threshold.

21. The method of claim 1 wherein said determining the characteristic of the biological sample comprises determining a difference between said first phase and said second phase based on a difference between said first depth and said second depth.

22. The method of claim 21 wherein said determining a difference between said first phase and said second phase based on a difference between said first depth and said second depth comprises:
    identifying the characteristic of the biological sample as within a medium if a ratio of a rate of said difference between said first phase and said second phase and a said difference between said first depth and said second depth is less than about a threshold; and
    identifying the characteristic of the biological sample as a boundary between mediums if said ratio of said rate of said difference between said first phase and said second phase and said difference between said first depth and said second depth exceeds about said threshold.

23. The method of claim 12 further comprising determining a first variation in an index of refraction of the biological sample from said magnitude of change of said effective light path lengths and said first depth, said first variation in said index of refraction from a ratio of said magnitude of change of said effective light path length and said first depth.

24. The method of claim 22 wherein said magnitude of change of said effective light path lengths comprises one of a numerator and a denominator of said ratio and said first depth comprises an other of said numerator and said denominator of said ratio.

25. The method of claim 22 further comprising determining a second variation in an index of refraction of the biological sample from said magnitude of change of said effective light path lengths and said second depth, said second variation in said index of refraction from a ratio of said magnitude of change of said effective light path length and said second depth.

26. The method of claim 25 wherein said magnitude of change of said effective light path lengths comprises one of a numerator and a denominator of said ratio and said second depth comprises an other of said numerator and said denominator of said ratio.

27. The method of claim 1 further comprising determining a first magnitude of said broadband light resulting from said interfering based on said first depth.

28. The method of claim 27 further comprising determining a second magnitude of said broadband light resulting from said interfering based on said second dept.

29. The method of claim 27 further comprising determining the characteristic of the biological sample from said first magnitude and said second magnitude.

30. The method of claim 29 wherein said determining the characteristic of the biological sample comprises determining a difference between said first magnitude and said second magnitude based on said first depth and said second depth.

31. The method of claim 30 wherein said determining a difference between said first magnitude and said second magnitude based on said first depth and said second depth comprises:

identifying the characteristic of the biological sample as within a medium if said difference between said first magnitude and said second magnitude is less than about a threshold; and identifying the characteristic of the biological sample as a boundary between mediums if said difference between said first magnitude and said second magnitude exceeds about said threshold.

32. The method of claim 27 wherein said determining the characteristic of the biological sample comprises determining a difference between said first magnitude and said second magnitude based on a difference between said first depth and said second depth.

33. The method of claim 31 wherein said determining a difference between said first magnitude and said second magnitude based on a difference between said first depth and said second depth comprises:

identifying the characteristic of the biological sample as within a medium if a ratio of a rate of said difference between said first magnitude and said second magnitude and a said difference between said first depth and said second depth is less than about a threshold; and identifying the characteristic of the biological sample as a boundary between mediums if said ratio of said rate of said difference between said first magnitude and said second magnitude and said difference between said first depth and said second depth exceeds about said threshold.

34. A system for determining a characteristic of tissue in a biological sample, the system comprising:

a broadband light source for providing a broadband light;

a sensing light path receptive to said broadband light from said broadband light source, said sensing light path configured to direct said broadband light at the biological sample and to receive said broadband light reflected from the biological sample;

a reference reflecting device;

a reference light path receptive to said broadband light from said broadband light source, said reference light path configured to direct said broadband light at said reference reflecting device and to receive said broadband light reflected from said reflecting device;

a first Light path receptive to said broadband light reflected from the biological sample and reflected from said reference reflecting device, said first light path configured to direct said broadband light reflected from the biological sample and reflected from said reference reflecting device at a first reflecting device;

a second light path receptive to said broadband light reflected from the biological sample and reflected from said reference reflecting device, said second light path configured to direct said broadband light reflected from the biological sample and reflected from said reference reflecting device at a second reflecting device, said first and second light paths having corresponding effective light path lengths; and means for modifying said effective light path lengths of said first and second light paths to minimize a difference to within about two coherence lengths of said broadband light, said difference corresponding to the effective light path lengths of said reference light path and said sensing light path;

a detector receptive to said broadband light resulting from said broadband light reflected from the biological sample and said broadband light reflected from said reference reflecting device, to generate signals indicative of an interference of said broadband light reflected from the biological sample and said broadband light reflected from said reference reflecting device;

means for changing an effective light path length of at least one of said reference light path and said sensing light path to define a second depth; and a processor configured to: (1) determine a first phase from said signal indicative of said interference of said broadband Light reflected from a first depth in the biological sample and said broadband light reflected from said reference reflecting device, said first depth defined by said effective light path length of said sensing light path and said effective light path length of said reference light path; (2) determine a second phase from said signal indicative of said interference of said broadband light reflected from a second depth in the biological sample and said broadband light reflected from said reference reflecting device, said second depth defined by said effective light path length of at least one of said sensing light path and a reference light path having been changed; and (3) determine the characteristic of the biological sample from said first phase and said second phase.

35. The system of claim 34 wherein at least one of said first light path and said second light path includes at least one of an optical fiber and a waveguide.

36. The system of claim 35 wherein said means for modifying said effective light path lengths of said first and second light paths comprises a modulator having metallic electrodes disposed at an optical waveguide.

37. The system of claim 35 wherein said means for modifying said effective light path lengths of said first and second light paths comprises a modulator formed with a piezoelectric drum having said optical fiber wound thereon forming at least a portion of at least one of said first light path and said second light path.

38. The system of claim 35 wherein said means for modifying said effective light path lengths of said first and second light paths comprises moving at least one of said first reflecting device on said first light path and second reflecting device on said second light path.

39. The system of claim 34 wherein at least one of said first reflecting device and said second reflecting device is fixed.

40. The system of claim 34 wherein said first depth is based on a difference between said effective light path lengths of said first light path and said second light path.

41. The system of claim 34 wherein said second depth is defined by a difference between said effective light path lengths of said first light path and said second light path.

42. The system of claim 34 wherein at least one of said reference light path and said sensing light path comprises at least one of an optical fiber and a waveguide.

43. The system of claim 42 wherein said means for changing comprises a modulator of metallic electrodes disposed at an optical waveguide.

44. The system of claim 42 wherein said means for changing comprises a modulator formed with a piezoelectric drum with an optical fiber wound thereon forming at least a portion of at least one of said reference light path and said sensing light path.

45. The system of claim 34 wherein said first depth is defined by a difference between said effective light path lengths of said reference light pat and said sensing light path.

46. The system of claim 34 wherein said second depth is defined by a difference between said effective light path lengths of said reference light path and said sensing light path.

47. The system of claim 34 wherein said reflecting device is fixed.

48. The system of claim 34 further including a modulator associated with at least one of said reference light path and said sensing light path, said modulator for modulating said effective light path lengths of said at least one of said reference light path and said sensing light path in accordance with a modulator function having a phase component.

49. The system of claim 48 wherein said processor is further configured to determine a magnitude of change of said effective light path length introduced by said modulator when said phase component of said modulator function is generally null for at cast one of said first phase and determine said second phase.

50. The system of claim 48 wherein said modulator comprises a sinusoidal modulator.

51. The system of claim 48 wherein said modulator comprises a ramp modulator.

52. The system of claim 48 wherein said modulator comprises metallic electrodes disposed at an optical waveguide.

53. The system of claim 48 wherein said modulator comprises a piezoelectric drum with an optical fiber wound thereon forming at least a portion of at Least one of said reference light path and said sensing light path.

54. The system of claim 48 further comprising a feedback loop associated with said modulator operating on a limit of said modulating such that said broadband light resulting from said interference is balanced.

55. The system of claim 34 further comprising a calibrating strip for calibrating at least one of said reference light path and said sensing light path to adjust said effective light path length of at least one of said reference light path and said sensing light path based on a sample exhibiting known properties.

56. The system of claim 34 wherein the characteristic of the biological sample is determined based on a difference between said first phase and said second phase and said first depth and said second depth.

57. The system of claim 56 wherein:
the characteristic of the biological sample is identified as within a single medium if said difference between said first phase and said second phase is less than about a threshold; and
the characteristic of the biological sample is identified as a boundary between mediums if said difference between said first phase and said second phase exceed about said threshold.

58. The system of claim 34 wherein the characteristic of the biological sample Is determined based on a difference between said first phase and said second phase and a difference between said first depth and said second depth.

59. The system of claim 58 wherein:
the characteristic of the biological sample is identified as within a single medium if a ratio of a rate of said difference between said first phase and said second phase and a difference between said first depth and said second depth is less than about a threshold; and
the characteristic of the biological sample is identified as a boundary between mediums if said ratio of said rate of said difference between said first phase and said second phase and a difference between said first depth and said second depth exceeds about said threshold.

60. The system of claim 49 further comprising said processor determines a first variation in an index of refraction of the biological sample from said magnitude of change of said effective light path lengths and said first depth, said first variation in said index of refraction comprising ratio of said magnitude of change of said effective light path lengths and said first depth.

61. The system of claim 60 wherein said magnitude of change of said effective light path lengths comprises one of a numerator and a denominator of said ratio and said first depth comprises an other of said numerator and said denominator of said ratio.

62. The system of claim 60 further comprising said processor determines a second variation in an index of refraction of the biological sample from said magnitude of change of said effective light path lengths and said second depth, said second variation in said index of refraction comprising a ratio of maid magnitude of change of said effective light path lengths and said second depth.

63. The system of claim 62 wherein said magnitude of change of said effective light path lengths comprises one of a numerator and a denominator of said ratio and said first depth comprises an other of said numerator and said denominator of said ratio.

64. The system of claim 34 further comprising said processor determines a first magnitude of said broadband light resulting from said interference based on said first depth.

65. The system of claim 64 further comprising said processor determines a second magnitude of said broadband light resulting from said interference based on said second depth.

66. The system of claim 65 further comprising said processor determines the characteristic of the biological sample from said first magnitude and said second magnitude.

67. The system of claim 66 wherein the characteristic of the biological sample is determined based on a difference between said first magnitude and said second magnitude based on said first depth and said second depth.

68. The method of claim 67 wherein:
the characteristic of the biological sample is identified as within a medium if said difference between said first magnitude and said second magnitude is less than about a threshold; and
the characteristic of the biological sample is identified as a boundary between mediums if said difference between said first magnitude and said second magnitude exceeds about said threshold.

69. The system of claim 66 wherein the characteristic of the biological sample is determined based on a difference between said first magnitude and said second magnitude based on a difference between said first depth and said second depth.

70. The system of claim 69 wherein:
the characteristic of the biological sample is identified as within a medium if a ratio of a rate of said difference between said first magnitude and said second magnitude and said difference between said first depth and said second depth is less than about a threshold; and
the characteristic of the biological sample is identified as a boundary between mediums if said ratio of said rate of said difference between said first magnitude and said second magnitude and a difference between said first depth and said second depth exceeds about said threshold.

* * * * *